US010306874B2

(12) United States Patent
Mujica et al.

(10) Patent No.: US 10,306,874 B2
(45) Date of Patent: Jun. 4, 2019

(54) NON-HUMAN ANIMALS HAVING A HUMANIZED LYMPHOCYTE-ACTIVATION GENE 3

(71) Applicant: Regeneron Pharmaceuticals, Inc., Tarrytown, NY (US)

(72) Inventors: Alexander O. Mujica, Elmsford, NY (US); Elena Burova, Mount Kisco, NY (US); Andrew J. Murphy, Croton-on Hudson, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 15/355,392

(22) Filed: Nov. 18, 2016

(65) Prior Publication Data

US 2017/0142943 A1    May 25, 2017

Related U.S. Application Data

(60) Provisional application No. 62/258,181, filed on Nov. 20, 2015, provisional application No. 62/370,430, filed on Aug. 3, 2016.

(51) Int. Cl.
| | |
|---|---|
| *A01K 67/027* | (2006.01) |
| *A61K 48/00* | (2006.01) |
| *C07H 21/04* | (2006.01) |
| *C07K 14/00* | (2006.01) |
| *C12N 15/00* | (2006.01) |
| *C07K 14/705* | (2006.01) |
| *A61K 49/00* | (2006.01) |

(52) U.S. Cl.
CPC ...... *A01K 67/0278* (2013.01); *A01K 67/0276* (2013.01); *A61K 49/0008* (2013.01); *C07K 14/70503* (2013.01); *A01K 2207/15* (2013.01); *A01K 2217/072* (2013.01); *A01K 2217/075* (2013.01); *A01K 2217/15* (2013.01); *A01K 2227/105* (2013.01); *A01K 2267/01* (2013.01); *A01K 2267/03* (2013.01); *A01K 2267/0331* (2013.01); *C07H 21/04* (2013.01); *C12N 2517/02* (2013.01)

(58) Field of Classification Search
CPC .......... A01K 67/0278; A01K 2227/105; A01K 2267/0331; C07H 21/04; C07K 14/70503; C12N 2517/02
USPC ........ 800/18, 25; 424/93.21; 536/23.4, 24.1; 530/350
See application file for complete search history.

(56) References Cited

U.S. PATENT DOCUMENTS

| | | | |
|---|---|---|---|
| 2014/0309487 A1 | 10/2014 | Lee et al. | |
| 2015/0366174 A1 | 12/2015 | Burova et al. | |
| 2016/0157469 A1 | 6/2016 | Burova et al. | |

FOREIGN PATENT DOCUMENTS

| | | |
|---|---|---|
| WO | 02/36789 | 5/2002 |
| WO | 2004/078928 A2 | 9/2004 |
| WO | 2011/044050 A2 | 4/2011 |
| WO | 2012/112544 A2 | 8/2012 |
| WO | 2013/063361 A1 | 5/2013 |
| WO | 2014/039782 A2 | 3/2014 |
| WO | 2015/196051 A1 | 12/2015 |

OTHER PUBLICATIONS

Houdebine, Louis-Marie, 2007, Methods in Molecular Biology, vol. 360, p. 163-202.*
Carstea et al., 2009, World Journals of Stem Cells, vol. 1, No. 1, p. 22-29.*
Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Devoy et al., 2012, Nature Reviews Genetics, vol. 13, p. 14-20.*
Selsby et al., 2015, ILAR Journal, vol. 56, No. 1, p. 116-126.*
Maksimenko et al., 2013, Acta Naturae, vol. 5, No. 1, p. 33-46.*
Brehm M.A. et al., "Overcoming Current Limitations in Humanized Mouse Research", The Journal of Infectious Diseases 208(Suppl 2):S125-S130 (2013).
Chen L. et al., "Molecular Mechanisms of T Cell Co-Stimulation and Co-Inhibition", Nature Reviews-Immunology 13:227-242 (Apr. 2013), together with an Erratum of the Article.
Chen Q. et al., "Expression of Human Cytokines Dramatically Improves Reconstitution of Specific Human-Blood Lineage Cells in Humanized Mice", PNAS 106(51):21783-21788 (Dec. 22, 2009), together with Supporting Information.
Croci D.O. et al., "Dynamic Cross-Talk Between Tumor and Immune Cells in Orchestrating the Immunosuppressive Network at the Tumor Microenvironment", Cancer Immunol Immunother 56:1687-1700 (2007).
Ferris R.L. et al., "Too Much of a Good Thing? Tim-3 and TCR Signaling in T Cell Exhaustion", The Journal of Immunology 193:1525-1530 (2014).
Flies D.B. et al., "Blockade of the B7-H1/PD-1 Pathway for Cancer Immunotherapy", Yale Journal of Biology and Medicine 94:409-421 (2011).
Francisco L.M. et al., "The PD-1 Pathway in Tolerance and Auto-immunity", Immunological Reviews 236:219-242 (2010).

(Continued)

*Primary Examiner* — Shin Lin Chen
(74) *Attorney, Agent, or Firm* — Scully, Scott, Murphy & Presser, P.C.; Margarita Zippin

(57) ABSTRACT

Non-human animals, and methods and compositions for making and using the same, are provided, wherein the non-human animals comprise a humanization of a Lymphocyte activation gene 3 (Lag3). The non-human animals may be described, in some embodiments, as having a genetic modification to an endogenous Lag3 locus so that the non-human animals express a Lag3 polypeptide that includes a human portion and an endogenous portion (e.g., a non-human portion).

10 Claims, 17 Drawing Sheets

Specification includes a Sequence Listing.

(56) References Cited

OTHER PUBLICATIONS

Goldberg M.V. et al., "LAG-3 in Cancer Immunotherapy", Current Topics in Microbiology and Immunology 344:269-278 (2011).
Grosso J.F. et al., "LAG-3 Regulates CD8+ T Cell Accumulation and Effector Function in Murine Self-and Tumor-Tolerance Systems", The Journal of Clinical Investigation 117(11):3383-3392 (Nov. 2007).
Huard B. et al., "Characterization of the Major Histocompatibility Complex Class II Binding Site on LAG-3 Protein", Proc. Natl. Acad. Sci. USA 94:5744-5749 (May 1997).
Huard B. et al., "Lymphocyte-Activation Gene 3/Major Histocompatibility Complex Class II Interaction Modulates the Antigenic Response of CD4+ T Lymphocytes", Eur. J. Immunol. 24:3216-3221 (1994).
Huard B. et al., "Cellular Expression and Tissue Distribution of the Human LAG-3-Encoded Protein, an MHC Class II Ligand", Immunogenetics 39:213-217 (1994).
Huang C-T et al., "Role of LAG-3 in Regulatory T Cells", Immunity 21:503-513 (Oct. 2004).
Ito R. et al., "Current Advances in Humanized Mouse Models", Cellular & Molecular Immunology 9:208-214 (2012).
Kisielow M. et al., "Expression of Lymphocyte Activation Gene 3 (LAG-3) on B Cells is Induced by T Cells", European Journal of Immunology 35:2081-2088 (2005).
Li N. et al., "Biochemical Analysis of the Regulatory T Cell Protein Lymphocyte Activation Gene-3 (LAG-3; CD223)", The Journal of Immunology 173:6806-6812 (2004).
Marcon-Lemaitre L. et al., "The Negative Regulatory Function of the Lymphocyte-Activation Gene-3 Co-Receptor (CD223) on Human T Cells", Immunology 115:170-178 (2005).
Nguyen L.T. et al., "Clinical Blockade of PD1 and LAG3-Potential Mechanisms of Action", Nature Reviews-Immunology 15:45-56 (Jan. 2015).
Norde W.J. et al., "Coinhibitory Molecules in Hematologic Malignancies: Targets for Therapeutic Intervention", Blood 120(4):728-736 (Jul. 26, 2012).
Pardoll D.M., "The Blockade of Immune Checkpoints in Cancer Immunotherapy", Nature Reviews Cancer 12:252-264 (Apr. 2012).
Rongvaux A. et al., "Human Thrombopoietin Knockin Mice Efficiently Support Human Hematopoiesis In Vivo", PNAS 108(6):2378-2383 (Feb. 8, 2011).
Shultz L.D. et al., "Humanized Mice for Immune System Investigation: Progress, Promise and Challenges", Nat Rev Immunol. 125(11):786-798 (Nov. 2012).
Shultz L.D. et al., "Generation of Functional Human T-Cell Subsets With HLA-Restricted Immune Responses in HLA Class I Expressing NOD/SCID/IL2rynull Humanized Mice", PNAS 107(29):13022-13027 (Jul. 20, 2010), together with Supporting Information.
Triebel F. et al., "LAG-3, a Novel Lymphocyte Activation Gene Closely Related to CD4", J. Exp. Med. 171:1393-1405 (May 1990).
Turnis M.E. et al., "Inhibitory Receptors as Targets for Cancer Immunotherapy", Eur. J. Immunol. 45:1892-1905 (2015).
Virgin H.W. et al., "Redefining Chronic Viral Infection", Cell 138:31-50 (Jul. 10, 2009).
Wei S. et al., "Tumor-Induced Immune Suppression of In Vivo Effector T-Cell Priming is Mediated by the B7-H1/PD-1 Axis and Transforming Growth Factor B", Cancer Research 68(13):5432-5438 (Jul. 1, 2008).
Wherry E J, "T Cell Exhaustion", Nature Immunology 12(6):492-499 (Jun. 2011).
Willinger T. et al., "Human IL-3/GM-CSF Knock-In Mice Support Human Alveolar Macrophage Development and Human Immune Responses in the Lung", PNAS 108(6):2390-2395 (Feb. 8, 2011).
Willinger T. et al., "Improving Human Hemato-Lymphoid System Mice by Cytokine Knock-In Gene Replacement", Trends in Immunology 32(7):321-327 (Jul. 2011).
Woo S-R et al., "Immune Tumoral Molecules LAG-3 and PD-1 Synergistically Regulate T-Cell Function to Promote Tumoral Immune Escape", Cancer Research 72(4):917-927 (Feb. 15, 2012).
Workman C.J. et al., "Lymphocyte Activation Gene-3 (CD223) Regulates the Size of the Expanding T Cell Population Following Antigen Activation In Vivo", The Journal of Immunology 172:5450-5455 (2004).
Zou W. et al., "Inhibitory B7-Family Molecules in the Tumour Microenvironment", Nature Reviews-Immunology 8:467-477 (Jun. 2008)
NCBI Reference Sequence No. NM_212513.2 (3 pages) (Jul. 31, 2016).
NCBI Reference Sequence No. NP_997678.2 (2 pages) (Jul. 31, 2016).
NCBI Reference Sequence No. NM_008479.2 (4 pages) (Feb. 15, 2015).
NCBI Reference Sequence No. NP_032505.1 (3 pages) (Feb. 15, 2015).
NCBI Reference Sequence No. NM_002286.5 (5 pages) (Oct. 6, 2016).
NCBI Reference Sequence No. NP_002277.4 (3 pages) (Oct. 6, 2016).
NCBI Reference Sequence No. NM_005018.2 (5 pages) (Sep. 15, 2016).
NCBI Reference Sequence No. NP_005009.2 (3 pages) (Sep. 15, 2016).
UniProtKB ID No. Q15116 (12 pages) (Nov. 30, 2016).
Burova E. et al., "Abstract 1484: Combined Treatment with Anti-LAG-3 and Anti-PD-1 Fully Human Monoclonal Antibodies Inhibits Tumor Growth in Immunocompetent Double-Humanized LAG-3/PD-1 Mice", Cancer Research 76 (14): (Jul. 1, 2016).
Burova E. et al., "Abstract 266: Antitumor Activity of REGN2810, a Fully Human Anti-PD-1 Monoclonal Antibody, Against MC38.Ova Tumors Grown in Immune-Competent Humanized PD-1 Mice", Cancer Research 75(15):2 pages (Aug. 1, 2015).
Devoy A. et al., "Genomically Humanized Mice: Technologies and Promises", Nature Reviews Genetics 13:14-20 (Jan. 1, 2012).
Huang R-Y et al., "LAG3 and PD1 Co-Inhibitory Molecules Collaborate to Limit CD8+ T Cell Signaling and Dampen Antitumor Immunity in a Murine Ovarian Cancer Model", Oncotarget 6(29):27359-27377 (Jul. 23, 2015).
Pennock G.K. et al., "The Evolving Role of Immune Checkpoint Inhibitors in Cancer Treatment", The Oncologist 20:812-822(2015).
Valenzuela D.M. et al., "High-Throughput Engineering of the Mouse Genome Coupled With High-Resolution Expression Analysis", Nature Biotechnology 21(6):652-659 (Jun. 2003).
Workman C.J. et al., "Phenotypic Analysis of the Murine CD4-Related Glycoprotein, CD223 (LAG-3)", Eur. J. Immunol. 32:2255-2263 (2002).
International Search Report and Written Opinion dated Feb. 10, 2017 received in International Application No. PCT/US2016/062733.
Chun T. et al., "Cloning of Rat Lymphocyte Activation Gene-3 (Lag3; CD223) cDNA and its mRNA Expression in Rat Tissues", European Journal of Immunogenetics 31:5-9 (Mar. 2004).
Gibbs R.A. et al., "Genome Sequence of the Brown Norway Rat Yields Insights into Mammalian Evolution", Nature 428:493-521 (Apr. 1, 2004).
Krzywinski M. et al., "Integrated and Sequence-Ordered BAC-and YAC-Based Physical Maps for the Rat Genome", Genome Research 14:766-779 (Apr. 2004).
Osoegawa K. et al., "BAC Resources for the Rat Genome Project", Genome Research 14:780-785 (Apr. 2004).
Tong C. et al., "Generating Gene Knockout Rats by Homologous Recombination in Embryonic Stem Cells", Nat. Protoc. 6(6):doi:10.1038/nprot.2011.338 (Jun. 2011).
Tong C. et al., "Production of p53 Gene Knockout Rats by Homologous Recombination in Embryonic Stem Cells", Nature 467:211-215 (Sep. 9, 2010).
GenBank NCBI Reference Sequence: NM_212513.2 (4 pages) (May 27, 2018).

\* cited by examiner

```
hLAG3     1   MWEAQFLGLLLFLQPLWVAPVKPLQPGAEVPVVWAQEGAPAQLPCSPTIPLQDLSLLRRAGVTWQHQPDSGPPAAAPGHPL    80
mLag3     1   MREDLLLGFLLLGLLWEAPVVSSGPGKELPVVWAQEGAPVHLPCSLKSPNLDPNFLRGGVIWQHQPDSGQPTPIP----    76
HumLAG3   1   MREDLLLGFLLLGLLWEAPVKPLQPGAEVPVVWAQEGAPAQLPCSPTIPLQDLSLLRRAGVTWQHQPDSGPPAAAPGHPL    80
                                  **************************************************** hLAG3     81  APGPHPAAPSSWGPRPRRYTVLSVGPGGLRSRSGRLPLQPRVQLDERGRQRGDFSLMLRPARRADAGEYRAAVHLRDRALSC   160
mLag3     77  ALDLHQGMPSPRQPAPGRYTVLSVAPGGLRSGRQPLHPVQLEERGLQRGDFSLMLRPALRTDAGEYHATVRLPNRALSC    156
HumLAG3   81  APGPHPAAPSSWGPRPRRYTVLSVGPGGLRSGRLPLQPRVQLDERGRQRGDFSLMLRPARRADAGEYRAAVHLRDRALSC   160
              *       ** *   ***** **** *   * * ******* *  ****  *   * ***** hLAG3    161  RLRLRLGQASMTASPPGSLRASDWVILNCSFSRPDRPASVHWFRNRGQGRVPVRESPHHHLAESFLFLPQVSPMDSGPWG   240
mLag3    157  SLRLRVGQASMIASPSGVLKLSDWVLLNCSFSRPDRPSVHWFQ--GQNRVPVYINSPRHFLAETFLILLPQVSPLDSGTWG   234
HumLAG3  161  RLRLRLGQASMTASPPGSLRASDWVILNCSFSRPDRPASVHWFRNRGQGRVPVRESPHHHLAESFLFLPQVSPMDSGPWG   240
                     *** * * * *  * *********     **      * * * *  ** hLAG3    241  CILTYRDGFNVSIMYNLITVLGLEPPTPLITVYAGAGSRVGLPCRLPAGVGTRSFLTAKWTPPGGGPDLLVTGDNGDFTLRL   320
mLag3    235  CVLTYRDGFNVSITYNLKVLGLIGLEPVAPLITVAAEGSRVELPCHLPPGVGTPSLLIAKWTPPGGPELPVAGKSGNFTLHL   314
HumLAG3  241  CILTYRDGFNVSIMYNLTVLGLEPVAPLITVLGLEPVAPLITVAAEGSRVELPCHLPPGVGTPSLLIAKWTPPGGPELPVAGKSGNFTLHL   320
              ********* * *            * *   *** *     * hLAG3    321  EDVSQAQAGTYTCHIHLQEEQLNATVTLAIITVTPKSFGSPGSLGKLLCEVTPVSGQERFVWSSLDTPSQRSFSGPWLEA   400
mLag3    315  EAVGLAQAGTYTCSIHLQGQLNATVTLAVITVTPKSFGLPGSRGKLLCEVTPASGKERFVWRPLNNLS-RSCPGPVLEI   393
HumLAG3  321  EAVGLAQAGTYTCSIHLQGQLNATVTLAVITVTPKSFGLPGSRGKLLCEVTPASGKERFVWRPLNNLS-RSCPGPVLEI   399
              *  *****  *   *******  ***  **** **  *  ****       * * *  ** hLAG3    401  QEAQLLSQPWQCQLYQGERLLGAAVYFTELSSPGAQRSGRAPGALPAGHILLFLLLIGVLSLLLLVTGAFGFHLWRRQWRP   480
mLag3    394  QEARLLAERWQCQLYEGQRLLGATVYAAEAESSS-GAHSARRISGDLKGGHLVLILGALSLFLLVAGAFGFHWWRKQLLL   472
HumLAG3  400  QEARLLAERWQCQLYEGQRLLGATVYAAEAESSS-GAHSARRISGDLKGGHLVLILGALSLFLLVAGAFGFHWWRKQLLL   478
              *   **   ****        *  ** *    **    *    *       *  * hLAG3    481  RRFSALEQGIHPPQAQSKIEELEQEPE------PEPEPEPEPEPEPEQL    525
mLag3    473  RRFSALEHGIQPFFPAQRKIEELELETEMGQEPEPEPEPQLEPEPRQL    521
HumLAG3  479  RRFSALEHGIQPFFPAQRKIEELELETEMGQEPEPEPEPQLEPEPRQL    527
              ******** *  *  *** *****                
``` hLAG3 - SEQ ID NO:6
mLag3 - SEQ ID NO:4
HumLAG3 - SEQ ID NO:8

*Rattus norvegicus* Lag-3 mRNA (SEQ ID NO:1, NCBI Reference Sequence NM_212513.2):

ACATTCTTTGCCTCACCTCCCTCCTTGTGGAATTTCTCTCTCTCTCTCTTTTTTTTTCT
CCCAGGACCTTTTTCTGAACTCCCTTGCAGGGCCTGTGAAGCCCGGGGGCCACAGAGGA
GATGAGGCAGGATCTGTTCCTTGACCTTTTGCTTCTGCAGCTGCTTTGGGAAGCTC
CAGTTGTGTCTTCAGGGCCTGGGAAAGAGCTCTCCGTGGTGTGGGCCCAGGAGGG
AGCTCCTGTCCATCTTCCCTGCAGCCTCGAATTTCCCCACCTGGATCCCAACTTTC
TGCGAAGAGGATGGGTCACCTGGCAACATCGACCAGACAGTGACCAACCCGCTTC
CATCCCGGCCCTTGACCTTCTCCAGGGAATGCCCTCGACTAGGAGACACCCACCCC
ATCGCTACACGGTGCTGAGTGTGGCTCCAGGAGGCCTGCGCAGCGGGAGGCAGCC
CCTGCTATCCCACGTGCAGCTGGAGAAGCGTGGCCCCAGCGCGGGGACTTCTCT
CTGTGGTTGCGCCCAGCTACGCGCAAAGATGCGGGCGAGTACCACGCCTTCGTGC
GCCTCCCGGACCGCGACTTCTCCTGCAGCCTCCGCCTGCGCGTCGGCCAGGCCTC
GATGATTGCCAGTCCCCCAGGAACCCTCAAGCCGTCTGATTGGGTCATTTTGAACT
GCTCCTTCAGTCGTCCTGACCGCCAGTCTCTGTGCACTGGTTCCAGGGCCAAAGC
CGAGTGCCCGTCCACAATTCACCCCGTCATTATCTAGCTGAAAGTTTCCTCTTACT
GCCCCAAGTCAGCCCACTGGATTCCGGGACCTGGGGCTGTGTCCTCACCTACAGA
GATGGCTTCAATGTCTCCATCACGTACAACCTCAAGGTTCAGGGTCTGGAACCTGT
AGCCCCTTTGACAGTGTACGCTGCTGAAGGTTCTAGGGTGGAGCTGCCCTGTCACT
TGCCTCCCGTTGTGGGGACCCCTTCTTTGCTCATTGCCAAGTGGACTCCTCCTGGG
GGAGGTCCTGAGCTCCGGTGACTGGAAAGAGTGGCAATTTTACCCTTCAACTTGA
GAATGTGGGTCGGGCACAGGCTGGGACCTACACCTGCAGCATCCATCTGCAGGGG
CGGCAGCTCAGTGCGGCTGTGACGTTGGCAGTCATCACAGTGACTCCTAAATCCTT
CGGGTTACCTGGCTCCCCGCAGAAGCTGTTATGTGAGGTAGTCCCGGCATCTGGA
GAAGGAAGATTTGTGTGGCGCCCCTCAGCGATCTGTCCAGGAGTTCCCTGGGCC
CTGTGCTGGAGTTGCAGGAGGCCAAGCTTCTGGCTGAGCAATGGCAGTGTCAGCT
GTATGAGGGCCAGAAACTTCTTGGAGCAACAGTGTACACCGCAGAGTCTAGCTCA
GGCGCCTGGAGTGCTAAGAGAATCTCAGGTGACCTTAAAGGAGGCCATCTCTTCC
TCTCTCTCATCCTTGGTGCCCTTGCCTTGTTCCTCTTGGTGACCGGGGCCTTTGGC
TTTCACCTGTGGAGAAGACAGTTGCTACGGAGAAGATTTTCTGCCTTAGAGCATGG
GATTCGCCCACCTCCGGTTCAGAGTAAGATAGAGGAGCTGGAGCGAGAACCGGAG
ACCGAGATGGAACCAGAGACAGAGCCCGATCCGGAGCCTCAGCCGGAGCCCGAGC
TGGAACCAGAGTCCAGGCAGCTCTGACCAGGAGCTGAGACAGCCAGCAGCAGGTCTC
AGCAGCTCTGCCCGCCCGCCCGCCTGCCCGCCCGCCGGAATAAACTCCCTGTCAGCAGC
AAAAAAAAAAAAAAAAAAAAAAAAAA

*Rattus norvegicus* Lag-3 amino acid (SEQ ID NO:2, NCBI Reference Sequence: NP_997678.2):

MRQDLFLDLLLLQLLWEAPVVSSGPGKELSVVWAQEGAPVHLPCSLEFPHLDPNFLRRGW
VTWQHRPDSDQPASIPALDLLQGMPSTRRHPPHRYTVLSVAPGGLRSGRQPLLSHVQLEKR
GPQRGDFSLWLRPATRKDAGEYHAFVRLPDRDFSCSLRLRVGQASMIASPPGTLKPSDWVIL
NCSFSRPDRPVSVHWFQGQSRVPVHNSPRHYLAESFLLLPQVSPLDSGTWGCVLTYRDGFN
VSITYNLKVQGLEPVAPLTVYAAEGSRVELPCHLPPVVGTPSLLIAKWTPPGGGPELPVTGK
SGNFTLQLENVGRAQAGTYTCSIHLQGRQLSAAVTLAVITVTPKSFGLPGSPQKLLCEVVPA
SGEGRFVWRPLSDLSRSSLGPVLELQEAKLLAEQWQCQLYEGQKLLGATVYTAESSSGAWS
AKRISGDLKGGHLFLSLILGALALFLLVTGAFGFHLWRRQLLRRRFSALEHGIRPPPVQSKIE
ELEREPETEMEPETEPDPEPQPEPELEPESRQL

FIGURE 8 (Continued)

*Mus musculus* Lag-3 mRNA (SEQ ID NO: 3, NCBI Reference Sequence: NM_008479.2):

GGGCAGTGGGGAGGAGAAGCAGAAGGACTGGGTCTGGAGGAGCAGCTCAAGTTCTAGC
TAGCTGCAGTGGGTTTGCCTGCACTCTGCTCTGGGTCCCAGCCCGGGCCTCTGATCATTA
TCCATCCTGCTGTCTCCAGTCCCCACTCCTGGGGCGTCCTCTTCACCCTACATTCTTTCCC
TCCGCCTCACCTCCTCCTTGTAGAACTTCTCTCTCTCTCTCTCTCTCTCTCTCTCTCTCT
CTCTCTCTCTGTGTGTGTGTGTGTCTGTCTGTCTGTCTGTCTCTCTCCTCCCAGG
ACCTTTTTCTAACCTCCCTTGGAGGGCTGGGGAGGCCCGGGCCATAGAGGAGATGAGG
GAGGACCTGCTCCTTGGCTTTTTGCTTCTGGGACTGCTTTGGGAAGCTCCAG<u>TTGT</u>
<u>GTCTTCAGGGCCTGGGAAAGAGCTCCCCGTGGTGTGGGCCCAGGAGGGAGCTCCC</u>
<u>GTCCATCTTCCCTGCAGCCTCAAATCCCCAACCTGGATCCTAACTTTCTACGAAG</u>
<u>AGGAGGGGTTATCTGGCAACATCAACCAGACAGTGGCCAACCCACTCCCATCCCG</u>
<u>GCCCTTGACCTTCACCAGGGGATGCCCTCGCCTAGACAACCCGCACCCGGTCGCT</u>
<u>ACACGGTGCTGAGCGTGGCTCCAGGAGGCCTGCGCAGCGGGAGGCAGCCCCTGC</u>
<u>ATCCCCACGTGCAGCTGGAGGAGCGCGGCCTCCAGCGCGGGGACTTCTCTCTGTG</u>
<u>GTTGCGCCCAGCTCTGCGCACCGATGCGGGCGAGTACCACGCCACCGTGCGCCTC</u>
<u>CCGAACCGCGCCCTCTCCTGCAGTCTCCGCCTGCGCGTCGGCCAGGCCTCGA</u>TGA
TTGCTAGTCCCTCAGGAGTCCTCAAGCTGTCTGATTGGGTCCTTTTGAACTGCTCC
TTCAGCCGTCCTGACCGCCCAGTCTCTGTGCACTGGTTCCAGGGCCAGAACCGAG
TGCCTGTCTACAACTCACCGCGTCATTTTTAGCTGAAACTTTCCTGTTACTGCCCC
AAGTCAGCCCCTGGACTCTGGGACCTGGGGCTGTGTCCTCACCTACAGAGATGG
<u>CTTCAATGTCTCCATCACGTACAACCTCAAGGTTCTGGGTCTGGAGCCCGTAGCCC</u>
CTCTGACAGTGTACGCTGCTGAAGGTTCTAGGGTGGAGCTGCCCTGTCATTTGCCC
CCAGGAGTGGGGACCCCTTCTTTGCTCATTGCCAAGTGGACTCCTCCTGGAGGAG
GTCCTGAGCTCCCCGTGGCTGGAAAGAGTGGCAATTTTACCCTTCACCTTGAGGCT
GTGGGTCTGGCACAGGCTGGGACCTACACCTGTAGCATCCATCTGCAGGGACAGC
AGCTCAATGCCACTGTCACGTTGGCGGTCATCACAG<u>TGACTCCCAAATCCTTCGGG</u>
<u>TTACCTGGCTCCGGGGGAAGCTGTTGTGTGAGGTAACCCCGGCATCTGGAAAGG</u>
<u>AAAGATTTGTGTGGCGTCCCTGAACAATCTGTCCAGGAGTTGCCCGGGCCCTGT</u>
<u>GCTGGAGATTCAGGAGGCCAGGCTCCTTGCTGAGCGATGGCAGTGTCAGCTGTAC</u>
<u>GAGGGCCAGAGGCTTCTTGGAGCGACAGTGTACGCCGCAGAGTCTAGCTCAGGCG</u>
<u>CCCACAGTGCTAGGAGAATCTCAGGTGACCTTAAAGGAGGCCATCTCGTTCTCGTT</u>
<u>CTCATCCTTGGTGCCCTCTCCCTGTTCCTTTTGGTGGCCGGGGCCTTTGGCTTTCA</u>
<u>CTGGTGGAGAAAACAGTTGCTACTGAGAAGATTTTCTGCCTTAGAACATGGGATTC</u>
<u>AGCCATTTCCGGCTCAGAGGAAGATAGAGGAGCTGGAGCGAGAACTGGAGACGGA</u>
<u>GATGGGACAGGAGCCGGAGCCCGAGCCGGAGCCACAGCTGGAGCCAGAGCCCAG</u>
<u>GCAGCTCTGACCTGGAGCCGAGGCAGCCAGCAGGTCTCAGCAGCTCCGCCCGCCCGCC</u>
CGCCCGCCCGAATAAACTCCCTGTCAGCAGCATCAAAAAAAAAAAAAAAAAA

FIGURE 8 (Continued)

*Mus musculus* Lag-3 amino acid (SEQ ID NO:4, NCBI Reference Sequence: NP_032505.1):

MREDLLLGFLLLGLLWEAPVVSSGPGKELPVVWAQEGAPVHLPCSLKSPNLDPNFLRRGGV
IWQHQPDSGQPTPIPALDLHQGMPSPRQPAPGRYTVLSVAPGGLRSGRQPLHPHVQLEERGL
QRGDFSLWLRPALRTDAGEYHATVRLPNRALSCSLRLRVGQASMIASPSGVLKLSDWVLLN
CSFSRPDRPVSVHWFQGQNRVPVYNSPRHFLAETFLLLPQVSPLDSGTWGCVLTYRDGFNV
SITYNLKVLGLEPVAPLTVYAAEGSRVELPCHLPPGVGTPSLLIAKWTPPGGGPELPVAGKS
GNFTLHLEAVGLAQAGTYTCSIHLQGQQLNATVTLAVITVTPKSFGLPGSRGKLLCEVTPAS
GKERFVWRPLNNLSRSCPGPVLEIQEARLLAERWQCQLYEGQRLLGATVYAAESSSGAHSA
RRISGDLKGGHLVLVLILGALSLFLLVAGAFGFHWWRKQLLLRRFSALEHGIQPFPAQRKIE
ELERELETEMGQEPEPEPEPQLEPEPRQL

*Homo sapiens* LAG-3 mRNA (SEQ ID NO:5, NCBI Reference Sequence: NM_002286.5):

ACAGGGGTGAAGGCCCAGAGACCAGCAGAACGGCATCCCAGCCACGACGGCCACTTTG
CTCTGTCTGCTCTCCGCCACGGCCCTGCTCTGTTCCCTGGGACACCCCGCCCCCACCTC
CTCAGGCTGCCTGATCTGCCCAGCTTTCCAGCTTTCCTCTGGATTCCGGCCTCTGGTCAT
CCCTCCCCACCCTCTCTCCAAGGCCCTCTCCTGGTCTCCCTTCTTCTAGAACCCCTTCCTC
CACCTCCCTCTCTGCAGAACTTCTCCTTTACCCCCCACCCCCCACCACTGCCCCCTTTCCT
TTTCTGACCTCCTTTTGGAGGGCTCAGCGCTGCCCAGACCATAGGAGAGATGTGGGAG
GCTCAGTTCCTGGGCTTGCTGTTTCTGCAGCCGCTTTGGGTGGCTCCAGTGAAGCC
TCTCCAGCCAGGGGCTGAGGTCCCGGTGGTGTGGGCCCAGGAGGGGGCTCCTGCC
CAGCTCCCCTGCAGCCCCACAATCCCCCTCCAGGATCTCAGCCTTCTGCGAAGAGC
AGGGGTCACTTGGCAGCATCAGCCAGACAGTGGCCCGCCCGCTGCCGCCCCGGC
CATCCCCTGGCCCCGGCCCTCACCCGGCGGCGCCCTCCTCCTGGGGCCCAGGC
CCCGCCGCTACACGGTGCTGAGCGTGGGTCCCGGAGGCCTGCGCAGCGGGAGGC
TGCCCCTGCAGCCCCGCGTCAGCTGGATGAGCGCGGCCGGCAGCGCGGGGACTT
CTCGCTATGGCTGCGCCCAGCCCGGCGCGCGGACGCCGGCGAGTACCGCGCCGC
GGTGCACCTCAGGGACCGCGCCCTCTCCTGCCGCCTCCGTCTGCGCCTGGGCCAG
GCCTCGATGACTGCCAGCCCCCAGGATCTCTCAGAGCCTCCGACTGGGTCATTTT
GAACTGCTCCTTCAGCCGCCCTGACCGCCCAGCCTCTGTGCATTGGTTCCGGAACC
GGGGCCAGGGCCGAGTCCCTGTCCGGGAGTCCCCCCATCACCACTTAGCGGAAAG
CTTCCTCTTCCTGCCCCAAGTCAGCCCCATGGACTCTGGGCCCTGGGGCTGCATCC
TCACCTACAGAGATGGCTTCAACGTCTCCATCATGTATAACCTCACTGTTCTGGGT
CTGGAGCCCCCAACTCCCTTGACAGTGTACGCTGGAGCAGGTTCCAGGGTGGGGC
TGCCCTGCCGCCTGCCTGCTGGTGTGGGGACCCGGTCTTTCCTCACTGCCAAGTG
GACTCCTCCTGGGGGAGGCCCTGACCTCCTGGTGACTGGAGACAATGGCGACTTT
ACCCTTCGACTAGAGGATGTGAGCCAGGCCCAGGCTGGGACCTACACCTGCCATA
TCCATCTGCAGGAACAGCAGCTCAATGCCACTGTCACATTGGCAATCATCACAGTG
ACTCCCAAATCCTTTGGGTCACCTGGATCCCTGGGGAAGCTGCTTTGTGAGGTGAC
TCCAGTATCTGGACAAGAACGCTTTGTGTGGAGCTCTCTGGACACCCCATCCCAGA
GGAGTTTCTCAGGACCTTGGCTGGAGGCACAGGAGGCCCAGCTCCTTTCCCAGCC
TTGGCAATGCCAGCTGTACCAGGGGGAGAGGCTTCTTGGAGCAGCAGTGTACTTC
ACAGAGCTGTCTAGCCCAGGTGCCCAACGCTCTGGGAGAGCCCCAGGTGCCCTCC
CAGCAGGCCACCTCCTGCTGTTTCTCATCCTTGGTGTCCTTTCTCTGCTCCTTTTGG
TGACTGGAGCCTTTGGCTTTCACCTTTGGAGAAGACAGTGGCGACCAAGACGATTT
TCTGCCTTAGAGCAAGGGATTCACCCTCCGCAGGCTCAGAGCAAGATAGAGGAGC
TGGAGCAAGAACCGGAGCCGGAGCCGGAGCCGGAACCGGAGCCCGAGCCCGAGC

FIGURE 8 (Continued)

<u>CCGAGCCGGAGCAGCTCTGA</u>CCTGGAGCTGAGGCAGCCAGCAGATCTCAGCAGCCCA
GTCCAAATAAACTCCCTGTCAGCAGCAAAAA

*Homo sapiens* LAG-3 amino acid (SEQ ID NO:6, NCBI Reference Sequence: NP_002277.4):

MWEAQFLGLLFLQPLWVAPVKPLQPGAEVPVVWAQEGAPAQLPCSPTIPLQDLSLLRRAGV
TWQHQPDSGPPAAAPGHPLAPGPHPAAPSSWGPRPRRYTVLSVGPGGLRSGRLPLQPRVQL
DERGRQRGDFSLWLRPARRADAGEYRAAVHLRDRALSCRLRLRLGQASMTASPPGSLRAS
DWVILNCSFSRPDRPASVHWFRNRGQGRVPVRESPHHHLAESFLFLPQVSPMDSGPWGCILT
YRDGFNVSIMYNLTVLGLEPPTPLTVYAGAGSRVGLPCRLPAGVGTRSFLTAKWTPPGGGP
DLLVTGDNGDFTLRLEDVSQAQAGTYTCHIHLQEQQLNATVTLAIITVTPKSFGSPGSLGKL
LCEVTPVSGQERFVWSSLDTPSQRSFSGPWLEAQEAQLLSQPWQCQLYQGERLLGAAVYFT
ELSSPGAQRSGRAPGALPAGHLLLFLILGVLSLLLLVTGAFGFHLWRRQWRPRRFSALEQGI
HPPQAQSKIEELEQEPEPEPEPEPEPEPEPEPEQL

Exemplary Humanized Lag-3 mRNA (SEQ ID NO:7):

GGGCAGTGGGGAGGAGAAGCAGAAGGACTGGGTCTGGAGGAGCAGCTCAAGTTCTAGC
TAGCTGCAGTGGGTTTGCCTGCACTCTGCTCTGGGTCCCAGCCCGGGCCTCTGATCATTA
TCCATCCTGCTGTCTCCAGTCCCCACTCCTGGGGCGTCCTCTTCACCCTACATTCTTTCCC
TCCGCCTCACCTCCTCCTTGTAGAACTTCTCTCTCTCTCTCTCTCTCTCTCTCTCTCT
CTCTCTCTCTGTGTGTGTGTGTGTCTGTCTGTCTGTCTGTCTCTCTCTCCTCCCAGG
ACCTTTTTCTAACCTCCCTTGGAGGGCTGGGGAGGCCCGGGCCATAGAGGAGA**TGAGG
GAGGACCTGCTCCTTGGCTTTTTGCTTCTGGGACTGCTTTGGGAAGCTCCAG**(<u>TGA
AGCCTCTCCAGCCAGGGGCTGAGGTCCCGGTGGTGTGGGCCCAGGAGGGGGCTC
CTGCCCAGCTCCCCTGCAGCCCCACAATCCCCCTCCAGGATCTCAGCCTTCTGCGA
AGAGCAGGGGTCACTTGGCAGCATCAGCCAGACAGTGGCCCGCCCGCTGCCGCCC
CCGGCCATCCCCTGGCCCCGGCCCTCACCCGGCGGCGCCCTCCTCCTGGGGGCC
CAGGCCCCGCCGCTACACGGTGCTGAGCGTGGGTCCCGGAGGCCTGCGCAGCGG
GAGGCTGCCCCTGCAGCCCCGCGTCCAGCTGGATGAGCGCGGCCGGCAGCGCGG
GGACTTCTCGCTATGGCTGCGCCCAGCCCGGCGCGCGGACGCCGGCGAGTACCGC
GCCGCGGTGCACCTCAGGGACCGCGCCCTCTCCTGCCGCCTCCGTCTGCGCCTGG
GCCAGGCCTCGA</u>TGACTGCCAGCCCCCAGGATCTCTCAGAGCCTCCGACTGGGT
CATTTTGAACTGCTCCTTCAGCCGCCCTGACCGCCCAGCCTCTGTGCATTGGTTCC
GGAACCGGGGCCAGGGCCGAGTCCCTGTCCGGGAGTCCCCCCATCACCACTTAGC
GGAAAGCTTCCTCTTCCTGCCCCAAGTCAGCCCCATGGACTCTGGGCCCTGGGGC
TGCATCCTCACCTACAGAGATGGCTTCAACGTCTCCATCATGTATAACCTCACTGT
TCTGG)GTCTGGAGCCCGTAGCCCCTCTGACAGTGTACGCTGCTGAAGGTTCTAGG
GTGGAGCTGCCCTGTCATTTGCCCCAGGAGTGGGGACCCCTTCTTTGCTCATTGC
CAAGTGGACTCCTCCTGGAGGAGGTCCTGAGCTCCCCGTGGCTGGAAAGAGTGGC
AATTTTACCCTTCACCTTGAGGCTGTGGGTCTGGCACAGGCTGGGACCTACACCTG
TAGCATCCATCTGCAGGGACAGCAGCTCAATGCCACTGTCACGTTGGCGGTCATCA
CAGTGACTCCCAAATCCTTCGGGTTACCTGGCTCCGGGGGAAGCTGTTGTGTGA
GGTAACCCCGGCATCTGGAAAGGAAAGATTTGTGTGGCGTCCCCTGAACAATCTG
TCCAGGAGTTGCCCGGGCCCTGTGCTGGAGATTCAGGAGGCCAGGCTCCTTGCTG
AGCGATGGCAGTGTCAGCTGTACGAGGGCCAGAGGCTTCTTGGAGCGACAGTGTA
CGCCGCAGAGTCTAGCTCAGGCGCCCACAGTGCTAGGAGAATCTCAGGTGACCTT
AAAGGAGGCCATCTCGTTCTCGTTCTCATCCTTGGTGCCCTCTCCCTGTTCCTTTT

FIGURE 8 (Continued)

GGTGGCCGGGGCCTTTGGCTTTCACTGGTGGAGAAAACAG<u>TTGCTACTGAGAAGA
TTTTCTGCCTTAGAACATGGGATTCAGCCATTTCCGGCTCAGAGGAAGATAGAGGA
GCTGGAGCGAGAACTGGAGACGGAGATGGGACAGGAGCCGGAGCCCGAGCCGGA
GCCACAGCTGGAGCCAGAGCCCAGGCAGCTCTGA</u>)CCTGGAGCCGAGGCAGCCAGC
AGGTCTCAGCAGCTCCGCCCGCCCGCCCGCCCGAATAAACTCCCTGTCAGCAGCA
TCAAAAAAAAAAAAAAAAAA

Exemplary Humanized Lag-3 amino acid (SEQ ID NO:8):

MREDLLLGFLLLGLLWEAPV(KPLQPGAEVPVVWAQEGAPAQLPCSPTIPLQDLSLLRRA
GVTWQHQPDSGPPAAAPGHPLAPGPHPAAPSSWGPRPRRYTVLSVGPGGLRSGRLPL
QPRVQLDERGRQRGDFSLWLRPARRADAGEYRAAVHLRDRALSCRLRLRLGQASMT
ASPPGSLRASDWVILNCSFSRPDRPASVHWFRNRGQGRVPVRESPHHHLAESFLFLPQV
SPMDSGPWGCILTYRDGFNVSIMYNLTVL)GLEPVAPLTVYAAEGSRVELPCHLPPGVGTP
SLLIAKWTPPGGGPELPVAGKSGNFTLHLEAVGLAQAGTYTCSIHLQGQQLNATVTLAVITV
TPKSFGLPGSRGKLLCEVTPASGKERFVWRPLNNLSRSCPGPVLEIQEARLLAERWQCQLYE
GQRLLGATVYAAESSSGAHSARRISGDLKGGHL<u>VLVLILGALSLFLLVAGAFGFHWWRKQL
LLRRFSALEHGIQPFPAQRKIEELERELETEMGQEPEPEPEPQLEPEPRQL</u>

Exemplary synthetic DNA fragment for humanization (SEQ ID NO:9; 1,741 bp including exons 2-4
and part of intron 4 of a human *LAG3* gene):

TGAAGCCTCTCCAGCCAGGGGCTGAGGTCCCGGTGGTGTGGGCCCAGGAGGGGGCTCCT
GCCCAGCTCCCCTGCAGCCCCACAATCCCCCTCCAGGATCTCAGCCTTCTGCAAGAGC
AGGGGTCACTTGGCAGCATCAGCCAGACAGGTATGCACCCCAAACTTGGGCAACAGGA
CCTCCGAATCCAGCACTCAACCCCACACCCGTGCCGGTCCTCTGTCCCCTGCCCTGAGGT
GTCACTCCCTCTGAAGCCAGTGACCCAGTCTCCCTGCCCTCGCTTGCACCGTTCCTGCCC
TTGCTCTGCAATCAGCGACCCTCACGCCAGCATCCCTTCTCTCCAGAAGTGGATGCGGC
CAGTCCAACAGAGGGGTCGGGCGTGAGGGGACGGTTGGTGGTCAAGAGAACTCTTGGG
GCGGGCTTTCTCATCCTCAACGGGTGGCTGCCTGCATCCTCCCGGGCTTCCTACCCCTGG
AGCTTCTCAACTCCATTCTCTTTCCCGCCCAGTGGCCCGCCCGCTGCCGCCCCCGGCCAT
CCCCTGGCCCCCGGCCCTCACCCGGCGGCGCCCTCCTCCTGGGGGCCCAGGCCCCGCCG
CTACACGGTGCTGAGCGTGGGTCCCGGAGGCCTGCGCAGCGGGAGGCTGCCCCTGCAG
CCCCGCGTCCAGCTGGATGAGCGCGGCCGGCAGCGCGGGGACTTCTCGCTATGGCTGCG
CCCAGCCCGGCGCGCGGACGCCGGCGAGTACCGCGCCGCGGTGCACCTCAGGGACCGC
GCCCTCTCCTGCCGCCTCCGTCTGCGCCTGGGCCAGGCCTCGAGTATGTGGGCGGGAC
GATGGGAGAAGGGCTGGGAGGTGGGTCCCCATCCCCTGCCTCCCGGGACGCAGGAAGG
GCTGGGGCAGAGGCTGCGCCCTAGGCCCTGTCGGAGAGCTCCCAGAAGAGTAGAGGAA
GGGGGTGGGCGGCCTGCTGGAGTGGAAGGTGCCCCGAAGCACGTGTATGGGGGGCCC
TGTGGAGAGATTGTGTCACCCCCGAGCTCCCCTTCTCCCACCCACGCGGGAGTGCCCAG
AGGGAGGGGAGGGGGGAGAGCATGGGGCTAAAGTGATTCATTTCAGATATCTGTAG
CTCAGGGGGTGGGCTTCGCGGGGTTCCAGGCCAGGAAAACGGCAAGGGTGGCTGATGC
CAAGTAAACTCCAGGCCAGGGACGGGGAAAGTGGTCCTGGGGAGTCTTGGGGATCCAC
TTTATGCACCTCCAGGTGCTGGAAGCTGAGATGGGGAGAGGGTGATGTGGGAGAGGAG
AAGACAAGTCTAAAGCCAGGTGCCTGTTTCCAGGAGCTTCCGGCTTGGCAGCCCTGCTG
TGTTGGGAAATTGTTTCCAGTGGGCTGATGAAGTCTTCTTTATCCTTGCACAGTGACTGC
CAGCCCCCCAGGATCTCTCAGAGCCTCCGACTGGGTCATTTTGAACTGCTCCTTCAGCCG

FIGURE 8 (Continued)

CCCTGACCGCCCAGCCTCTGTGCATTGGTTCCGGAACCGGGGCCAGGGCCGAGTCCCTG
TCCGGGAGTCCCCCCATCACCACTTAGCGGAAAGCTTCCTCTTCCTGCCCCAAGTCAGCC
CCATGGACTCTGGGCCCTGGGGCTGCATCCTCACCTACAGAGATGGCTTCAACGTCTCC
ATCATGTATAACCTCACTGTTCTGGGTAACTCCCCCACTCTGCTTCACATTTGACCACAA
CTCCTTCCTGCCCCCCTTGTCACCTCCCCTAAC

Exemplary humanized Lag3 allele including a selection cassette (SEQ ID NO:10; human sequence indicated in bold uppercase font, selection cassette sequence indicated in lowercase font, and mouse sequence indicated by regular uppercase font):

TGAAGCCTCTCCAGCCAGGGGCTGAGGTCCCGGTGGTGTGGGCCCAGGAGGGGG
CTCCTGCCCAGCTCCCCTGCAGCCCCACAATCCCCCTCCAGGATCTCAGCCTTCTG
CGAAGAGCAGGGGTCACTTGGCAGCATCAGCCAGACAGGTATGCACCCCAAACTT
GGGCAACAGGACCTCCGAATCCAGCACTCAACCCCACACCCGTGCCGGTCCTCTG
TCCCCTGCCCTGAGGTGTCACTCCCTCTGAAGCCAGTGACCCAGTCTCCTGCCCT
CGCTTGCACCGTTCCTGCCCTTGCTCTGCAATCAGCGACCCTCACGCCAGCATCCC
TTCTCTCCAGAAGTGGATGCGGCCAGTCCAACAGAGGGGTCGGGCGTGAGGGGAC
GGTTGGTGGTCAAGAGAACTCTTGGGGCGGGCTTTCTCATCCTCAACGGGTGGCT
GCCTGCATCCTCCCGGGCTTCCTACCCCTGGAGCTTCTCAACTCCATTCTCTTTCC
CGCCCAGTGGCCCGCCCGCTGCCGCCCCGGCCATCCCCTGGCCCCGGCCCTCA
CCCGGCGGCGCCCTCCTCCTGGGGGCCCAGGCCCCGCCGCTACACGGTGCTGAGC
GTGGGTCCCGGAGGCCTGCGCAGCGGGAGGCTGCCCCTGCAGCCCCGCGTCCAG
CTGGATGAGCGCGGCCGGCAGCGCGGGGACTTCTCGCTATGGCTGCGCCCAGCCC
GGCGCGCGGACGCCGGCGAGTACCGCGCCGCGGTGCACCTCAGGGACCGCGCCC
TCTCCTGCCGCCTCCGTCTGCGCCTGGGCCAGGCCTCGAGTATGTGGGCGGGAC
GATGGGAGAAGGGCTGGGAGGTGGGTCCCATCCCCTGCCTCCCGGGACGCAGG
AAGGGCTGGGGCAGAGGCTGCGCCCTAGGCCCTGTCGGAGAGCTCCCAGAAGAGT
AGAGGAAGGGGGTGGGCGGCCTGCTGGAGTGGAAGGTGCCCCGAAGCACGTGT
ATGGGGGGCCCTGTGGAGAGATTGTGTCACCCCCGAGCTCCCCTTCTCCCACCCA
CGCGGGAGTGCCCAGAGGGAGGGGGAGGGGGGGAGAGCATGGGGCTAAAGTGAT
TCATTTCAGATATCTGTAGCTCAGGGGGTGGGCTTCGCGGGGTTCCAGGCCAGGA
AAACGGCAAGGGTGGCTGATGCCAAGTAAACTCCAGGCCAGGGACGGGGAAAGTG
GTCCTGGGGAGTCTTGGGGATCCACTTTATGCACCTCCAGGTGCTGGAAGCTGAG
ATGGGGAGAGGGTGATGTGGGAGAGGAGAAGACAAGTCTAAAGCCAGGTGCCTGT
TTCCAGGAGCTTCCGGCTTGGCAGCCCTGCTGTGTTGGGAAATTGTTTCCAGTGGG
CTGATGAAGTCTTCTTTATCCTTGCACAGTGACTGCCAGCCCCCAGGATCTCTCA
GAGCCTCCGACTGGGTCATTTTGAACTGCTCCTTCAGCCGCCCTGACCGCCCAGCC
TCTGTGCATTGGTTCCGGAACCGGGGCCAGGGCCGAGTCCCTGTCCGGGAGTCCC
CCCATCACCACTTAGCGGAAAGCTTCCTCTTCCTGCCCCAAGTCAGCCCCATGGAC
TCTGGGCCCTGGGGCTGCATCCTCACCTACAGAGATGGCTTCAACGTCTCCATCAT
GTATAACCTCACTGTTCTGGGTAACTCCCCCACTCTGCTTCACATTTGACCACAAC
TCCTTCCTGCCCCCCTTGTCACCTCCCCTAACgtcgagataacttcgtataatgtatgctatacgaagttatatgc
atggcctccgcgccgggttttggcgcctcccgcgggcgccccctcctcacggcgagcgctgccacgtcagacgaagggcgcagcgagcgt
cctgatccttccgccggacgctcaggacagcggcccgctgctcataagactcggccttagaaccccagtatcagcagaaggacatttaggac
gggacttgggtgactctagggcactggttttctttccagagagcggaacaggcgaggaaaagtagtcccttctcggcgattctgcggagggatct
ccgtggggcggtgaacgccgatgattatataaggacgcgccgggtgtggcacagctagttccgtcgcagccgggatttgggtcgcggttcttgtt
tgtggatcgctgtgatcgtcacttggtgagtagcgggctgctgggctggccggggctttcgtggccgccgggccgctcggtgggacggaagcg

FIGURE 8 (Continued)

tgtggagagaccgccaagggctgtagtctgggtccgcgagcaaggttgccctgaactggggttggggggagcgcagcaaaatggcggctgt
tcccgagtcttgaatggaagacgcttgtgaggcgggctgtgaggtcgttgaaacaaggtgggggggcatggtgggcggcaagaacccaaggtct
tgaggccttcgctaatgcgggaaagctcttattcgggtgagatggctgggggcaccatctggggacccctgacgtgaagtttgtcactgactggag
aactcggtttgtcgtctgttgcggggggcggcagttatggcggtgccgttgggcagtgcacccgtacctttgggagcgcgcgccctcgtcgtgtcgt
gacgtcacccgttctgttggcttataatgcaggggtggggccacctgccggtaggtgtgcggtaggcttttctccgtcgcaggacgcagggttcgg
gcctagggtaggctctcctgaatcgacaggcgccggacctctggtgaggggagggataagtgaggcgtcagtttctttggtcggttttatgtacct
atcttcttaagtagctgaagctccggttttgaactatgcgctcggggttggcgagtgtgttttgtgaagttttttaggcaccttttgaaatgtaatcatttg
ggtcaatatgtaattttcagtgttagactagtaaattgtccgctaaattctggccgttttggctttttgttagacgtgttgacaattaatcatcggcatagt
atatcggcatagtataatacgacaaggtgaggaactaaaccatgggatcggccattgaacaagatggattgcacgcaggttctccggccgcttgg
gtggagaggctattcggctatgactgggcacaacagacaatcggctgctctgatgccgccgtgttccggctgtcagcgcagggggcgccggttc
tttttgtcaagaccgacctgtccggtgccctgaatgaactgcaggacgaggcagcgcggctatcgtggctggccacgacgggcgttccttgcgc
agctgtgctcgacgttgtcactgaagcgggaagggactggctgctattgggcgaagtgccggggcaggatctcctgtcatctcaccttgctcctg
ccgagaaagtatccatcatggctgatgcaatgcggcggctgcatacgcttgatccggctacctgcccattcgaccaccaagcgaaacatcgcatc
gagcgagcacgtactcggatggaagccggtcttgtcgatcaggatgatctggacgaagagcatcagggggctcgcgccagccgaactgttcgcc
aggctcaaggcgcgcatgcccgacggcgatgatctcgtcgtgacccatgcgatgcctgcttgccgaatatcatggtggaaaatggccgcttttc
tggattcatcgactgtggccggctgggtgtggcggaccgctatcaggacatagcgttggctaccgtgatattgctgaagagcttggcggcgaat
gggctgaccgcttcctcgtgctttacggtatcgccgctcccgattcgcagcgcatcgccttctatcgccttcttgacgagttcttctgaggggatcg
ctgtaagtctgcagaaattgatgatctattaaacaataaagatgtccactaaaatggaagttttttcctgtcatactttgttaagaagggtgagaacaga
gtacctacattttgaatggaaggattggagctacggggggtggggggtggggtgggattagataaatgcctgctctttactgaaggctctttactattgc
tttatgataatgtttcatagttggatatcataattttaaacaagcaaaaccaaattaagggccagctcattcctcccactcatgatctatagatctatagatc
tctcgtgggatcattgttttctcttgattcccactttgtggttctaagtactgtggttccaaatgtgtcagtttcatagcctgaagaacgagatcagcag
cctctgttccacatacacttcattctcagtattgttttgccaagttctaattccatcagacctcgacctgcagcccctagcccgggcgccagtagcagc
acccacgtccaccttctgtctagtaatgtccaacacctccctcagtccaaacactgctctgcatccatgtggctcccatttatacctgaagcacttgat
ggggcctcaatgttttactagagcccaccccctgcaactctgagaccctctggatttgtctgtcagtgcctcactggggcgttggataatttcttaaa
aggtcaagttccctcagcagcattctctgagcagtctgaagatgtgtgcttttcacagttcaaatccatgtggctgtttcacccacctgcctggccttg
ggttatctatcaggacctagcctagaagcaggtgtgtggcacttaacacctaagctgagtgactaactgaacactcaagtggatgccatctttgtca
cttcttgactgtgacacaagcaactcctgatgccaaagccctgcccacccctctcatgcccatatttggacatggtacaggtcctcactggccatggt
ctgtgaggtcctggtcctctttgacttcataattcctagggggccactagtatctataagaggaagagggtgctggctccaggccacagcccacaa
aattccacctgctcacaggttggctggctcgacccaggtggtgtccctgctctgagccagctcccggccaagccagcaccatgggtaccccca
agaagaagaggaaggtgcgtaccgatttaaattccaatttactgaccgtacaccaaaatttgcctgcattaccggtcgatgcaacgagtgatgagg
ttcgcaagaacctgatggacatgttcagggatcgccaggcgtttctgagcatacctggaaaatgcttctgtccgtttgccggtcgtgggcggcatg
gtgcaagttgaataaccggaaatggtttcccgcagaacctgaagatgttcgcgattatcttctatatcttcaggcgcgcggtctggcagtaaaaacta
tccagcaacatttgggccagctaaacatgcttcatcgtcggtccgggctgccacgaccaagtgacagcaatgctgtttcactggttatgcggcgga
tccgaaaagaaaacgttgatgccggtgaacgtgcaaaacaggctctagcgttcgaacgcactgatttcgaccaggttcgttcactcatggaaata
gtgatcgctgccaggatatacgtaatctggcatttctggggattgcttataacaccctgttacgtatagccgaaattgccaggatcagggttaaagat
atctcacgtactgacggtgggagaatgttaatccatattggcagaacgaaaacgctggttagcaccgcaggtgtagagaaggcacttagcctggg
ggtaactaaactggtcgagcgatggatttccgtctctggtgtagctgatgatccgaataacatcctgttttgccgggtcagaaaaaatggtgttgccg
cgccatctgccaccagccagctatcaactcgcgccctgaagggattttgaagcaactcatcgattgatttacggcgctaaggtaaatataaaattt
ttaagtgtataatgtgttaaactactgattctaattgtttgtgtattttaggatgactctggtcagagatacctggcctggtctggacacagtgcccgtgtc
ggagccgcgcgagatatggcccgcgctggagtttcaataccggagatcatgcaagctggtggctggaccaatgtaaatattgtcatgaactatatc
cgtaacctggatagtgaaacaggggcaatggtgcgcctgctggaagatggcgattgatctagataagtaatgatcataatcagccatatcacatct
gtagaggttttacttgctttaaaaaacctcccacacctcccctgaacctgaaacataaaatgaatgcaattgttgttgttaaacctgccctagttgcgg
ccaattccagctgagcgtgcctccgcaccattaccagttggtctggtgtcaaaaataataatacccggcagggggggatctaagctctagataagt
aatgatcataatcagccatatcacatctgtagaggttttacttgctttaaaaaacctcccacacctcccctgaacctgaaacataaaatgaatgcaatt
gttgttgttaacttgttattgcagcttataatggttacaaataaagcaatagcatcacaaatttcacaaataaagcatttttttcactgcattctagttgtgg
tttgtccaaactcatcaatgtatcttatcatgtctggaataacttcgtataatgtatgctatacgaagttatgctagtaactataacggtcctaaggtagcg
agctagcGACCCCCAAAACTTTCTCAGCTGCGTGTGGTCTCACTCCACATCACTTTGTTTCAG
TGTCCAAACCATTTTCTCTCTGGGCATCTTTTAGCTGCTGTCTCTCTTACTTTTATTTATTT

FIGURE 8 (Continued)

ATTTGTGTGTTTATTTATTTATTTTCATTTTAGCGTGCGTTGGTGTTTTGCCTGCATAGAT
GTCTGTGTCAGGGTATTGGATTCCCTGGAACTTGACCTACAGACAGTCATGAGATACCA
TATGGGTGCTGGGAATTGAACCCAGCTCCTCTGGAAGGACAGCCAGTGTTCTAATCTGC
CATCTCTCACTGTTTATCCCTTGGCTGTTCAGCCTCCTGAGCCTTTGGTCTCTTGCTGCCT
CAGTTTCCCTAGTTTCTCTGCTTTGCTCTGTTTCTTTCTGTGTTACAGCCAAATGCCTCCT
TCCCCCTTCTGCCTTACTTCCTTGATGTCTCCACCCTCTGGCCCACTGCTTACCCTTGGTA
ACGGCTTGGCTTTTCCTTCTTCTCTCCAGGTCTGGAGCCCGTAGCCCTCTGACAGTGTA
CGCTGCTGAAGGTTCTAGGGTGGAGCTGCCCTGTCATTTGCCCCAGGAGTGGGGACCC
CTTCTTTGCTCATTGCCAAGTGGACTCCTCCTGGAGGAGGTCCTGAGCTCCCCGTGGCTG
GAAAGAGTGGCAATTTTACCCTTCACCTTGAGGCTGTGGGTCTGGCACAGGCTGGGACC
TACACCTGTAGCATCCATCTGCAGGGACAGCAGCTCAATGCCACTGTCACGTTGGCGGT
CATCACAG

Humanized Lag3 allele after recombinase-mediated excision of a selection cassette (SEQ ID NO:11; human sequence indicated in bold uppercase font, remaining sequence after recombinase-mediated deletion of a selection cassette indicated in lowercase font, and mouse sequence indicated by regular uppercase font):

**CCATCACTTTGTATAAGGGCAGATCCCAAAGCTGCCTCAGCCTCCCTTCAACAGGG
AGGCATGATGTTTCTTTCTTAGGAAAGCCAGGGCATTTCTCTATTCTCCAATCTCTT
GGCTCAATGCCCTTGGCCTCTCTTTTGTTCCACTAGTGAAGCCTCTCCAGCCAGGG
GCTGAGGTCCCGGTGGTGTGGGCCCAGGAGGGGGCTCCTGCCCAGCTCCCCTGCA
GCCCCACAATCCCCCTCCAGGATCTCAGCCTTCTGCGAAGAGCAGGGGTCACTTG
GCAGCATCAGCCAGACAGGTATGCACCCCAAACTTGGGCAACAGGACCTCCGAAT
CCAGCACTCAACCCCACACCCGTGCCGGTCCTCTGTCCCCTGCCCTGAGGTGTCAC
TCCCTCTGAAGCCAGTGACCCAGTCTCCCTGCCCTCGCTTGCACCGTTCCTGCCCT
TGCTCTGCAATCAGCGACCCTCACGCCAGCATCCCTTCTCTCCAGAAGTGGATGCG
GCCAGTCCAACAGAGGGGTCGGGCGTGAGGGGACGGTTGGTGGTCAAGAGAACT
CTTGGGGCGGGCTTTCTCATCCTCAACGGGTGGCTGCCTGCATCCTCCCGGGCTTC
CTACCCCTGGAGCTTCTCAACTCCATTCTCTTTCCCGCCCAGTGGCCCGCCCGCTG
CCGCCCCCGGCCATCCCCTGGCCCCCGGCCCTCACCCGGCGGCGCCCTCCTCCTG
GGGGCCCAGGCCCCGCCGCTACACGGTGCTGAGCGTGGGTCCCGGAGGCCTGCG
CAGCGGGAGGCTGCCCCTGCAGCCCCGCGTCCAGCTGGATGAGCGCGGCCGGCA
GCGCGGGGACTTCTCGCTATGGCTGCGCCCAGCCCGGCGCGCGGACGCCGGCGA
GTACCGCGCCGCGGTGCACCTCAGGGACCGCGCCCTCTCCTGCCGCCTCCGTCTG
CGCCTGGGCCAGGCCTCGAGTATGTGGGGCGGGACGATGGGAGAAGGGCTGGGA
GGTGGGTCCCCATCCCCTGCCTCCCGGGACGCAGGAAGGGCTGGGGCAGAGGCT
GCGCCCTAGGCCCTGTCGGAGAGCTCCCAGAAGAGTAGAGGAAGGGGGTGGGCG
GCCTGCTGGAGTGGAAGGTGCCCCGAAGCACGTGTATGGGGGCCCTGTGGAGA
GATTGTGTCACCCCCGAGCTCCCCTTCTCCCACCCACGCGGGAGTGCCCAGAGGG
AGGGGGAGGGGGGAGAGCATGGGGCTAAAGTGATTCATTTCAGATATCTGTAGC
TCAGGGGGTGGGCTTCGCGGGGTTCCAGGCCAGGAAAACGGCAAGGGTGGCTGA
TGCCAAGTAAACTCCAGGCCAGGGACGGGGAAAGTGGTCCTGGGGAGTCTTGGGG
ATCCACTTTATGCACCTCCAGGTGCTGGAAGCTGAGATGGGGAGAGGGTGATGTG
GGAGAGGAGAAGACAAGTCTAAAGCCAGGTGCCTGTTTCCAGGAGCTTCCGGCTT
GGCAGCCCTGCTGTGTTGGGAAATTGTTTCCAGTGGGCTGATGAAGTCTTCTTTAT
CCTTGCACAGTGACTGCCAGCCCCCAGGATCTCTCAGAGCCTCCGACTGGGTCAT**

FIGURE 8 (Continued)

TTTGAACTGCTCCTTCAGCCGCCCTGACCGCCCAGCCTCTGTGCATTGGTTCCGGA
ACCGGGGCCAGGGCCGAGTCCCTGTCCGGGAGTCCCCCCATCACCACTTAGCGGA
AAGCTTCCTCTTCCTGCCCCAAGTCAGCCCCATGGACTCTGGGCCCTGGGGCTGCA
TCCTCACCTACAGAGATGGCTTCAACGTCTCCATCATGTATAACCTCACTGTTCTG
GGTAACTCCCCCACTCTGCTTCACATTTGACCACAACTCCTTCCTGCCCCCCTTGT
CACCTCCCCTAACgtcgagataacttcgtataatgtatgctatacgaagttatgctagtaactataacggtcctaaggtagcgagctag
cGACCCCCAAAACTTTCTCAGCTGCGTGTGGTCTCACTCCACATCACTTTGTTTCAGTGTC
CAAACCATTTTCTCTCTGGGCATCTTTTAGCTGCTGTCTCTCTTACTTTTATTTATTTATTT
GTGTGTTTATTTATTTATTTTCATTTTAGCGTGCGTTGGTGTTTTGCCTGCATAGATGTCT
GTGTCAGGGTATTGGATTCCCTGGAACTTGACCTACAGACAGTCATGAGATACCATATG
GGTGCTGGGAATTGAACCCAGCTCCTCTGGAAGGACAGCCAGTGTTCTAATCTGCCATC
TCTCACTGTTTATCCCTTGGCTGT

FIGURE 9A

(CATGATGTTT CTTTCTTAGG AAAGCCAGGG CATTTCTCTA TTCTCCAATC TCTTGGCTCA ATGCCCTTGG CCTCTCTTTT GTTCCACTAG) TGAAGCCTCT CCAGCCAGGG GCTGAGGTC CCGGTGGTG TGGGCCAG GAGGGGGCTC CTGCCCAGCT CCC (SEQ ID NO:12)

FIGURE 9B

TTCACATTTG ACCACAACTC CTTCCTGCCC CCCTTGTCAC CTCCCCTAAC (*GTCGAG* ATAACTTCG TATAATGTAT GCTATACGAA GTTAT ATGCATGCC TCCGCGCCGG GTTTGGCGC CTCCCGCGG CGCCCCCCTC CTCACGGGGA GCGCTGCCAC GTCAGAGCGAA GGGCGCAGCG AGCGTCCTGA) (SEQ ID NO:13)

FIGURE 9C

(TTTCACTGCAT TCTAGTTGTG GTTTGTCCAA ACTCATCAAT GTATCTTATC ATGTCTGGA ATAACTTCGT ATAATGTATG CTATACGAAG TTAT GCTAGTAACT ATAACGGTCC TAAGGTAGCG A *GCTAGC*) GACCCCCAAA ACTTCTCAG CTGCGTGTGG TCTCACTCCA CATCACTTTG TTTCAGTGTC CAAACCATTT TCTCTCTGGG CATCTTTTAG (SEQ ID NO:14)

FIGURE 9D

ACGTCTCCAT CATGTATAAC CTCACTGTTC TGGGTAAACT CCCCCACTCT GCTTCACATT TGACCACAAC TCCTTCCTGC CCCCCTGTC ACCTCCCCT AAC (*GTCGAG* ATAACTTCGTA TAATGTATGC TATACGAAGT TAT GCTAGTA ACTATAACGG TCCTAAGGTA GCGA *GCTAGC*) GACCCCCAAA ACTTTCTCAG CTGCGTGTGG TCTCACTCCA CATCACTTTG TTTCAGTGTC CAAACCATTT TCTCTCTGG GCATCTTTTA GCTGCTGTCTC (SEQ ID NO:15)

SEQUENCE LISTING

```
<160> NUMBER OF SEQ ID NOS: 27

<210> SEQ ID NO 1
<211> LENGTH: 1817
<212> TYPE: DNA
<213> ORGANISM: Rattus norvegicus

<400> SEQUENCE: 1
acattctttg cctcacctcc ctccttgtgg aatttctctc tctctctctc tttttttttt      60
ctcccaggac cttttctga actcccttgc agggcctgtg aagcccgggg gccacagagg      120
agatgaggca ggatctgttc cttgacctttt tgcttctgca gctgctttgg gaagctccag     180
ttgtgtcttc agggcctggg aaagagctct ccgtggtgtg ggcccaggag ggagctcctg     240
tccatcttcc ctgcagcctc gaatttcccc acctggatcc caacttttctg cgaagaggat    300 gggtcacctg gcaacatcga ccagacagtg accaacccgc ttccatcccg gcccttgacc    360
ttctccaggg aatgccctcg actaggagac acccacccca tcgctacacg gtgctgagtg    420
tggctccagg aggcctgcgc agcgggaggc agccctgct atcccacgtg cagctggaga    480
agcgtggccc ccagcgcggg gacttctctc tgtggttgcg cccagctacg cgcaaagatg    540
cgggcgagta ccacgccttc gtgcgcctcc cggaccgcga cttctcctgc agcctccgcc    600
tgcgcgtcgg ccaggcctcg atgattgcca gtcccccagg aaccctcaag ccgtctgatt    660
gggtcatttt gaactgctcc ttcagtcgtc ctgaccgccc agtctctgtg cactggttcc   720
agggccaaag ccgagtgccc gtccacaatt caccccgtca ttatctagct gaaagtttcc    780
tcttactgcc ccaagtcagc ccactggatt ccgggacctg gggctgtgtc ctcacctaca    840
gagatggctt caatgtctcc atcacgtaca acctcaaggt tcagggtctg gaacctgtag    900
cccctttgac agtgtacgct gctgaaggtt ctagggtgga gctgccctgt cacttgcctc    960
ccgttgtggg gaccccttct ttgctcattg ccaagtggac tcctcctggg ggaggtcctg   1020
agctcccggt gactggaaag agtggcaatt ttaccctttca acttgagaat gtgggtcggg   1080
cacaggctgg gacctacacc tgcagcatcc atctgcaggg gcggcagctc agtgcggctg    1140
tgacgttggc agtcatcaca gtgactccta aatccttcgg gttacctggc tccccgcaga   1200
```

-continued

```
agctgttatg tgaggtagtc ccggcatctg gagaaggaag atttgtgtgg cgcccctca   1260 gcgatctgtc caggagttcc ctgggccctg tgctggagtt gcaggaggcc aagcttctgg   1320
ctgagcaatg gcagtgtcag ctgtatgagg ccagaaact tcttggagca acagtgtaca   1380
ccgcagagtc tagctcaggc gcctggagtg ctaagagaat ctcaggtgac cttaaaggag   1440
gccatctctt cctctctctc atccttggtg cccttgcctt gttcctcttg gtgaccgggg   1500
cctttggctt tcacctgtgg agaagacagt tgctacggag aagatttct gcctttagagc   1560 atgggattcg cccacctccg gttcagagta agatagagga gctggagcga gaaccggaga   1620
ccgagatgga accagagaca gagcccgatc cggagcctca gccggagccc gagctggaac   1680
cagagtccag gcagctctga ccaggagctg agacagccag cagcaggtct cagcagctct   1740
gcccgcccgc ccgcctgccc gcccgccgga ataaactccc tgtcagcagc aaaaaaaaaa   1800
aaaaaaaaaa aaaaaaa                                                  1817
```

<210> SEQ ID NO 2
<211> LENGTH: 525
<212> TYPE: PRT
<213> ORGANISM: Rattus norvegicus

<400> SEQUENCE: 2

```
Met Arg Gln Asp Leu Phe Leu Asp Leu Leu Leu Gln Leu Leu Trp
1               5                   10                  15

Glu Ala Pro Val Ser Ser Gly Pro Gly Lys Glu Leu Ser Val Val
                20                  25                  30

Trp Ala Gln Glu Gly Ala Pro Val His Leu Pro Cys Ser Leu Glu Phe
            35                  40                  45

Pro His Leu Asp Pro Asn Phe Leu Arg Arg Gly Trp Val Thr Trp Gln
        50                  55                  60

His Arg Pro Asp Ser Asp Gln Pro Ala Ser Ile Pro Ala Leu Asp Leu
65                  70                  75                  80

Leu Gln Gly Met Pro Ser Thr Arg Arg His Pro His Arg Tyr Thr
                85                  90                  95

Val Leu Ser Val Ala Pro Gly Gly Leu Arg Ser Gly Arg Gln Pro Leu
            100                 105                 110

Leu Ser His Val Gln Leu Glu Lys Arg Gly Pro Gln Arg Gly Asp Phe
        115                 120                 125

Ser Leu Trp Leu Arg Pro Ala Thr Arg Lys Asp Ala Gly Glu Tyr His
    130                 135                 140

Ala Phe Val Arg Leu Pro Asp Arg Asp Phe Ser Cys Ser Leu Arg Leu
145                 150                 155                 160

Arg Val Gly Gln Ala Ser Met Ile Ala Ser Pro Pro Gly Thr Leu Lys
                165                 170                 175

Pro Ser Asp Trp Val Ile Leu Asn Cys Ser Phe Ser Arg Pro Asp Arg
            180                 185                 190

Pro Val Ser Val His Trp Phe Gln Gly Gln Ser Arg Val Pro Val His
        195                 200                 205

Asn Ser Pro Arg His Tyr Leu Ala Glu Ser Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Gln Gly Leu
                245                 250                 255

Glu Pro Val Ala Pro Leu Thr Val Tyr Ala Ala Glu Gly Ser Arg Val
```

```
                        260                 265                 270
Glu Leu Pro Cys His Leu Pro Pro Val Val Gly Thr Pro Ser Leu Leu
                275                 280                 285

Ile Ala Lys Trp Thr Pro Pro Gly Gly Pro Glu Leu Pro Val Thr
        290                 295                 300

Gly Lys Ser Gly Asn Phe Thr Leu Gln Leu Glu Asn Val Gly Arg Ala
305                 310                 315                 320

Gln Ala Gly Thr Tyr Thr Cys Ser Ile His Leu Gln Gly Arg Gln Leu
                325                 330                 335

Ser Ala Ala Val Thr Leu Ala Val Ile Thr Val Thr Pro Lys Ser Phe
                340                 345                 350

Gly Leu Pro Gly Ser Pro Gln Lys Leu Leu Cys Glu Val Val Pro Ala
                355                 360                 365

Ser Gly Glu Gly Arg Phe Val Trp Arg Pro Leu Ser Asp Leu Ser Arg
                370                 375                 380

Ser Ser Leu Gly Pro Val Leu Glu Leu Gln Glu Ala Lys Leu Leu Ala
385                 390                 395                 400

Glu Gln Trp Gln Cys Gln Leu Tyr Glu Gly Gln Lys Leu Leu Gly Ala
                405                 410                 415

Thr Val Tyr Thr Ala Glu Ser Ser Gly Ala Trp Ser Ala Lys Arg
                420                 425                 430

Ile Ser Gly Asp Leu Lys Gly Gly His Leu Phe Leu Ser Leu Ile Leu
                435                 440                 445

Gly Ala Leu Ala Leu Phe Leu Leu Val Thr Gly Ala Phe Gly Phe His
    450                 455                 460

Leu Trp Arg Arg Gln Leu Leu Arg Arg Arg Phe Ser Ala Leu Glu His
465                 470                 475                 480

Gly Ile Arg Pro Pro Val Gln Ser Lys Ile Glu Glu Leu Glu Arg
                485                 490                 495

Glu Pro Glu Thr Glu Met Glu Pro Glu Thr Glu Pro Asp Pro Glu Pro
                500                 505                 510

Gln Pro Glu Pro Glu Leu Glu Pro Glu Ser Arg Gln Leu
                515                 520                 525

<210> SEQ ID NO 3
<211> LENGTH: 2020
<212> TYPE: DNA
<213> ORGANISM: Mus musculus

<400> SEQUENCE: 3
gggcagtggg gaggagaagc agaaggactg ggtctggagg agcagctcaa gttctagcta    60
gctgcagtgg gtttgcctgc actctgctct gggtcccagc ccgggcctct gatcattatc   120
catcctgctg tctccagtcc ccactcctgg ggcgtcctct tcaccctaca ttctttccct   180
ccgcctcacc tcctccttgt agaacttctc tctctctctc tctctctctc tctctctctc   240
tctctctctc tctgtgtgtg tgtgtgtgtc tgtctgtctg tctgtctctc tctcctccca   300 ggacctttt ctaacctccc ttggagggct ggggaggccc gggccataga ggagatgagg    360
gaggacctgc tccttggctt tttgcttctg ggactgcttt ggaagctcc agttgtgtct    420 tcagggcctg ggaaagagct cccgtggtg tgggcccagg agggagctcc cgtccatctt   480
ccctgcagcc tcaaatcccc caacctggat cctaactttc tacgaagagg agggggttatc   540 tggcaacatc aaccgacag tggccaaccc actcccatcc cggcccttga ccttcaccag   600
gggatgccct cgcctagaca acccgcaccc ggtcgctaca cggtgctgag cgtggctcca   660
```

```
ggaggcctgc gcagcgggag gcagcccctg catccccacg tgcagctgga ggagcgcggc      720
ctccagcgcg gggacttctc tctgtggttg cgcccagctc tgcgcaccga tgcgggcgag      780
taccacgcca ccgtgcgcct cccgaaccgc gccctctcct gcagtctccg cctgcgcgtc      840
ggccaggcct cgatgattgc tagtccctca ggagtcctca agctgtctga ttgggtcctt      900
ttgaactgct ccttcagccg tcctgaccgc ccagtctctg tgcactggtt ccagggccag      960
aaccgagtgc ctgtctacaa ctcaccgcgt cattttttag ctgaaacttt cctgttactg     1020
ccccaagtca gcccctggac tctgggacc tggggctgtg tcctcaccta cagagatggc     1080
ttcaatgtct ccatcacgta caacctcaag gttctgggtc tggagcccgt agcccctctg     1140
acagtgtacg ctgctgaagg ttctagggtg gagctgccct gtcatttgcc cccaggagtg     1200 gggaccccctt ctttgctcat tgccaagtgg actcctcctg gaggaggtcc tgagctcccc     1260
gtggctggaa agagtggcaa ttttacccctt caccttgagg ctgtgggtct ggcacaggct     1320
gggacctaca cctgtagcat ccatctgcag ggacagcagc tcaatgccac tgtcacgttg     1380
gcggtcatca cagtgactcc caaatccttc gggttacctg gctcccgggg aagctgttg      1440 tgtgaggtaa ccccggcatc tggaaaggaa agatttgtgt ggcgtcccct gaacaatctg     1500
tccaggagtt gcccgggccc tgtgctggag attcaggagg ccaggctcct tgctgagcga     1560
tggcagtgtc agctgtacga gggccagagg cttcttggag cgacagtgta cgccgcagag     1620
tctagctcag gcgcccacag tgctaggaga atctcaggtg accttaaagg aggccatctc     1680
gttctcgttc tcatccttgg tgccctctcc ctgttccttt tggtggccgg ggcctttggc     1740
tttcactggt ggagaaaaca gttgctactg agaagatttt ctgccttaga acatgggatt     1800
cagccatttc cggctcagag gaagatagag gagctggagc gagaactgga gacggagatg     1860 gggacaggagc cggagcccga gccggagcca cagctggagc cagagcccag gcagctctga     1920
cctggagccg aggcagccag caggtctcag cagctccgcc cgcccgcccg cccgcccgaa     1980 taaaactccct gtcagcagca tcaaaaaaaa aaaaaaaaa                           2020
```

<210> SEQ ID NO 4
<211> LENGTH: 521
<212> TYPE: PRT
<213> ORGANISM: Mus musculus

<400> SEQUENCE: 4

```
Met Arg Glu Asp Leu Leu Gly Phe Leu Leu Gly Leu Leu Trp
1               5                   10                  15

Glu Ala Pro Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125
```

```
Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Gly Ala His Ser Ala Arg Arg
            420                 425                 430

Ile Ser Gly Asp Leu Lys Gly Gly His Leu Val Leu Val Leu Ile Leu
        435                 440                 445

Gly Ala Leu Ser Leu Phe Leu Leu Val Ala Gly Ala Phe Gly Phe His
450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
                485                 490                 495

Glu Leu Glu Thr Glu Met Gly Gln Glu Pro Glu Pro Glu Pro
            500                 505                 510

Gln Leu Glu Pro Glu Pro Arg Gln Leu
        515                 520

<210> SEQ ID NO 5
<211> LENGTH: 1995
<212> TYPE: DNA
```

<213> ORGANISM: Homo sapiens

<400> SEQUENCE: 5

| | | | | | |
|---|---|---|---|---|---|
| acagggtga | aggcccagag | accagcagaa | cggcatccca | gccacgacgg | ccactttgct | 60 |
| ctgtctgctc | tccgccacgg | ccctgctctg | ttccctggga | caccccgcc | cccacctcct | 120 |
| caggctgcct | gatctgccca | gctttccagc | tttcctctgg | attccggcct | ctggtcatcc | 180 |
| ctccccaccc | tctctccaag | gccctctcct | ggtctccctt | cttctagaac | ccttcctcc | 240 |
| acctccctct | ctgcagaact | tctccttac | ccccacccc | ccaccactgc | ccctttcct | 300 |
| tttctgacct | ccttttggag | ggctcagcgc | tgcccagacc | ataggagaga | tgtgggaggc | 360 |
| tcagttcctg | ggcttgctgt | ttctgcagcc | gctttgggtg | gctccagtga | agcctctcca | 420 |
| gccaggggct | gaggtcccgg | tggtgtgggc | ccaggagggg | gctcctgccc | agctcccctg | 480 |
| cagccccaca | atccccctcc | aggatctcag | ccttctgcga | gagcagggg | tcacttggca | 540 |
| gcatcagcca | gacagtggcc | cgcccgctgc | cgccccggc | catccctgg | ccccggccc | 600 |
| tcacccggcg | gcgccctcct | cctggggcc | caggccccgc | cgctacacgg | tgctgagcgt | 660 |
| gggtcccgga | ggcctgcgca | gcgggaggct | gcccctgcag | cccgcgtcc | agctggatga | 720 |
| gcgcggccgc | cagcgcgggg | acttctcgct | atggctgcgc | ccagcccggc | gcgcggacgc | 780 |
| cggcgagtac | cgcgccgcgg | tgcacctcag | ggaccgcgcc | ctctcctgcc | gcctccgtct | 840 |
| gcgcctgggc | caggcctcga | tgactgccag | ccccccagga | tctctcagag | cctccgactg | 900 |
| ggtcattttg | aactgctcct | tcagccgccc | tgaccgccca | gcctctgtgc | attggttccg | 960 |
| gaaccggggc | cagggccgag | tccctgtccg | ggagtcccc | catcaccact | tagcggaaag | 1020 |
| cttcctcttc | ctgccccaag | tcagcccat | ggactctggg | ccctggggct | gcatcctcac | 1080 |
| ctacagagat | ggcttcaacg | tctccatcat | gtataacctc | actgttctgg | gtctggagcc | 1140 |
| cccaactccc | ttgacagtgt | acgctggagc | aggttccagg | gtggggctgc | cctgccgcct | 1200 |
| gcctgctggt | gtggggaccc | ggtctttcct | cactgccaag | tggactcctc | ctgggggagg | 1260 |
| ccctgacctc | ctggtgactg | gagacaatgg | cgactttacc | cttcgactag | aggatgtgag | 1320 |
| ccaggcccag | gctgggacct | acacctgcca | tatccatctg | caggaacagc | agctcaatgc | 1380 |
| cactgtcaca | ttggcaatca | tcacagtgac | tcccaaatcc | tttgggtcac | ctggatccct | 1440 |
| ggggaagctg | ctttgtgagg | tgactccagt | atctggacaa | gaacgctttg | tgtgagctc | 1500 |
| tctggacacc | ccatcccaga | ggagtttctc | aggaccttgg | ctggaggcac | aggaggccca | 1560 |
| gctcctttcc | cagccttggc | aatgccagct | gtaccagggg | gagaggcttc | ttggagcagc | 1620 |
| agtgtacttc | acagagctgt | ctagcccagg | tgcccaacgc | tctgggagag | cccaggtgc | 1680 |
| cctcccagca | ggccacctcc | tgctgtttct | catcctggt | gtcctttctc | tgctcctttt | 1740 |
| ggtgactgga | gcctttggct | ttcaccttg | gagaagacag | tggcgaccaa | gacgattttc | 1800 |
| tgccttagag | caagggattc | accctccgca | ggctcagagc | aagatagagg | agctggagca | 1860 |
| agaaccggag | ccggagccgg | agccggaacc | ggagcccgag | cccgagcccg | agccggagca | 1920 |
| gctctgacct | ggagctgagg | cagccagcag | atctcagcag | cccagtccaa | ataaactccc | 1980 |
| tgtcagcagc | aaaaa | | | | | 1995 |

<210> SEQ ID NO 6
<211> LENGTH: 525
<212> TYPE: PRT
<213> ORGANISM: Homo sapiens

<400> SEQUENCE: 6

-continued

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
        370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415
```

```
Gly Glu Arg Leu Leu Gly Ala Ala Val Tyr Phe Thr Glu Leu Ser Ser
                420                 425                 430
Pro Gly Ala Gln Arg Ser Gly Arg Ala Pro Gly Ala Leu Pro Ala Gly
            435                 440                 445
His Leu Leu Leu Phe Leu Ile Leu Gly Val Leu Ser Leu Leu Leu Leu
        450                 455                 460
Val Thr Gly Ala Phe Gly Phe His Leu Trp Arg Arg Gln Trp Arg Pro
465                 470                 475                 480
Arg Arg Phe Ser Ala Leu Glu Gln Gly Ile His Pro Pro Gln Ala Gln
                485                 490                 495
Ser Lys Ile Glu Glu Leu Glu Gln Glu Pro Glu Pro Glu Pro Glu Pro
            500                 505                 510
Glu Pro Glu Pro Glu Pro Glu Pro Glu Pro Glu Gln Leu
        515                 520                 525

<210> SEQ ID NO 7
<211> LENGTH: 2038
<212> TYPE: DNA
<213> ORGANISM: Artificial Sequence
<220> FEATURE:
<223> OTHER INFORMATION: exemplary humanized Lag-3 nucleic acid sequence

<400> SEQUENCE: 7
gggcagtggg gaggagaagc agaaggactg ggtctggagg agcagctcaa gttctagcta      60
gctgcagtgg gtttgcctgc actctgctct ggtcccagcc ccgggcctct gatcattatc     120
catcctgctg tctccagtcc ccactcctgg ggcgtcctct tcaccctaca ttctttccct     180
ccgcctcacc tcctccttgt agaacttctc tctctctctc tctctctctc tctctctctc     240
tctctctctc tctgtgtgtg tgtgtgtgtc tgtctgtctg tctgtctctc tctcctccca     300
ggaccttttt ctaacctccc ttggagggct ggggaggccc gggccataga ggagatgagg     360
gaggacctgc tccttggctt tttgcttctg ggactgcttt gggaagctcc agtgaagcct     420
ctccagccag gggctgaggt cccggtggtg tgggcccagg aggggctcc tgcccagctc      480 ccctgcagcc ccacaatccc cctccaggat ctcagcctc tgcgaagagc agggtcact      540 tggcagcatc agccagacag tggcccgccc gctgccgccc ccggccatcc cctggccccc    600
ggccctcacc cggcggcgcc ctcctcctgg ggcccaggc ccgccgcta cacggtgctg       660 agcgtgggtc ccgaggcct cgcagcggg aggctgcccc tgcagccccg cgtccagctg       720
gatgagcgcg ccggcagcg cggggacttc tcgctatggc tgcgcccagc ccggcgcgcg     780 gacgccggc agtaccgcgc gcggtgcac ctcaggacc gcgccctctc ctgccgcctc       840
cgtctgcgcc tgggccaggc ctcgatgact gccagcccc caggatctct cagagcctcc    900
gactgggtca ttttgaactg ctccttcagc cgccctgacc gcccagcctc tgtgcattgg    960
ttccggaacc ggggccaggg ccgagtccct gtccgggagt cccccatca ccacttagcg    1020 gaaagcttcc tcttcctgcc ccaagtcagc cccatggact ctgggccctg ggctgcatc   1080 ctcacctaca gagatggctt caacgtctcc atcatgtata acctcactgt tctgggtctg   1140
gagcccgtag cccctctgac agtgtacgct gctgaaggtt ctagggtgga gctgccctgt  1200
catttgcccc aggagtgggg gacccccttct ttgctcattg ccaagtggac tcctcctgga   1260
ggaggtcctg agctccccgt ggctggaaag agtggcaatt ttaccccttca ccttgaggct    1320 gtgggtctgg cacaggctgg gacctacacc tgtagcatcc atctgcaggg acagcagctc    1380
aatgccactg tcacgttggc ggtcatcaca gtgactccca atccttcgg gttacctggc    1440
```

-continued

```
tcccggggga agctgttgtg tgaggtaacc ccggcatctg gaaaggaaag atttgtgtgg     1500
cgtcccctga caatctgtc caggagttgc ccggggcctg tgctggagat tcaggaggcc     1560
aggctccttg ctgagcgatg gcagtgtcag ctgtacgagg ccagaggct tcttggagcg     1620 acagtgtacg ccgcagagtc tagctcaggc gcccacagtg ctaggagaat ctcaggtgac     1680
cttaaaggag gccatctcgt tctcgttctc atccttggtg ccctctccct gttccttttg     1740
gtggccgggg cctttggctt tcactggtgg agaaaacagt tgctactgag aagattttct     1800
gccttagaac atgggattca gccatttccg gctcaggaga agatagagga gctggagcga     1860
gaactggaga cggagatggg acaggagccg gagcccgagc cggagccaca gctggagcca     1920
gagcccaggc agctctgacc tggagccgag gcagccagca ggtctcagca gctccgcccg     1980
cccgcccgcc cgcccgaata aactccctgt cagcagcatc aaaaaaaaaa aaaaaaa      2038
```

<210> SEQ ID NO 8
<211> LENGTH: 527
<212> TYPE: PRT
<213> ORGANISM: Artificial Sequence
<220> FEATURE:
<223> OTHER INFORMATION: exemplary humanized Lag-3 amino acid sequence

<400> SEQUENCE: 8

```
Met Arg Glu Asp Leu Leu Leu Gly Phe Leu Leu Leu Gly Leu Leu Trp
1               5                   10                  15

Glu Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Val Ala Pro Leu Thr Val Tyr Ala
```

```
                260                 265                 270
Ala Glu Gly Ser Arg Val Glu Leu Pro Cys His Leu Pro Pro Gly Val
            275                 280                 285
Gly Thr Pro Ser Leu Leu Ile Ala Lys Trp Thr Pro Gly Gly Gly
        290                 295                 300
Pro Glu Leu Pro Val Ala Gly Lys Ser Gly Asn Phe Thr Leu His Leu
305                 310                 315                 320
Glu Ala Val Gly Leu Ala Gln Ala Gly Thr Tyr Thr Cys Ser Ile His
                325                 330                 335
Leu Gln Gly Gln Gln Leu Asn Ala Thr Val Thr Leu Ala Val Ile Thr
            340                 345                 350
Val Thr Pro Lys Ser Phe Gly Leu Pro Gly Ser Arg Gly Lys Leu Leu
            355                 360                 365
Cys Glu Val Thr Pro Ala Ser Gly Lys Glu Arg Phe Val Trp Arg Pro
370                 375                 380
Leu Asn Asn Leu Ser Arg Ser Cys Pro Gly Pro Val Leu Glu Ile Gln
385                 390                 395                 400
Glu Ala Arg Leu Leu Ala Glu Arg Trp Gln Cys Gln Leu Tyr Glu Gly
            405                 410                 415
Gln Arg Leu Leu Gly Ala Thr Val Tyr Ala Ala Glu Ser Ser Ser Gly
            420                 425                 430
Ala His Ser Ala Arg Arg Ile Ser Gly Asp Leu Lys Gly Gly His Leu
            435                 440                 445
Val Leu Val Leu Ile Leu Gly Ala Leu Ser Leu Phe Leu Leu Val Ala
        450                 455                 460
Gly Ala Phe Gly Phe His Trp Trp Arg Lys Gln Leu Leu Leu Arg Arg
465                 470                 475                 480
Phe Ser Ala Leu Glu His Gly Ile Gln Pro Phe Pro Ala Gln Arg Lys
                485                 490                 495
Ile Glu Glu Leu Glu Arg Glu Leu Glu Thr Glu Met Gly Gln Glu Pro
            500                 505                 510
Glu Pro Glu Pro Glu Pro Gln Leu Glu Pro Glu Pro Arg Gln Leu
        515                 520                 525

<210> SEQ ID NO 9
<211> LENGTH: 1741
<212> TYPE: DNA
<213> ORGANISM: Artificial Sequence
<220> FEATURE:
<223> OTHER INFORMATION: exemplary synthetic DNA fragment for
      humanization (1,741 bp including exons 2-4 and part of intron 4 of
      a human LAG3 gene

<400> SEQUENCE: 9
tgaagcctct ccagccaggg gctgaggtcc cggtggtgtg ggcccaggag ggggctcctg      60
cccagctccc ctgcagcccc acaatccccc tccaggatct cagccttctg cgaagagcag    120
gggtcacttg gcagcatcag ccagacaggt atgcacccca acttgggca acaggacctc     180 cgaatccagc actcaacccc acaccgtgc cggtcctctg tccctgccc tgaggtgtca      240 ctccctctga agccagtgac ccagtctccc tgccctcgct tgcaccgttc ctgcccttgc    300
tctgcaatca gcgaccctca cgccagcatc ccttctctcc agaagtggat gcggccagtc    360
caacagaggg gtcgggcgtg aggggacggt tggtggtcaa gagaactctt ggggcgggct    420
ttctcatcct caacgggtgg ctgcctgcat cctcccgggc ttcctacccc tggagcttct    480
caactccatt ctctttcccg cccagtggcc cgcccgctgc cgccccggc catcccctgg     540
```

```
ccccggccc tcacccggcg gcgccctcct cctgggggcc caggccccgc cgctacacgg    600
tgctgagcgt gggtcccgga ggcctgcgca gcgggaggct gccctgcag cccgcgtcc    660 agctggatga gcgcggccgg cagcgcgggg acttctcgct atggctgcgc ccagcccggc    720
gcgcggacgc cggcgagtac cgcgccgcgg tgcacctcag ggaccgcgcc ctctcctgcc    780
gcctccgtct gcgcctgggc caggcctcga gtatgtgggg cgggacgatg ggagaagggc    840
tgggaggtgg gtcccatcc cctgcctccc gggacgcagg aagggctggg gcagaggctg    900
cgccctaggc cctgtcggag agctcccaga agagtagagg aagggggtgg gcggcctgct    960
ggagtggaag gtgcccccga agcacgtgta tgggggccc tgtggagaga ttgtgtcacc   1020
cccgagctcc ccttctccca cccacgcggg agtgcccaga gggaggggga ggggggaga   1080 gcatggggct aaagtgattc atttcagata tctgtagctc agggggtggg cttcgcgggg   1140
ttccaggcca ggaaaacggc aagggtggct gatgccaagt aaactccagg ccagggacgg   1200
ggaaagtggt cctggggagt cttgggggatc cactttatgc acctccaggt gctggaagct   1260
gagatgggga gagggtgatg tgggagagga gaagacaagt ctaaagccag gtgcctgttt   1320
ccaggagctt ccggcttggc agccctgctg tgttgggaaa ttgtttccag tgggctgatg   1380
aagtcttctt tatccttgca cagtgactgc agccccccca ggatctctca gagcctccga   1440
ctgggtcatt ttgaactgct ccttcagccg ccctgaccgc ccagcctctg tgcattggtt   1500
ccggaaccgg ggccagggcc gagtccctgt ccgggagtcc ccccatcacc acttagcgga   1560
aagcttcctc ttcctgcccc aagtcagccc catggactct gggccctggg gctgcatcct   1620
cacctacaga gatggcttca acgtctccat catgtataac ctcactgttc tgggtaactc   1680
ccccactctg cttcacattt gaccacaact ccttcctgcc ccccttgtca cctcccctaa   1740
c                                                                  1741
```

<210> SEQ ID NO 10
<211> LENGTH: 7522
<212> TYPE: DNA
<213> ORGANISM: Artificial Sequence
<220> FEATURE:
<223> OTHER INFORMATION: exemplary humanized Lag3 allele including a
      selection cassette

<400> SEQUENCE: 10

```
tgaagcctct ccagccaggg gctgaggtcc cggtggtgtg ggcccaggag ggggctcctg     60
cccagctccc ctgcagcccc acaatccccc tccaggatct cagccttctg cgaagagcag    120
gggtcacttg gcagcatcag ccagacaggt atgcacccca aacttgggca acaggacctc    180
cgaatccagc actcaacccc acaccgtgc cggtcctctg tcccctgccc tgaggtgtca    240
ctccctctga agccagtgac ccagtctccc tgccctcgct tgcaccgttc ctgcccttgc    300
tctgcaatca gcgaccctca cgccagcatc ccttctctcc agaagtggat gcggccagtc    360
caacagaggg gtcgggcgtg aggggacggt tggtggtcaa gagaactctt ggggcgggct    420
ttctcatcct caacgggtgg ctgcctgcat cctcccgggc ttcctacccc tggagcttct    480
caactccatt ctctttcccg cccagtggcc cgcccgctgc cgcccccggc catccctgg    540 cccccggccc tcacccggcg gcgccctcct cctgggggcc caggccccgc cgctacacgg    600
tgctgagcgt gggtcccgga ggcctgcgca gcgggaggct gccctgcag cccgcgtcc    660 agctggatga gcgcggccgg cagcgcgggg acttctcgct atggctgcgc ccagcccggc    720
gcgcggacgc cggcgagtac cgcgccgcgg tgcacctcag ggaccgcgcc ctctcctgcc    780
```

```
gcctccgtct gcgcctgggc caggcctcga gtatgtgggg cgggacgatg ggagaagggc      840
tgggaggtgg gtccccatcc cctgcctccc gggacgcagg aagggctggg gcagaggctg      900
cgccctaggc cctgtcggag agctcccaga agagtagagg aaggggtgg gcggcctgct       960 ggagtggaag gtgcccccga agcacgtgta tgggggcc   tgtggagaga ttgtgtcacc     1020
cccgagctcc ccttctccca cccacgcggg agtgcccaga gggagggga ggggggaga      1080 gcatggggct aaagtgattc atttcagata tctgtagctc aggggtggg cttcgcgggg     1140 ttccaggcca ggaaaacggc aagggtggct gatgccaagt aaactccagg ccagggacgg     1200
ggaaagtggt cctggggagt cttggggatc cactttatgc acctccaggt gctggaagct     1260
gagatgggga gagggtgatg tgggagagga gaagacaagt ctaaagccag gtgcctgttt     1320
ccaggagctt ccggcttggc agccctgctg tgttgggaaa ttgtttccag tgggctgatg     1380
aagtcttctt tatccttgca cagtgactgc cagccccca  ggatctctca gagcctccga     1440
ctgggtcatt ttgaactgct ccttcagccg ccctgaccgc ccagcctctg tgcattggtt     1500
ccggaaccgg ggccagggcc gagtccctgt ccgggagtcc ccccatcacc acttagcgga     1560
aagcttcctc ttcctgcccc aagtcagccc catggactct gggccctggg gctgcatcct     1620
cacctacaga gatggcttca acgtctccat catgtataac ctcactgttc tgggtaactc     1680
ccccactctg cttcacatttt gaccacaact ccttcctgcc cccttgtca cctccctaa      1740 cgtcgagata acttcgtata atgtatgcta tacgaagtta tatgcatggc ctccgcgccg     1800
ggttttggcg cctcccgcgg gcgcccccct cctcacggcg agcgctgcca cgtcagacga     1860
agggcgcagc gagcgtcctg atccttccgc ccggacgctc aggacagcgg cccgctgctc     1920
ataagactcg gccttagaac cccagtatca gcagaaggac atttttaggac gggacttggg   1980 tgactctagg gcactggttt tctttccaga gagcggaaca ggcgaggaaa agtagtccct    2040
tctcggcgat tctgcggagg gatctccgtg gggcggtgaa cgccgatgat tatataagga     2100
cgcgccgggt gtggcacagc tagttccgtc gcagccggga tttgggtcgc ggttcttgtt     2160
tgtggatcgc tgtgatcgtc acttggtgag tagcgggctg ctgggctggc cggggctttc    2220
gtggccgccg ggccgctcgg tgggacggaa gcgtgtggag agaccgccaa gggctgtagt     2280
ctgggtccgc gagcaaggtt gccctgaact ggggttggg gggagcgcag caaaatggcg      2340
gctgttcccg agtcttgaat ggaagacgct tgtgaggcgg gctgtgaggt cgttgaaaca     2400
aggtgggggg catggtgggc ggcaagaacc caaggtcttg aggccttcgc taatgcggga     2460
aagctcttat tcgggtgaga tgggctgggg caccatctgg ggaccctgac gtgaagtttg     2520
tcactgactg gagaactcgg tttgtcgtct gttgcggggg cggcagttat ggcggtgccg     2580
ttgggcagtg cacccgtacc tttgggagcg cgcgccctcg tcgtgtcgtg acgtcacccg     2640
ttctgttggc ttataatgca gggtggggcc acctgccggt aggtgtgcgg taggcttttc     2700
tccgtcgcag gacgcagggt tcgggcctag ggtaggctct cctgaatcga caggcgccgg     2760
acctctggtg agggaggga taagtgaggc gtcagtttct ttggtcggtt ttatgtacct      2820
atcttcttaa gtagctgaag ctccggtttt gaactatgcg ctcggggttg gcgagtgtgt     2880
tttgtgaagt ttttaggca cctttgaaa tgtaatcatt tgggtcaata tgtaattttc       2940
agtgttagac tagtaaattg tccgctaaat tctggccgtt tttggctttt ttgttagacg    3000
tgttgacaat taatcatcgg catagtatat cggcatagta taatacgaca aggtgaggaa     3060
ctaaaccatg ggatcggcca ttgaacaaga tggattgcac gcaggttctc cggccgcttg     3120
```

```
ggtggagagg ctattcggct atgactgggc acaacagaca atcggctgct ctgatgccgc    3180
cgtgttccgg ctgtcagcgc aggggcgccc ggttcttttt gtcaagaccg acctgtccgg    3240
tgccctgaat gaactgcagg acgaggcagc gcggctatcg tggctggcca cgacgggcgt    3300
tccttgcgca gctgtgctcg acgttgtcac tgaagcggga agggactggc tgctattggg    3360
cgaagtgccg gggcaggatc tcctgtcatc tcaccttgct cctgccgaga agtatccat    3420 catggctgat gcaatgcggc ggctgcatac gcttgatccg gctacctgcc cattcgacca    3480
ccaagcgaaa catcgcatcg agcgagcacg tactcggatg gaagccggtc ttgtcgatca    3540
ggatgatctg gacgaagagc atcagggggct cgcgccagcc gaactgttcg ccaggctcaa    3600
ggcgcgcatg cccgacggcg atgatctcgt cgtgacccat ggcgatgcct gcttgccgaa    3660
tatcatggtg gaaaatggcc gcttttctgg attcatcgac tgtggccggc tgggtgtggc    3720
ggaccgctat caggacatag cgttggctac ccgtgatatt gctgaagagc ttggcggcga    3780
atgggctgac cgcttcctcg tgctttacgg tatcgccgct cccgattcgc agcgcatcgc    3840
cttctatcgc cttcttgacg agttcttctg aggggatccg ctgtaagtct gcagaaattg    3900
atgatctatt aaacaataaa gatgtccact aaaatggaag ttttttcctgt catactttgt    3960 taagaagggg gagaacagag tacctacatt ttgaatggaa ggattggagc tacggggtg    4020 ggggtgggggt gggattagat aaatgcctgc tctttactga aggctcttta ctattgcttt    4080
atgataatgt ttcatagttg gatatcataa tttaaacaag caaaaccaaa ttaagggcca    4140
gctcattcct cccactcatg atctatagat ctatagatct ctcgtgggat cattgttttt    4200
ctcttgattc ccactttgtg gttctaagta ctgtggtttc caaatgtgtc agtttcatag    4260
cctgaagaac gagatcagca gcctctgttc cacatacact tcattctcag tattgttttg    4320
ccaagttcta attccatcag acctcgacct gcagccccta gccgggcgc cagtagcagc    4380 acccacgtcc accttctgtc tagtaatgtc caacacctcc ctcagtccaa acactgctct    4440
gcatccatgt ggctcccatt tatacctgaa gcttgatg gggcctcaat gttttactag    4500
agcccacccc cctgcaactc tgagaccctc tggatttgtc tgtcagtgcc tcactggggc    4560
gttggataat ttcttaaaag gtcaagttcc ctcagcagca ttctctgagc agtctgaaga    4620
tgtgtgcttt tcacagttca atccatgtg gctgtttcac ccacctgcct ggccttgggt    4680
tatctatcag gacctagcct agaagcaggt gtgtggcact aaacacctaa gctgagtgac    4740
taactgaaca ctcaagtgga tgccatcttt gtcacttctt gactgtgaca caagcaactc    4800
ctgatgccaa agccctgccc acccctctca tgcccatatt tggacatggt acaggtcctc    4860
actggccatg gtctgtgagg tcctggtcct ctttgacttc ataattccta ggggccacta    4920
gtatctataa gaggaagagg gtgctggctc ccaggccaca gcccacaaaa ttccacctgc    4980
tcacaggttg gctggctcga cccaggtggt gtccctgct ctgagccagc tcccggccaa    5040
gccagcacca tgggtacccc caagaagaag aggaaggtgc gtaccgattt aaattccaat    5100
ttactgaccg tacaccaaaa tttgcctgca ttaccggtcg atgcaacgag tgatgaggtt    5160
cgcaagaacc tgatggacat gttcagggat cgccaggcgt tttctgagca tacctggaaa    5220
atgcttctgt ccgtttgccg gtcgtgggcg gcatggtgca agttaataa ccggaaatgg    5280 ttttcccgcag aacctgaaga tgttcgcgat tatcttctat atcttcaggc gcgcggtctg    5340
gcagtaaaaa ctatccagca acatttgggc cagctaaaca tgcttcatcg tcggtccggg    5400
ctgccacgac caagtgacag caatgctgtt tcactggtta tgcggcggat ccgaaaagaa    5460
aacgttgatg ccggtgaacg tgcaaaacag gctctagcgt tcgaacgcac tgatttcgac    5520
```

```
caggttcgtt cactcatgga aaatagtgat cgctgccagg atatacgtaa tctggcattt    5580
ctggggattg cttataacac cctgttacgt atagccgaaa ttgccaggat cagggttaaa    5640
gatatctcac gtactgacgg tgggagaatg ttaatccata ttggcagaac gaaaacgctg    5700
gttagcaccg caggtgtaga gaaggcactt agcctggggg taactaaact ggtcgagcga    5760
tggatttccg tctctggtgt agctgatgat ccgaataact acctgttttg ccgggtcaga    5820
aaaaatggtg ttgccgcgcc atctgccacc agccagctat caactcgcgc cctggaaggg    5880 attttttgaag caactcatcg attgatttac ggcgctaagg taaatataaa attttttaagt   5940 gtataatgtg ttaaactact gattctaatt gtttgtgtat tttaggatga ctctggtcag    6000
agatacctgg cctggtctgg acacagtgcc cgtgtcggag ccgcgcgaga tatggcccgc    6060
gctggagttt caataccgga gatcatgcaa gctggtggct ggaccaatgt aaatattgtc    6120
atgaactata tccgtaacct ggatagtgaa acaggggcaa tggtgcgcct gctggaagat    6180
ggcgattgat ctagataagt aatgatcata atcagccata tcacatctgt agaggtttta    6240
cttgctttaa aaaacctccc acacctcccc ctgaacctga acataaaat gaatgcaatt     6300 gttgttgtta aacctgccct agttgcggcc aattccagct gagcgtgcct ccgcaccatt    6360
accagttggt ctggtgtcaa aaataataat aaccgggcag gggggatcta agctctagat    6420
aagtaatgat cataatcagc catatcacat ctgtagaggt tttacttgct ttaaaaaacc    6480
tcccacacct cccctgaac ctgaaacata aatgaatgc aattgttgtt gttaacttgt      6540
ttattgcagc ttataatggt tacaaataaa gcaatagcat cacaaatttc acaaataaag    6600 cattttttttc actgcattct agttgtggtt tgtccaaact catcaatgta tcttatcatg   6660
tctggaataa cttcgtataa tgtatgctat acgaagttat gctagtaact ataacggtcc    6720
taaggtagcg agctagcgac ccccaaaact ttctcagctg cgtgtggtct cactccacat    6780
cactttgttt cagtgtccaa accatttttct ctctgggcat cttttagctg ctgtctctct   6840 tactttttatt tatttatttg tgtgtttatt tatttatttt cattttagcg tgcgttggtg   6900
ttttgcctgc atagatgtct gtgtcagggt attggattcc ctggaacttg acctacagac    6960
agtcatgaga taccatatgg gtgctgggaa ttgaacccag ctcctctgga aggacagcca    7020
gtgttctaat ctgccatctc tcactgttta tcccttggct gttcagcctc ctgagccttt    7080
ggtctcttgc tgcctcagtt tccctagttt ctctgctttg ctctgttttct ttctgtgtta   7140 cagccaaatg cctccttccc ccttctgcct tacttccttg atgtctccac cctctggccc    7200
actgcttacc cttggtaacg gcttggcttt tccttcttct ctccaggtct ggagcccgta    7260 gccctctga cagtgtacgc tgctgaaggt tctagggtgg agctgccctg tcatttgccc     7320
ccaggagtgg ggacccttc tttgctcatt gccaagtgga ctcctcctgg aggaggtcct    7380
gagctccccg tggctggaaa gagtggcaat tttaccttc accttgaggc tgtgggtctg    7440
gcacaggctg ggacctacac ctgtagcatc catctgcagg gacagcagct caatgccact    7500
gtcacgttgg cggtcatcac ag                                             7522
```

<210> SEQ ID NO 11
<211> LENGTH: 2292
<212> TYPE: DNA
<213> ORGANISM: Artificial Sequence
<220> FEATURE:
<223> OTHER INFORMATION: a humanized Lag3 allele after recombinase-
      mediated excision of a selection cassette

<400> SEQUENCE: 11

```
ccatcacttt gtataagggc agatcccaaa gctgcctcag cctcccttca acagggaggc      60
atgatgtttc tttcttagga aagccagggc atttctctat tctccaatct cttggctcaa     120
tgcccttggc ctctcttttg ttccactagt gaagcctctc cagccagggg ctgaggtccc     180
ggtggtgtgg gcccaggagg gggctcctgc ccagctcccc tgcagcccca caatcccccct    240 ccaggatctc agccttctgc gaagagcagg ggtcacttgg cagcatcagc cagacaggta     300
tgcaccccaa acttgggcaa caggacctcc gaatccagca ctcaacccca cacccgtgcc     360
ggtcctctgt cccctgccct gaggtgtcac tccctctgaa gccagtgacc cagtctccct     420
gccctcgctt gcaccgttcc tgcccttgct ctgcaatcag cgaccctcac gccagcatcc     480
cttctctcca gaagtggatg cggccagtcc aacagagggg tcgggcgtga ggggacggtt     540
ggtggtcaag agaactcttg gggcgggctt tctcatcctc aacgggtggc tgcctgcatc     600
ctcccgggct tcctacccct ggagcttctc aactccattc tctttcccgc ccagtggccc     660
gcccgctgcc gcccccggcc atccctggc ccccggccct cacccggcgg cgccctcctc      720
ctggggcccc aggccccgcc gctacacggt gctgagcgtg gtcccggag cctgcgcag       780 cgggaggctg cccctgcagc cccgcgtcca gctggatgag cgcggccggc agcgcgggga     840
cttctcgcta tggctgcgcc cagcccggcg cgcggacgcc ggcgagtacc gcgccgcggt     900
gcacctcagg gaccgcgccc tctcctgccg cctccgtctg cgcctgggcc aggcctcgag     960
tatgtggggc gggacgatgg gagaagggct gggaggtggg tccccatccc ctgcctcccg    1020
ggacgcagga agggctgggg cagaggctgc gccctaggcc ctgtcggaga gctcccagaa    1080
gagtagagga aggggtggg cggcctgctg gagtggaagg tgcccccgaa gcacgtgtat     1140 gggggccct gtggagagat tgtgtcaccc ccgagctccc cttctcccac ccacgcggga     1200
gtgcccagag ggaggggag gggggagag catgggcta aagtgattca tttcagatat       1260
ctgtagctca gggggtgggc ttcgcggggt tccaggccag gaaaacggca agggtggctg    1320
atgccaagta aactccaggc cagggacggg gaaagtggtc ctggggagtc ttggggatcc    1380
actttatgca cctccaggtg ctggaagctg agatggggag agggtgatgt gggagaggag    1440
aagacaagtc taaagccagg tgcctgtttc caggagcttc cggcttggca gcctgctgt     1500 gttgggaaat tgtttccagt gggctgatga agtcttcttt atccttgcac agtgactgcc    1560 agcccccag gatctctcag agcctccgac tgggtcattt tgaactgctc cttcagccgc    1620
cctgaccgcc cagcctctgt gcattggttc cggaaccggg gccagggccg agtccctgtc    1680
cgggagtccc cccatcacca cttagcggaa agcttcctct tcctgcccca agtcagcccc    1740
atggactctg ggccctgggg ctgcatcctc acctacagag atggcttcaa cgtctccatc    1800
atgtataacc tcactgttct gggtaactcc cccactctgc ttcacatttg accacaactc    1860
cttcctgccc cccttgtcac ctcccctaac gtcgagataa cttcgtataa tgtatgctat    1920
acgaagttat gctagtaact ataacggtcc taagtagcg agctagcgac ccccaaaact     1980
ttctcagctg cgtgtggtct cactccacat cactttgttt cagtgtccaa accatttttct   2040 ctctgggcat cttttagctg ctgtctctct tactttttatt tatttattgt tgtgtttatt   2100
tatttatttt cattttagcg tgcgttggtg ttttgcctgc atagatgtct gtgtcagggt    2160
attggattcc ctggaacttg acctacagac agtcatgaga taccatatgg gtgctgggaa    2220
ttgaacccag ctcctctgga aggacagcca gtgttctaat ctgccatctc tcactgttta    2280
tcccttggct gt                                                       2292
```

<210> SEQ ID NO 12
<211> LENGTH: 160
<212> TYPE: DNA
<213> ORGANISM: Artificial Sequence
<220> FEATURE:
<223> OTHER INFORMATION: the nucleotide sequence across the upstream
      insertion point between a mouse Lag-3 genomic sequence and a human
      LAG-3 genomic sequence

<400> SEQUENCE: 12
catgatgttt ctttcttagg aaagccaggg catttctcta ttctccaatc tcttggctca      60
atgcccttgg cctctctttt gttccactag tgaagcctct ccagccaggg gctgaggtcc     120
cggtggtgtg ggcccaggag ggggctcctg cccagctccc                           160

<210> SEQ ID NO 13
<211> LENGTH: 190
<212> TYPE: DNA
<213> ORGANISM: Artificial Sequence
<220> FEATURE:
<223> OTHER INFORMATION: the nucleotide sequence comprising a human
      LAG-3 genomic sequence contiguous with the 5' end of a self-
      deleting neomycin cassette

<400> SEQUENCE: 13
ttcacatttg accacaactc cttcctgccc cccttgtcac ctcccctaac gtcgagataa      60
cttcgtataa tgtatgctat acgaagttat atgcatggcc tccgcgccgg gttttggcgc     120
ctcccgcggg cgcccccctc ctcacggcga gcgctgccac gtcagacgaa gggcgcagcg     180
agcgtcctga                                                            190

<210> SEQ ID NO 14
<211> LENGTH: 221
<212> TYPE: DNA
<213> ORGANISM: Artificial Sequence
<220> FEATURE:
<223> OTHER INFORMATION: the nucleotide sequence across the downstream
      insertion point comprising the 3' end of a self-deleting neomycin
      cassette contiguous with a mouse Lag-3 genomic sequence

<400> SEQUENCE: 14
tttcactgca ttctagttgt ggtttgtcca aactcatcaa tgtatcttat catgtctgga      60
ataacttcgt ataatgtatg ctatacgaag ttatgctagt aactataacg gtcctaaggt     120
agcgagctag cgaccccaa aactttctca gctgcgtgtg gtctcactcc acatcacttt     180
gtttcagtgt ccaaaccatt ttctctctgg gcatctttta g                         221

<210> SEQ ID NO 15
<211> LENGTH: 278
<212> TYPE: DNA
<213> ORGANISM: Artificial Sequence
<220> FEATURE:
<223> OTHER INFORMATION: the nucleotide sequence across the upstream
      insertion point after deletion of a neomycin cassette

<400> SEQUENCE: 15
acgtctccat catgtataac ctcactgttc tgggtaactc ccccactctg cttcacattt      60
gaccacaact ccttcctgcc cccttgtca cctcccctaa cgtcgagata acttcgtata     120
atgtatgcta tacgaagtta tgctagtaac tataacggtc ctaaggtagc gagctagcga     180
cccccaaaac tttctcagct gcgtgtggtc tcactccaca tcactttgtt tcagtgtcca     240
aaccattttc tctctgggca tcttttagct gctgtctc                             278

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 16
gaggctgctg acggtcaag                                              19

<210> SEQ ID NO 17
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 17
ttaggcaggt taactttatc ctcaaagca                                   29

<210> SEQ ID NO 18
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 18
gccacgaaga agatgcactc aag                                         23

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
gtcccgggtc tcttggagat                                             20

<210> SEQ ID NO 20
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 20
ccacccataa acatccccag gtttca                                      26

<210> SEQ ID NO 21
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 21
ccgctcattc caagtcagtt c                                           21

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 22
cggttggtgg tcaagagaac                                                    20

<210> SEQ ID NO 23
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 23
cgggctttct catcctcaac ggg                                                23

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 24
ggcgggaaag agaatggagt tg                                                 22

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
agccctgctg tgttgggaaa                                                    20

<210> SEQ ID NO 26
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 26
tgtttccagt gggctgatga agtc                                               24

<210> SEQ ID NO 27
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 27
tggcagtcac tgtgcaag                                                      18
```

NON-HUMAN ANIMALS HAVING A HUMANIZED LYMPHOCYTE-ACTIVATION GENE 3

CROSS-REFERENCE TO RELATED APPLICATIONS

This application claims the benefit of U.S. Provisional Application No. 62/258,181, filed Nov. 20, 2015, and U.S. Provisional Application No. 62/370,430, filed Aug. 3, 2016, the entire contents of which are incorporated herein by reference.

INCORPORATION BY REFERENCE OF SEQUENCE LISTING

The Sequence Listing in the ASCII text file, named as 34031_10212US01_SequenceListing.txt of 49 KB, created on Oct. 18, 2016, and submitted to the United States Patent and Trademark Office via EFS-Web, is incorporated herein by reference.

BACKGROUND

Cancer remains a tremendous challenge in the healthcare industry worldwide, in part, because cancer cells possess the ability to evade the host immune system. Such ability has been understood to be the result of inhibition and/or down-regulation of anti-tumor immunity. Still, development of useful in vivo systems to optimally determine the therapeutic potential of new cancer therapeutics and/or therapeutic regimens that are designed to activate and/or promote anti-tumor immunity and determine the mechanisms of how cancer cells provide inhibitory signals to immune cells, in particular, T cells, is lacking. Such systems provide a source for assays for assessing the therapeutic efficacy of candidate agents that promote an anti-tumor environment in vivo.

SUMMARY

The present invention encompasses the recognition that it is desirable to engineer non-human animals to permit improved systems for identifying and developing new therapeutics and/or therapeutic regimens that can be used for the treatment of cancer. The present invention also encompasses the recognition that it is desirable to engineer non-human animals to permit improved in vivo systems for identifying and developing new therapeutics that can be used to treat autoimmune (or inflammatory, or infectious) diseases, disorders or conditions. The present invention also encompasses the recognition that it is desirable to engineer non-human animals to permit improved in vivo systems for identifying and developing new therapeutics that promote anti-tumor immunity. Further, the present invention also encompasses the recognition that non-human animals having a humanized Lymphocyte-activation gene 3 (Lag-3) and/or otherwise expressing, containing, or producing a human or humanized Lag-3 polypeptide are desirable, for example for use in identifying and developing cancer therapeutics that up-regulate anti-tumor immunity. In some embodiments, non-human animals of the present invention provide improved in vivo systems for the identification and development of combination therapies that include targeting Lag-3 and/or Programmed cell death 1 (PD-1).

In some embodiments, the present invention provides non-human animals having a genome comprising an engineered Lag-3 gene, which engineered Lag-3 gene includes genetic material from two different species (e.g., a human and a non-human). In some embodiments, such an engineered Lag-3 gene includes genetic material that encodes one or more immunoglobulin-like (Ig-like) domains of a human LAG-3 polypeptide. In some embodiments, genetic material encodes the Ig-like domains of a human LAG-3 polypeptide that are responsible for ligand binding (e.g., MHC class II binding). Thus, in some embodiments, an engineered Lag-3 gene of a non-human animal as described herein encodes a Lag-3 polypeptide that contains human and non-human portions, wherein the human and non-human portions are linked together and form a functional Lag-3 polypeptide. In some embodiments, an engineered Lag-3 gene of a non-human animal as described herein encodes a Lag-3 polypeptide that contains the first two Ig-like domains (D1 and D2), in whole or in part, of a human LAG-3 polypeptide. Generally speaking, the first two Ig-like domains (D1 and D2) are contained within the N-terminal 260 amino acids of a human LAG-3 polypeptide; and in some embodiments, within amino acid residues 21-260, 23-260 or 29-260 of a human LAG-3 polypeptide. See, also, FIGS. 1-2, for example.

In some embodiments, a non-human animal is provided, that expresses a Lag-3 polypeptide, which Lag-3 polypeptide comprises a human portion and an endogenous portion.

In some embodiments, a non-human animal is provided, whose genome comprises a humanized Lag-3 gene (or locus) that comprises an endogenous portion and a human portion, wherein the endogenous and human portions are operably linked to a non-human Lag-3 promoter.

In some embodiments, an endogenous portion of a Lag-3 polypeptide comprises an intracellular portion of an endogenous Lag-3 polypeptide. In some embodiments, the endogenous portion of a Lag-3 polypeptide comprises the intracellular domain of an endogenous Lag-3 polypeptide. In some certain embodiments, an endogenous portion of Lag-3 polypeptide further comprises a transmembrane portion of an endogenous Lag-3 polypeptide. In some embodiments, the endogenous portion of a Lag-3 polypeptide comprises the transmembrane domain of an endogenous Lag-3 polypeptide. In some embodiments, the endogenous portion of a Lag-3 polypeptide further comprises an extracellular portion of an endogenous Lag-3 polypeptide, e.g., a C-terminal portion of the extracellular domain of an endogenous Lag-3 polypeptide that does not include the first two Ig-like domains but includes the last two Ig-like domains (D3 and D4). In some embodiments, the endogenous portion of a Lag-3 polypeptide comprises amino acids of the signal peptide of an endogenous Lag-3 polypeptide. For example, the endogenous portion of a Lag-3 polypeptide comprises substantially the signal peptide of an endogenous Lag-3 polypeptide.

In some embodiments, an endogenous portion of Lag-3 polypeptide has an amino acid sequence that is at least 50%, at least 55%, at least 60%, at least 65%, at least 70%, at least 75%, at least 80%, at least 85%, at least 90%, at least 95%, or at least 98% identical to a corresponding amino acid sequence that appears in a rodent Lag-3 polypeptide of SEQ ID NO:2 or SEQ ID NO:4. In some embodiments, an endogenous portion of Lag-3 polypeptide has an amino acid sequence that is substantially identical or identical to a corresponding amino acid sequence that appears in a rodent Lag-3 polypeptide of SEQ ID NO:2 or SEQ ID NO:4.

In some embodiments, an endogenous portion of a humanized Lag-3 gene comprises endogenous non-human Lag-3 exons 1, 5, 6, 7 and 8. In some embodiments, exons 1, 5, 6, 7 and 8 of an endogenous non-human Lag-3 gene are at least 50%, at least 55%, at least 60%, at least 65%, at least 70%, at least 75%, at least 80%, at least 85%, at least 90%, at least 95%, or at least 98% identical to the corresponding exons 1, 5, 6, 7 and 8 that appear in a rodent Lag-3 mRNA sequence of SEQ ID NO:1 or SEQ ID NO:3. In some embodiments, exons 1, 5, 6, 7 and 8 of an endogenous non-human Lag-3 gene are substantially identical or identical to the corresponding exons 1, 5, 6, 7 and 8 that appear in a rodent Lag-3 mRNA sequence of SEQ ID NO:1 or SEQ ID NO:3.

In some embodiments, a human portion (or human sequence) of a humanized Lag-3 polypeptide comprises one or more of the Ig-like domains of a human LAG-3 polypeptide that are responsible for ligand binding (e.g., MHC class II binding). In some embodiments, the human portion of a humanized Lag-3 polypeptide comprises the first two Ig-like domains (D1 and D2), in whole or in part, of a human LAG-3 polypeptide. In some embodiments, within amino acid residues 21-260, 23-260 or 29-260 of a human LAG-3 polypeptide. In some embodiments, the human portion of a humanized Lag-3 polypeptide comprises amino acids 29-260 (or 23-260 or 21-260) of a human LAG-3 polypeptide. In some embodiments, a human portion (or human sequence) of a Lag-3 polypeptide comprises an amino acid sequence that is at least 50%, at least 55%, at least 60%, at least 65%, at least 70%, at least 75%, at least 80%, at least 85%, at least 90%, at least 95%, or at least 98% identical to a corresponding amino acid sequence that appears in a human LAG-3 polypeptide of SEQ ID NO:6. In some embodiments, a human portion (or human sequence) of a Lag-3 polypeptide comprises an amino acid sequence that is substantially identical or identical to a corresponding amino acid sequence that appears in a human LAG-3 polypeptide of SEQ ID NO:6.

In some embodiments, a human portion (or human sequence) of a humanized Lag-3 gene encodes at least amino acids 29-260 (or 23-260 or 21-260) of a human LAG-3 polypeptide. In some embodiments, a human portion (or human sequence) of a humanized Lag-3 gene comprises exons 2-4 (or exons 2, 3 and 4) of a human LAG-3 gene.

In some embodiments, exons 2-4 of a human LAG-3 gene are least 50%, at least 55%, at least 60%, at least 65%, at least 70%, at least 75%, at least 80%, at least 85%, at least 90%, at least 95%, or at least 98% identical to the corresponding exons 2-4 that appear in a human LAG-3 mRNA sequence of SEQ ID NO:5. In some embodiments, exons 2-4 of a human LAG-3 gene are substantially identical or identical to the corresponding exons 2-4 that appear in a human LAG-3 mRNA sequence of SEQ ID NO:5. In some embodiments, a human portion of a humanized Lag-3 gene comprises a sequence that is codon-optimized for expression in a non-human animal as described herein.

In some embodiments, a Lag-3 polypeptide that comprises a human portion and an endogenous portion is encoded by a nucleic acid sequence placed at an endogenous Lag-3 locus (or gene) as described herein.

In some embodiments, an endogenous portion of Lag-3 polypeptide is encoded by endogenous Lag-3 exons 1, 5, 6, 7 and 8.

In some embodiments, a humanized Lag-3 gene includes endogenous non-human Lag-3 exon 1, human LAG-3 exons 2-4, and non-human Lag-3 exons 5-8, wherein the non-human and human exons are operably linked to each other and to an endogenous non-human Lag-3 promoter. In some embodiments, such humanized Lag-3 gene is placed at an endogenous Lag-3 locus.

In some embodiments, a humanized Lag-3 gene encodes a humanized Lag-3 polypeptide that includes a signal peptide that is substantially identical to the signal peptide of an endogenous non-human Lag-3 polypeptide; an extracellular domain that includes a human portion and a non-human portion wherein the human portion comprises the first two Ig-like domains (e.g., a sequence comprising amino acids 26-290) of a human LAG-3 polypeptide and the non-human portion comprises the last two Ig-like domains of an endogenous non-human Lag-3 polypeptide; and the transmembrane and intracellular domains of an endogenous non-human Lag-3 polypeptide.

In some embodiments, a Lag-3 polypeptide produced or expressed by a non-human animal as described herein is provided. In some embodiments, a Lag-3 polypeptide produced or expressed by a non-human animal as described herein is translated in a cell of the non-human animal with a non-human signal peptide, in whole or in part (e.g., a chimeric signal peptide). In some embodiments, a Lag-3 polypeptide produced or expressed by a non-human animal as described herein comprises an amino acid sequence that is at least 50%, at least 55%, at least 60%, at least 65%, at least 70%, at least 75%, at least 80%, at least 85%, at least 90%, at least 95%, or at least 98% identical to an amino acid sequence that appears in a humanized Lag-3 polypeptide of SEQ ID NO:8. In some embodiments, a Lag-3 polypeptide produced or expressed by a non-human animal as described herein comprises an amino acid sequence that is substantially identical or identical to an amino acid sequence that appears in a humanized Lag-3 polypeptide of SEQ ID NO:8.

In some embodiments, an isolated non-human cell or tissue is provided, whose genome comprises a Lag-3 gene (or locus) as described herein. In some embodiments, a cell is a lymphocyte. In some embodiments, a cell is selected from a B cell, dendritic cell, macrophage, monocyte, and a T cell. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, an immortalized cell made, generated or produced from an isolated non-human cell as described herein is provided.

In some embodiments, a non-human embryonic stem (ES) cell is provided, whose genome comprises a Lag-3 gene (or locus) as described herein. In some embodiments, a non-human embryonic stem cell is a rodent embryonic stem cell. In some certain embodiments, a rodent embryonic stem cell is a mouse embryonic stem cell and is from a 129 strain, C57BL strain, or a mixture thereof. In some certain embodiments, a rodent embryonic stem cell is a mouse embryonic stem cell and is a mixture of 129 and C57BL strains. In some embodiments, a non-human ES cell as described herein comprises any one of SEQ ID NO:9, SEQ ID NO:10, SEQ ID NO:11, SEQ ID NO:12, SEQ ID NO:13, SEQ ID NO:14 and SEQ ID NO:15 is provided.

In some embodiments, use of a non-human embryonic stem cell as described herein to make a non-human animal is provided. In some certain embodiments, a non-human embryonic stem cell is a mouse embryonic stem cell and is used to make a mouse comprising a humanized Lag-3 gene (or locus) as described herein. In some certain embodiments, a non-human embryonic stem cell is a rat embryonic stem cell and is used to make a rat comprising a humanized Lag-3 gene (or locus) as described herein.

In some embodiments, a non-human embryo comprising, made from, obtained from, or generated from a non-human embryonic stem cell as described herein is provided. In some certain embodiments, a non-human embryo is a rodent embryo; in some embodiments, a mouse embryo; in some embodiments, a rat embryo.

In some embodiments, use of a non-human embryo described herein to make a non-human animal is provided. In some certain embodiments, a non-human embryo is a mouse embryo and is used to make a mouse comprising a humanized Lag-3 gene (or locus) as described herein. In some certain embodiments, a non-human embryo is a rat embryo and is used to make a rat comprising a humanized Lag-3 gene (or locus) as described herein.

In some embodiments, a kit is provided, comprising an isolated non-human cell or tissue as described herein, an immortalized cell as described herein, non-human embryonic stem cell as described herein, a non-human embryo as described herein, or a non-human animal as described herein.

In some embodiments, a kit as described herein, for use in the manufacture and/or development of a drug (e.g., an antibody or antigen-binding fragment thereof) for therapy or diagnosis is provided.

In some embodiments, a kit as described herein, for use in the manufacture and/or development of a drug (e.g., an antibody or antigen-binding fragment thereof) for the treatment, prevention or amelioration of a disease, disorder or condition is provided.

In some embodiments, a transgene, nucleic acid construct, DNA construct, or targeting vector as described herein is provided. In some certain embodiments, a transgene, nucleic acid construct, DNA construct, or targeting vector comprises a Lag-3 gene (or locus), in whole or in part, as described herein. In some certain embodiments, a transgene, nucleic acid construct, DNA construct, or targeting vector comprises a DNA fragment that includes a Lag-3 gene (or locus), in whole or in part, as described herein. In some certain embodiments, a transgene, nucleic acid construct, DNA construct, or targeting vector comprises a Lag-3 gene (or locus) that comprises any one of SEQ ID NO:9, SEQ ID NO:10, SEQ ID NO:11, SEQ ID NO:12, SEQ ID NO:13, SEQ ID NO:14 and SEQ ID NO:15. In some certain embodiments, a transgene, nucleic acid construct, DNA construct, or targeting vector further comprises one or more selection markers. In some certain embodiments, a transgene, nucleic acid construct, DNA construct, or targeting vector further comprises one or more site-specific recombination sites (e.g., loxP, Frt, or combinations thereof). In some certain embodiments, a transgene, nucleic acid construct, DNA construct, or targeting vector is depicted in FIG. 3.

In some embodiments, use of a transgene, nucleic acid construct, DNA construct, or targeting vector as described herein to make a non-human embryonic stem cell, non-human cell, non-human embryo and/or non-human animal is provided.

In some embodiments, a method of making a non-human animal that expresses a Lag-3 polypeptide from an endogenous Lag-3 gene is provided, wherein the Lag-3 polypeptide comprises a human sequence, the method comprising (a) placing a genomic fragment into an endogenous Lag-3 gene in a non-human embryonic stem cell, said genomic fragment comprising a nucleotide sequence that encodes a human Lag-3 polypeptide in whole or in part; (b) obtaining the non-human embryonic stem cell generated in (a); and, (c) creating a non-human animal using the non-human embryonic stem cell of (b).

In some embodiments of a method of making a non-human animal that expresses a Lag-3 polypeptide from an endogenous Lag-3 gene, the method further comprises a step of placing a genomic fragment into an endogenous Pdcd1 gene of the non-human embryonic stem cell of (a), said genomic fragment comprising a nucleotide sequence that encodes a human PD-1 polypeptide in whole or in part. In some embodiments of a method of making a non-human animal that expresses a Lag-3 polypeptide from an endogenous Lag-3 gene, a genomic fragment comprising a nucleotide sequence that encodes a human PD-1 polypeptide in whole or in part is placed into an endogenous Pdcd1 gene of the non-human embryonic stem cell of (a) prior to, simultaneously with, or after the placement of genomic fragment that comprises the nucleotide sequence that encodes the human Lag-3 polypeptide in whole or in part into the endogenous Lag-3 gene. In some embodiments of a method of making a non-human animal that expresses a Lag-3 polypeptide from an endogenous Lag-3 gene, the method further comprises breeding the non-human animal of (c) with a second non-human animal, said second non-human animal having a genome comprising a Pdcd1 gene that encodes a PD-1 polypeptide comprising a human portion and an endogenous portion.

In some embodiments, a nucleotide sequence comprises human Lag-3 exons 2-4. In some embodiments, a nucleotide sequence encodes at least amino acids 29-260 (or 23-260 or 21-260) of a human LAG-3 polypeptide. In some embodiments, a nucleotide sequence comprises one or more selection markers. In some embodiments, a nucleotide sequence comprises one or more site-specific recombination sites.

In some embodiments, a method of making a non-human animal whose genome comprises a Lag-3 gene that encodes a Lag-3 polypeptide having a human portion and an endogenous portion is provided, the method comprising modifying the genome of a non-human animal so that it comprises a Lag-3 gene that encodes a Lag-3 polypeptide having a human portion and an endogenous portion, which portions are operably linked to a non-human Lag-3 promoter, thereby making said non-human animal.

In some embodiments of a method of making a non-human animal whose genome comprises a Lag-3 gene that encodes a Lag-3 polypeptide having a human portion and an endogenous portion, a Lag-3 gene is modified to include exons 2-4 (or exons 2, 3 and 4) of a human LAG-3 gene. In some embodiments of a method of making a non-human animal whose genome comprises a Lag-3 gene that encodes a Lag-3 polypeptide having a human portion and an endogenous portion, a Lag-3 gene is modified to encode at least amino acids 29-260 (or 23-260 or 21-260) of a human LAG-3 polypeptide.

In some embodiments of a method of making a non-human animal whose genome comprises a Lag-3 gene that encodes a Lag-3 polypeptide having a human portion and an endogenous portion, the method further comprises modifying the genome of the non-human animal so that it comprises a Pdcd1 gene that encodes a PD-1 polypeptide comprising a human portion and an endogenous portion. In some embodiments of a method of making a non-human animal whose genome comprises a Lag-3 gene that encodes a Lag-3 polypeptide having a human portion and an endogenous portion, modifying the genome of the non-human animal so that it comprises a Pdcd1 gene that encodes a PD-1 polypeptide comprising a human portion and an endogenous portion is performed prior to, simultaneously with, or after modifying the genome of the non-human animal so that it comprises a Lag-3 gene that encodes a Lag-3 polypeptide having a human portion and an endogenous portion. In some embodiments of a method of making a non-human animal whose genome comprises a Lag-3 gene that encodes a Lag-3 polypeptide having a human portion and an endogenous portion, the method further comprises breeding the non-human animal whose genome comprises a Lag-3 gene that encodes a Lag-3 polypeptide having a human portion and an endogenous portion with a second non-human animal, said second non-human animal having a genome comprising a Pdcd1 gene that encodes a PD-1 polypeptide comprising a human portion and an endogenous portion.

In some embodiments, a non-human animal obtainable by (made from, obtained from, or generated from) any one of the methods as described herein is provided.

In some embodiments, a method of assessing anti-tumor efficacy of a drug targeting human LAG-3 is provided, the method comprising the steps of administering the drug to a non-human animal as described herein, and performing an assay to determine one or more anti-tumor properties of the drug targeting human LAG-3.

In some embodiments, a method of assessing the pharmacokinetic properties of a drug targeting human LAG-3 is provided, the method comprising the steps of administering the drug to a non-human animal as described herein, and performing an assay to determine one or more pharmacokinetic properties of the drug targeting human LAG-3.

In some embodiments, a drug targeting human LAG-3 is a Lag-3 antagonist. In some embodiments, a drug targeting human LAG-3 is a Lag-3 agonist. In some embodiments, a drug targeting human LAG-3 is an anti-Lag-3 antibody.

In some embodiments, a drug targeting human LAG-3 is administered to a non-human animal as described herein intravenously, intraperitoneally or subcutaneously.

In some embodiments, a non-human animal is provided, whose genome comprises a Lag-3 gene that includes an endogenous portion that comprises endogenous Lag-3 exons 1, 5, 6, 7 and 8; and a human portion that comprises exons 2-4 (or exons 2, 3 and 4) of a human LAG-3 gene; wherein the endogenous and human portions are operably linked to an endogenous non-human Lag-3 promoter, and wherein the non-human animal expresses a Lag-3 polypeptide that comprises amino acids 29-260 (or 23-260 or 21-260) of a human LAG-3 polypeptide.

In some embodiments, a non-human animal tumor model is provided, which non-human animal expresses a Lag-3 and/or PD-1 polypeptide as described herein.

In some embodiments, a non-human animal tumor model is provided, which non-human animal has a genome comprising a Lag-3 and/or Pdcd1 gene as described herein.

In some embodiments, a non-human animal tumor model is provided, obtained by (a) providing a non-human animal whose genome comprises a Lag-3 and/or Pdcd1 gene as described herein; and (b) implanting one or more tumor cells in the non-human animal of (a); thereby providing said non-human animal tumor model.

In some embodiments, a non-human animal or cell as described herein is provided, for use in the manufacture and/or development of a drug for therapy or diagnosis.

In some embodiments, a non-human animal or cell as described herein is provided, for use in the manufacture of a medicament for the treatment, prevention or amelioration of a disease, disorder or condition.

In some embodiments, use of a non-human animal or cell as described herein in the manufacture and/or development of a drug or vaccine for use in medicine, such as use as a medicament is provided.

In some embodiments, use of a non-human animal or cell as described herein in the manufacture of a medicament for the treatment of a disease, disorder or condition is provided.

In some embodiments, use of a non-human animal or cell as described herein in the manufacture and/or development of an antibody that binds an immune checkpoint molecule is provided.

In some embodiments, a disease, disorder or condition as described herein is cancer or a neoplasm. In some embodiments, a disease, disorder or condition as described herein is an autoimmune (or inflammatory) disease, disorder or condition. In some embodiments, a disease, disorder or condition as described herein is an infectious disease, disorder or condition.

In various embodiments, a non-human Lag-3 promoter is or comprises an endogenous non-human Lag-3 promoter.

In various embodiments, a human portion (or human sequence, or nucleotide sequence) of Lag-3 or Pdcd1 gene as described herein is or comprises a sequence that is codon-optimized for expression in a non-human animal (or non-human cell or tissue) as described herein.

In various embodiments, a non-human animal (or non-human cell or tissue, or non-human embryonic stem cell, or non-human embryo) as described herein further expresses a humanized PD-1 polypeptide, which humanized PD-1 polypeptide comprises a human portion and an endogenous portion. In some embodiments, a human portion of a PD-1 polypeptide comprises substantially the extracellular domain of a human PD-1 polypeptide; and in specific embodiments, a human portion comprises amino acids 21-170, 26-169, 27-169, 27-145 or 35-145 of a human PD-1 polypeptide. In some embodiments, an endogenous portion of a PD-1 polypeptide comprises an intracellular portion and/or a transmembrane portion of an endogenous PD-1 polypeptide; in some embodiments, an endogenous portion of a PD-1 polypeptide comprises the intracellular domain of an endogenous PD-1 polypeptide, and in certain embodiments, an endogenous portion of a PD-1 polypeptide further comprises substantially the transmembrane domain of an endogenous PD-1 polypeptide.

In various embodiments, the genome of a non-human animal (or non-human cell or tissue, or non-human embryonic stem cell, or non-human embryo) as described herein further comprises a Pdcd1 gene that comprises an endogenous portion and a human portion, wherein the endogenous and human portions are operably linked to a non-human Pdcd1 promoter. In some embodiments, an endogenous portion of a Pdcd1 gene comprises endogenous Pdcd1 exons 1, 4 and 5. In some embodiments, an endogenous portion of a Pdcd1 gene further comprises endogenous Pdcd1 exon 3 in whole or in part, for example, a 3' portion of endogenous exon 3 that encodes amino acids that are part of the transmembrane domain of an endogenous PD-1 polypeptide. In some embodiments, a human portion of a Pdcd1 gene encodes amino acids 35-145, 27-145, 27-169, 26-169 or 21-170 of a human PD-1 polypeptide. In some embodiments, a human portion of a Pdcd1 gene comprises exon 2 of a human PDCD1 gene; in some certain embodiments, further comprises a human PDCD1 exon 3 in whole or in part, for example, a 5' portion of human exon 3 that encodes amino acids that are part of the extracellular domain of a human PD-1 polypeptide. In specific embodiments, a humanized Pdcd1 gene in a non-human animal comprises exon 1 of an endogenous Pdcd1 gene of the non-human animal, exon 2 and a part of exon 3 (e.g., a 5' portion of exon 3 that encodes amino acids that are part of the extracellular domain) of a human PDCD1 gene, followed by a part of exon 3 (e.g., a 3' portion of exon 3 that encodes amino acids that are part of the transmembrane domain) and exons 4-5 of an endogenous non-human Pdcd1 gene.

In various embodiments, a non-human Pdcd1 promoter is or comprises an endogenous non-human Pdcd1 promoter.

In various embodiments, a human portion of a Lag-3 gene encodes an amino acid sequence of immunoglobulin-like (Ig-like) domains 1 (D1) and 2 (D2) of a human LAG-3 polypeptide, or encodes an amino acid sequence of a human LAG-3 polypeptide that is responsible for binding MHC II.

In various embodiments, a human portion of a Lag-3 polypeptide comprises an amino acid sequence of immunoglobulin-like (Ig-like) domains 1 (D1) and 2 (D2) of a human LAG-3 polypeptide, or comprises an amino acid sequence of a human LAG-3 polypeptide that is responsible for binding MHC II.

In various embodiments, a non-human animal as described herein is a rodent; in some embodiments, a mouse; in some embodiments, a rat. In some embodiments, a mouse as described herein is selected from the group consisting of a 129 strain, a BALB/C strain, a C57BL/6 strain, and a mixed 129xC57BL/6 strain; in some certain embodiments, a C57BL/6 strain.

As used in this application, the terms "about" and "approximately" are used as equivalents. Any numerals used in this application with or without about/approximately are meant to cover any normal fluctuations appreciated by one of ordinary skill in the relevant art.

BRIEF DESCRIPTION OF THE DRAWING

The Drawing included herein, which is composed of the following Figures, is for illustration purposes only and not for limitation.

FIG. 2 shows an alignment of representative amino acid sequences of human LAG-3 (hLAG3) (SEQ ID NO: 6), mouse Lag-3 (mLag3) (SEQ ID NO: 4) and humanized Lag-3 (HumLAG3) (SEQ ID NO: 8). Asterisks indicate immunoglobulin-like (Ig-like) domains and underlined text indicates amino acids encoded by inserted human LAG-3 exons (i.e., exons 2, 3 and 4). Ig-like domains 1 (D1) and 2 (D2) are separated by a single amino indicated by forward slash below the sequence.

FIG. 8 shows exemplary rodent (e.g., rat and mouse), human, and humanized lymphocyte-activation gene 3 (Lag-3) sequences, as well as an exemplary synthetic DNA fragment for humanization of a non-human Lag-3 gene. For mRNA sequences, bold font indicates coding sequence, and consecutive exons, where indicated, are separated by alternating underlined text; for humanized mRNA sequences, human sequences are contained within parentheses. For amino acid sequences, transmembrane sequences are indicated by underlined font; for humanized amino acid sequences, human sequences are indicated in bold font and contained within parentheses.

FIGS. 9A-9D show junction sequences in certain exemplified humanized Lag-3 locus. FIG. 9A shows the nucleotide sequence (SEQ ID NO: 12) across the upstream insertion point, which indicates endogenous mouse sequence (contained within the parentheses below) contiguous with human LAG-3 genomic sequence at the insertion point. FIG. 9B shows the nucleotide sequence (SEQ ID NO: 13) across the 5' end of the self-deleting neomycin cassette, which indicates human LAG-3 genomic sequence contiguous with cassette sequence (contained within the parentheses below with a SalI-XhoI compatible end italicized and a loxP sequence in bold font) downstream of the insertion point. FIG. 9C shows the nucleotide sequence (SEQ ID NO: 14) across the downstream insertion point at the 3' end of the self-deleting neomycin cassette, which indicates cassette sequence (contained within the parentheses below with a loxP site in bold, an I-CeuI recognition site underlined and an NheI recognition site italicized) contiguous with mouse Lag-3 genomic sequence.

FIG. 9D shows the nucleotide sequence (SEQ ID NO: 15) across the upstream insertion point after deletion of the neomycin cassette (77 bp remaining in intron 4), which indicates mouse and human genomic sequence juxtaposed with remaining cassette sequence loxP sequence (contained within the parentheses below with a SalI-XhoI compatible end italicized, a loxP site in bold, an I-CeuI restriction site underlined and an NheI restriction site italicized).

DEFINITIONS

Figure 1:
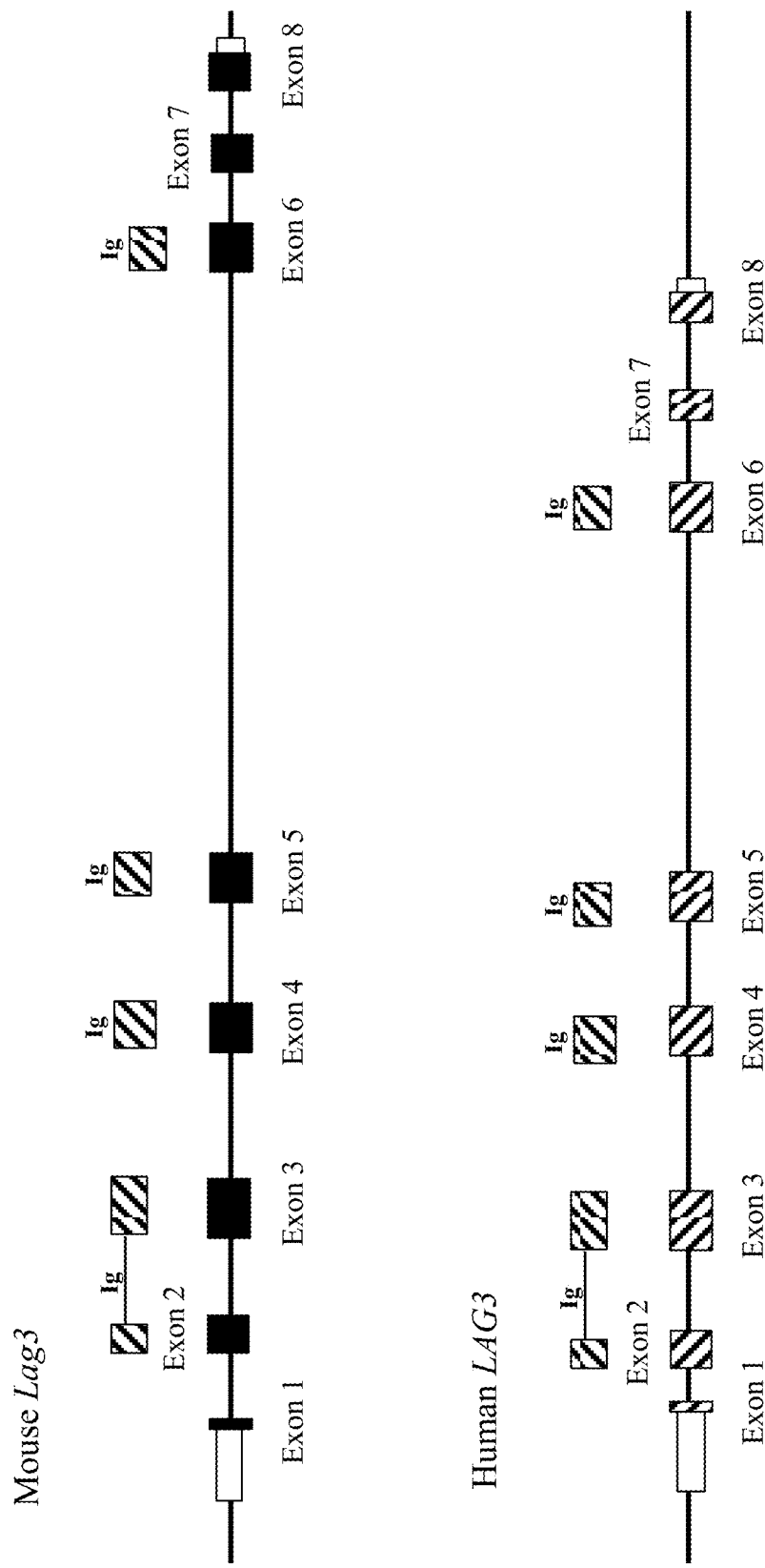
FIG. 1 shows a diagram, not to scale, of the genomic organization of a non-human (e.g., mouse) and human Lymphocyte-activation gene 3 (Lag-3). Exons are numbered above or below each exon. Untranslated regions (open boxes) are also indicated for each gene Immunoglobulin-like domains are indicated, not to scale, by stripped boxes and the symbolic abbreviation "Ig" above the encoding exons.

This invention is not limited to particular methods and experimental conditions described herein, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All patent and non-patent publications mentioned herein are hereby incorporated by reference.

Approximately: as applied herein to one or more values of interest, includes a value that is similar to a stated reference value. In certain embodiments, the term "approximately" or "about" includes a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: as used herein, includes a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Comparable: as used herein, includes two or more agents, entities, situations, sets of conditions, etc. that may not be identical to one another but that are sufficiently similar to permit comparison between them so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Conservative: as used herein to describe a conservative amino acid substitution, includes substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

Control: as used herein, includes the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. As used herein, a "control" may include a "control animal". A "control animal" may have a modification as described herein, a modification that is different as described herein, or no modification (i.e., a wild-type animal). In one experiment, the "test" (i.e., the variable being tested) is applied. In the second experiment, the "control" (i.e., the variable being tested) is not applied. In some embodiments, a control is a historical control (i.e., of a test or assay performed previously, or an amount or result that is previously known). In some embodiments, a control is or comprises a printed or otherwise saved record. A control may be a positive control or a negative control.

Disruption: as used herein, includes the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g., exons, which may be of an origin other than the endogenous sequence (e.g., a heterologous sequence). In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

Determining, measuring, evaluating, assessing, assaying and analyzing: are used interchangeably herein to include any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

Endogenous locus or endogenous gene: as used herein, includes a genetic locus found in a parent or reference organism prior to introduction of an alteration, disruption, deletion, insertion, modification, replacement, or substitution as described herein. In some embodiments, the endogenous locus has a sequence found in nature. In some embodiments, the endogenous locus is a wild type locus. In some embodiments, the reference organism is a wild type organism. In some embodiments, the reference organism is an engineered organism. In some embodiments, the reference organism is a laboratory-bred organism (whether wild type or engineered).

Endogenous promoter: as used herein, includes a promoter that is naturally associated, e.g., in a wild-type organism, with an endogenous gene.

Engineered: as used herein, in general, includes the aspect of having been manipulated by the hand of man. For example, in some embodiments, a polynucleotide may be considered to be "engineered" when two or more sequences that are not linked together in that order in nature are manipulated by the hand of man to be directly linked to one another in the engineered polynucleotide. In some particular such embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by those in the art, progeny of an engineered polynucleotide or cell are typically still referred to as "engineered" even though the actual manipulation was performed on a prior entity. Furthermore, as will be appreciated by those skilled in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc.). Alternatively or additionally, in some embodiments, "engineering" may involve use of in vitro chemical synthesis methodologies and/or recombinant nucleic acid technologies such as, for example, nucleic acid amplification (e.g., via the polymerase chain reaction) hybridization, mutation, transformation, transfection, etc., and/or any of a variety of controlled mating methodologies. As will be appreciated by those skilled in the art, a variety of established such techniques (e.g., for recombinant DNA, oligonucleotide synthesis, and tissue culture and transformation (e.g., electroporation, lipofection, etc.)) are well known in the art and described in various general and more specific references that are cited and/or discussed throughout the present specification. See e.g., Sambrook et al., Molecular Cloning: A Laboratory Manual (2d ed., Cold Spring Harbor Laboratory Press, Cold Spring Harbor, N.Y., 1989).

Gene: as used herein, includes a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity we note that, as used in the present application, the term "gene" generally includes a portion of a nucleic acid that encodes a polypeptide; the term may optionally encompass regulatory sequences, as will be clear from context to those of ordinary skill in the art. This definition is not intended to exclude application of the term "gene" to non-protein-coding expression units but rather to clarify that, in most cases, the term as used in this document includes a polypeptide-coding nucleic acid.

Heterologous: as used herein, includes an agent or entity from a different source. For example, when used in reference to a polypeptide, gene, or gene product present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

Host cell: as used herein, includes a cell into which a heterologous (e.g., exogenous) nucleic acid or protein has been introduced. Persons of skill upon reading this disclosure will understand that such terms include not only the particular subject cell, but also is used to include the progeny of such a cell. Because certain modifications may occur in succeeding generations due to either mutation or environmental influences, such progeny may not, in fact, be identical to the parent cell, but are still included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

Humanized: is used herein in accordance with its art-understood meaning to include nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide having an extracellular portion, in whole or in part, having an amino acid sequence as that of a human extracellular portion and the remaining sequence as that of a non-human (e.g., mouse) polypeptide. In some embodiments, a humanized gene comprises at least a portion of a DNA sequence of a human gene. In some embodiments, a humanized gene comprises an entire DNA sequence of a human gene. In some embodiments, a humanized protein comprises a sequence having a portion that appears in a human protein. In some embodiments, a humanized protein comprises an entire sequence of a human protein and is expressed from an endogenous locus of a non-human animal that corresponds to the homolog or ortholog of the human gene.

Identity: as used herein in connection with a comparison of sequences, includes identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

In vitro: as used herein includes events that occur in an artificial environment, e.g., in a test tube or reaction vessel, in cell culture, etc., rather than within a multi-cellular organism.

In vivo: as used herein includes events that occur within a multi-cellular organism, such as a human and a non-human animal. In the context of cell-based systems, the term may be used to include events that occur within a living cell (as opposed to, for example, in vitro systems).

Isolated: as used herein, includes a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized or is synthesized in a different cellular system from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

"Locus" or "Loci": as used herein, includes a specific location(s) of a gene (or significant sequence), DNA sequence, polypeptide-encoding sequence, or position on a chromosome of the genome of an organism. For example, a "Lag-3 locus" may include the specific location of a Lag-3 gene, Lag-3 DNA sequence, Lag-3-encoding sequence, or Lag-3 position on a chromosome of the genome of an organism that has been identified as to where such a sequence resides. A "Lag-3 locus" may comprise a regulatory element of a Lag-3 gene, including, but not limited to, an enhancer, a promoter, 5' and/or 3' UTR, or a combination thereof. Those of ordinary skill in the art will appreciate that chromosomes may, in some embodiments, contain hundreds or even thousands of genes and demonstrate physical co-localization of similar genetic loci when comparing between different species. Such genetic loci may be described as having shared synteny.

Non-human animal: as used herein, includes any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human animal as described herein is a mammal. In some embodiments, a non-human mammal is a primate, a goat, a sheep, a pig, a dog, a cow, or a rodent. In some embodiments, a non-human animal as described herein is a small mammal, e.g., of the superfamily Dipodoidea or Muroidea. In some embodiments, a genetically modified animal as described herein is a rodent. In some embodiments, a rodent as described herein is selected from a mouse, a rat, and a hamster. In some embodiments, a rodent as described herein is selected from the superfamily Muroidea. In some embodiments, a genetically modified animal as described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, white-tailed rats, Malagasy rats and mice), Platacanthomyidae (e.g., spiny dormice), and Spalacidae (e.g., mole rates, bamboo rats, and zokors). In some certain embodiments, a genetically modified rodent as described herein is selected from a true mouse or rat (family Muridae), a gerbil, a spiny mouse, and a crested rat. In some certain embodiments, a genetically modified mouse as described herein is from a member of the family Muridae. In some embodiment, a non-human animal as described herein is a rodent. In some certain embodiments, a rodent as described herein is selected from a mouse and a rat. In some embodiments, a non-human animal as described herein is a mouse.

In some embodiments, a non-human animal as described herein is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse as described herein is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5):1024-1028, 1030, 1032). In some certain embodiments, a genetically modified mouse as described herein is a mix of an aforementioned 129 strain and an aforementioned C57BL/6 strain. In some certain embodiments, a mouse as described herein is a mix of aforementioned 129 strains, or a mix of aforementioned BL/6 strains. In some certain embodiments, a 129 strain of the mix as described herein is a 129S6 (129/SvEvTac) strain. In some embodiments, a mouse as described herein is a BALB strain, e.g., BALB/c strain. In some embodiments, a mouse as described herein is a mix of a BALB strain and another aforementioned strain.

In some embodiments, a non-human animal as described herein is a rat. In some certain embodiments, a rat as described herein is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Nucleic acid: as used herein, in its broadest sense, includes any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" includes individual nucleic acid residues (e.g., nucleotides and/or nucleosides); in some embodiments, "nucleic acid" includes an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone, are considered within the scope of the present invention. Alternatively or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or protein. In some embodiments, a "nucleic acid" includes one or more introns. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

Operably linked: as used herein, includes a juxtaposition wherein the components described are in a relationship permitting them to function in their intended manner A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence", as used herein, includes polynucleotide sequences, which are necessary to effect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence);

sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Patient or subject: as used herein, includes any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a non-human animal. In some embodiments, a patient (e.g., a non-human animal patient) may have a modification as described herein, a modification that is different as described herein or no modification (i.e., a wild-type non-human animal patient). In some embodiments, a non-human animal is suffering from or susceptible to one or more disorders or conditions. In some embodiments, a non-human animal displays one or more symptoms of a disorder or condition. In some embodiments, a non-human animal has been diagnosed with one or more disorders or conditions.

Polypeptide: as used herein, includes any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man.

Recombinant: as used herein, is intended to include polypeptides (e.g., Lag-3 polypeptides as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., 1997, TIB Tech. 15:62-70; Azzazy H., and Highsmith W. E., 2002, Clin. Biochem. 35:425-445; Gavilondo J. V., and Larrick J. W., 2002, BioTechniques 29:128-145; Hoogenboom H., and Chames P., 2000, Immunology Today 21:371-378), antibodies isolated from an animal (e.g., a mouse) that is transgenic for human immunoglobulin genes (see e.g., Taylor, L. D. et al., 1992, Nucl. Acids Res. 20:6287-6295; Kellermann S-A., and Green L. L., 2002, Current Opinion in Biotechnology 13:593-597; Little M. et al., 2000, Immunology Today 21:364-370; Murphy, A. J. et al., 2014, Proc. Natl. Acad. Sci. U.S.A. 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

Replacement: as used herein, includes a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice acceptor site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a polypeptide that has a similar function as a polypeptide encoded by the endogenous sequence (e.g., the endogenous genomic sequence encodes a Lag-3 polypeptide, and the DNA fragment encodes one or more human Lag-3 polypeptides, in whole or in part). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

Reference: as used herein, describes a standard or control agent, cohort, individual, population, sample, sequence or value against which an agent, animal, cohort, individual, population, sample, sequence or value of interest is compared. In some embodiments, a reference agent, cohort, individual, population, sample, sequence or value is tested and/or determined substantially simultaneously with the testing or determination of the agent, cohort, individual, population, sample, sequence or value of interest. In some embodiments, a reference agent, cohort, individual, population, sample, sequence or value is a historical reference, optionally embodied in a tangible medium. In some embodiments, a reference may refer to a control. As used herein, a "reference" may refer to a "reference animal". A "reference animal" may have a modification as described herein, a modification that is different as described herein or no modification (i.e., a wild-type animal) Typically, as would be understood by those skilled in the art, a reference agent, animal, cohort, individual, population, sample, sequence or value is determined or characterized under conditions comparable to those utilized to determine or characterize the agent, animal (e.g., a mammal), cohort, individual, population, sample, sequence or value of interest.

Substantially: as used herein, includes the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. The term is also used herein when referring to a sequence, a nucleic acid or protein molecule, or a protein domain, in comparison to a reference sequence, molecule or domain. For example, in referring to a humanized Lag-3 polypeptide comprising substantially the signal peptide of a non-human Lag-3 polypeptide, the phrase "substantially the signal peptide of a non-human Lag-3 polypeptide" includes a peptide that is substantially identical the signal peptide of a non-human Lag-3 polypeptide, which peptide, in some embodiments, is at least 85%, 90%, 95%, 95%, 99% or 100% identical in sequence with the signal peptide of a non-human Lag-3 polypeptide; and in some embodiments, differs from the signal peptide of a non-human Lag-3 polypeptide by not more than 5, 4, 3, 2 or 1 amino acid(s), preferably only at the N— or C— terminus of the signal peptide, e.g., by lacking amino acid(s) or having additional amino acid(s) at the at the N— or C— terminus of the signal peptide. As another example, in referring to a humanized PD-1 polypeptide comprising substantially the extracellular domain of a human PD-1 protein, the phrase "substantially the extracellular domain of a human PD-1 protein" includes a polypeptide that is substantially identical with the extracellular domain of a human PD-1 protein, which polypeptide, in some embodiments, is at least 85%, 90%, 95%, 95%, 99% or 100% identical in sequence with the extracellular domain of a human PD-1 protein; and in some embodiments, differs from the extracellular domain of a human PD-1 protein by not more than 5, 4, 3, 2 or 1 amino acid(s), preferably only at the N— or C— terminus, e.g., by lacking amino acids or having additional amino acids at the at the N— or C— terminus.

Substantial homology: as used herein, includes a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, Basic local alignment search tool, J. Mol. Biol., 215(3): 403-410; Altschul et al., 1996, Methods Enzymol. 266:160-80; Altschul et al., 1997, Nucleic Acids Res. 25:3389-3402; Baxevanis et al., 1998 Bioinformatics: A Practical Guide to the Analysis of Genes and Proteins, Wiley; and Misener et al. (eds.) (1999) Bioinformatics Methods and Protocols (Methods in Molecular Biology, Vol. 132), Humana Press. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

Substantial identity: as used herein, includes a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., 1990, Basic local alignment search tool, J.

Mol. Biol., 215(3): 403-410; Altschul et al., 1996, Methods Enzymol. 266:160-80; Altschul et al., 1997, Nucleic Acids Res. 25:3389-3402; Baxevanis et al., 1998, Bioinformatics: A Practical Guide to the Analysis of Genes and Proteins, Wiley; Misener et al., (eds.) (1999) Bioinformatics Methods and Protocols (Methods in Molecular Biology, Vol. 132), Humana Press. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

Targeting vector or targeting construct: as used herein, includes a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP and/or Frt sites) are also included. In some embodiments, a targeting construct further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct further comprises a gene of interest in whole or in part, wherein the gene of interest is a heterologous gene that encodes a protein, in whole or in part, that has a similar function as a protein encoded by an endogenous sequence. In some embodiments, a targeting construct further comprises a humanized gene of interest, in whole or in part, wherein the humanized gene of interest encodes a protein, in whole or in part, that has a similar function as a protein encoded by the endogenous sequence. In some embodiments, a targeting construct further comprises an engineered gene of interest, in whole or in part, wherein the engineered gene of interest encodes a protein, in whole or in part, that has a similar function as a protein encoded by an endogenous sequence.

Variant: as used herein, includes an entity that shows significant structural identity with a reference entity, but differs structurally from the reference entity in the presence or level of one or more chemical moieties as compared with the reference entity. In many embodiments, a "variant" also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A "variant", by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc.) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a "variant polypeptide" may differ from a reference polypeptide as a result of one or more differences in amino acid sequence and/or one or more differences in chemical moieties (e.g., carbohydrates, lipids, etc.) covalently attached to the polypeptide backbone. In some embodiments, a "variant polypeptide" shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a "variant polypeptide" does not share at least one characteristic sequence element with a reference polypeptide. In some embodiments, the reference polypeptide has one or more biological activities. In some embodiments, a "variant polypeptide" shares one or more of the biological activities of the reference polypeptide. In some embodiments, a "variant polypeptide" lacks one or more of the biological activities of the reference polypeptide. In some embodiments, a "variant polypeptide" shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a "variant" has 10, 9, 8, 7, 6, 5, 4, 3, 2, or 1 substituted residue as compared with a parent. Often, a "variant" has a very small number (e.g., fewer than 5, 4, 3, 2, or 1) of substituted functional residues (i.e., residues that participate in a particular biological activity). Furthermore, a "variant" typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

Vector: as used herein, includes a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors".

Wild type: as used herein, has its art-understood meaning that includes an entity having a structure and/or activity as found in nature in a "normal" (as contrasted with mutant, diseased, altered, etc.) state or context. Those of ordinary skill in the art will appreciate that wild type genes and polypeptides often exist in multiple different forms (e.g., alleles).

DETAILED DESCRIPTION OF CERTAIN EMBODIMENTS

The present invention provides, among other things, improved and/or engineered non-human animals having humanized genetic material encoding a Lymphocyte-activation gene 3 (Lag-3) polypeptide for determining the therapeutic efficacy of Lag-3 modulators (e.g., an anti-Lag-3 antibodies) for the treatment of cancer, and assays in T cell responses and signal transduction. It is contemplated that such non-human animals provide an improvement in determining the therapeutic efficacy of Lag-3 modulators and their potential for Lag-3 blockade. Therefore, the present invention is particularly useful for the development of anti-Lag-3 therapies for the treatment of various cancers and autoimmune diseases, disorders or conditions. In particular, the present invention encompasses the humanization of a non-human (such as murine) Lag-3 gene resulting in expression of a humanized Lag-3 polypeptide on the surface of cells of the non-human animal. Such humanized Lag-3 polypeptides have the capacity to provide a source of human Lag-3$^+$ cells for determining the efficacy of anti-Lag-3 therapeutics to promote anti-tumor immune responses. In some embodiments, non-human animals as described herein demonstrate augmented immune responses via blockade of Lag-3 signaling through the humanized Lag-3 polypeptide expressed on the surface of cells of the non-human animal. In some embodiments, humanized Lag-3 polypeptides comprise a sequence corresponding to an extracellular portion of a human LAG-3 polypeptide, for example, an extracellular portion that contains the first two Ig-like domains of a human LAG-3 polypeptide. In some embodiments, humanized Lag-3 polypeptides comprise a sequence corresponding to amino acids 29-260 (or 23-260 or 21-260) of a human LAG-3 polypeptide. In some embodiments, humanized Lag-3 polypeptides comprise a sequence corresponding to the transmembrane domain and/or intracellular tail of a non-human (e.g., rodent such as murine) Lag-3 polypeptide. In some embodiments, a humanized Lag-3 polypeptide comprises an extracellular portion that contains the first two Ig-like domains of a human LAG-3 polypeptide, wherein the remaining portions of the humanized Lag-3 polypeptide are comprised of amino acids of a non-human (e.g., rodent such as murine) Lag-3 polypeptide. In some embodiments, a humanized Lag-3 polypeptide includes a signal peptide substantially identical to the signal peptide of an endogenous non-human Lag-3 polypeptide, an extracellular domain that includes a human portion and a non-human portion wherein the human portion comprises the first two Ig-like domains of a human LAG-3 polypeptide and the non-human portion comprises the last two Ig-like domains of an endogenous non-human Lag-3 polypeptide; and the transmembrane and intracellular domains of an endogenous non-human Lag-3 polypeptide. In some embodiments, non-human animals as described herein comprise a humanized Lag-3 gene that contains genetic material from the non-human animal and a heterologous species (e.g., a human). In some embodiments, non-human animals as described herein comprise a humanized Lag-3 gene, wherein the humanized Lag-3 gene comprises exons 2 to 4 of a human LAG-3 gene. In some certain embodiments, non-human animals as described herein comprise a humanized Lag-3 gene, wherein the humanized Lag-3 gene comprises ~1,741 bp of a human LAG-3 gene corresponding to exons 2 through 4 and a portion of intron 4 (e.g., ~68 bp) of a human LAG-3 gene. In some embodiments, a non-human animal as described herein comprises a humanized Lag-3 gene, wherein the humanized Lag-3 gene comprises exon 1 of an endogenous Lag-3 gene of the non-human animal, exons 2 to 4 of a human LAG-3 gene, and exons 5-8 of an endogenous Lag-3 gene of the non-human animal, wherein the humanized Lag-3 gene is placed at an endogenous Lag-3 locus and operably linked to the endogenous Lag-3 promoter at the locus.

Various aspects of the invention are described in detail in the following sections. The use of sections is not meant to limit the invention. Each section can apply to any aspect of the invention. In this application, the use of "or" means "and/or" unless stated otherwise.

Lymphocyte-Activation Gene 3 (Lag-3)

Lymphocyte-activation gene 3 (Lag-3, also referred to as CD223) is a transmembrane receptor expressed on activated CD4 and CD8 T cells, γδ T cells, natural killer T cells, B-cells, natural killer cells, plasmacytoid dendritic cells and regulatory T cells. Lag-3 is a member of the immunoglobulin superfamily, is similar in structure to CD4, and comprises four extracellular Ig-like domains (also known as domains D1, D2, D3 and D4, see asterisks in the sequence alignment of FIG. 2). Lag-3 functions to attenuate the immune response and has been reported to bind major histocompatibility complex (MHC) class II molecules (believed to bind through interactions with D1 and D2 domains of Lag-3) and result in delivery of negative signals to Lag-3-expressing cells and down-regulates antigen-dependent CD4 and CD8 T cell responses. Currently, MHC II is the only known binding partner for Lag-3. Lag-3 has also been reported to negatively regulate the ability of T cells to proliferate, produce cytokines and lyse target cells, which is referred to as T cell exhaustion. Further, Lag-3 has been reported to play a role in enhancing regulatory T (Treg) cell function (Pardoll, D. M., 2012, Nat. Rev. Cancer 12:252-64).

T cell co-stimulatory and co-inhibitory molecules (collectively named co-signaling molecules) play a crucial role in regulating T cell activation, subset differentiation, effector function and survival (Chen, L. and D. B. Flies, 2013, Nat. Rev. Immunol. 13:227-42). Following recognition of cognate peptide-MHC complexes on antigen-presenting cells by the T cell receptor, co-signaling receptors co-localize with T cell receptors at the immune synapse, where they synergize with TCR signaling to promote or inhibit T cell activation and function (Flies, D. B. et al., 2011, Yale J. Biol. Med. 84:409-21). The ultimate immune response is regulated by a balance between co-stimulatory and co-inhibitory signals, which have been referred to as "immune checkpoints" (Pardoll, D. M., supra). Such "immune checkpoints" can be described as molecules operating in the immune system to either turn up or down signals, especially T cell signals. Lag-3 functions as one of many "immune checkpoint" in mediating peripheral T cell tolerance.

A more thorough and detailed understanding of Lag-3-mediated functions and the Lag-3 pathway in tumor, auto- and infectious immunity is needed to develop practical targeted therapies for future treatment of human patients.

Lag-3 Sequences

Exemplary rodent (e.g., rat and mouse), human, and humanized lymphocyte-activation gene 3 (Lag-3) sequences are set forth in FIG. 8. An exemplary synthetic DNA fragment for humanization of a non-human Lag-3 gene is also set forth in FIG. 8. For mRNA sequences, bold font indicates coding sequence, and consecutive exons, where indicated, are separated by alternating underlined text; for humanized mRNA sequences, human sequences are contained within parentheses. For amino acid sequences, transmembrane sequences are indicated by underlined font; for humanized amino acid sequences, human sequences are indicated in bold font and contained within parentheses.

DNA Constructs

Typically, a polynucleotide molecule containing a Lag-3 gene, in whole or in part, is inserted into a vector, preferably a DNA vector, in order to replicate the polynucleotide molecule in a suitable host cell.

Depending on size, a Lag-3 gene or Lag-3-encoding sequence can be cloned directly from cDNA sources available from commercial suppliers or designed in silico based on published sequences available from GenBank. Alternatively, bacterial artificial chromosome (BAC) libraries can provide heterologous Lag-3 sequences from genes of interest (e.g., a heterologous Lag-3 gene). BAC libraries contain an average insert size of 100-150 kb and are capable of harboring inserts as large as 300 kb (Shizuya, H. et al., 1992, Proc. Natl. Acad. Sci., U.S.A. 89:8794-7; Swiatek, P. J. and T. Gridley, 1993, Genes Dev. 7:2071-84; Kim, U. J. et al., 1996, Genomics 34:213-8; herein incorporated by reference). For example, human and mouse genomic BAC libraries have been constructed and are commercially available (e.g., Invitrogen, Carlsbad Calif.). Genomic BAC libraries can also serve as a source of heterologous Lag-3 sequences as well as transcriptional control regions.

Alternatively, heterologous Lag-3 sequences may be isolated, cloned and/or transferred from yeast artificial chromosomes (YACs). An entire heterologous gene or locus can be cloned and contained within one or a few YACs. If multiple YACs are employed and contain regions of overlapping homology, they can be recombined within yeast host strains to produce a single construct representing the entire locus. YAC arms can be additionally modified with mammalian selection cassettes by retrofitting to assist in introducing the constructs into embryonic stems cells or embryos by methods known in the art and/or described herein.

Exemplary mRNA and amino acid sequences for use in constructing a humanized Lag-3 gene in a non-human animal are provided herein, e.g., in FIG. 8. Other heterologous Lag-3 sequences can also be found in the GenBank database or other sequence databases known in the art.

DNA constructs containing Lag-3 sequences as described herein, in some embodiments, comprise human LAG-3 genomic sequences encoding an extracellular portion of a human LAG-3 polypeptide, e.g., at least amino acids 29-260 (or 23-260 or 21-260) of a human LAG-3 polypeptide, operably linked to non-human regulatory sequences (e.g., a rodent promoter) for expression in a transgenic non-human animal. In some embodiments, DNA constructs containing Lag-3 sequences as described herein comprise human LAG-3 genomic sequences encoding at least amino acids 29-260 of a human LAG-3 polypeptide operably linked to a non-human Lag-3 promoter and one or more non-human Lag-3 exons (e.g., endogenous Lag-3 exons). Human and/or non-human Lag-3 sequences included in DNA constructs described herein may be identical or substantially identical with human and/or non-human Lag-3 sequences found in nature (e.g., genomic), artificial (e.g., synthetic) or may be engineered by the hand of man. In some embodiments, Lag-3 sequences are synthetic in origin, and include a sequence or sequences that are found in a human LAG-3 gene found in nature. For example, a DNA construct can include synthetic DNA that corresponds to exons 2 through 4 of a human LAG-3 gene, and that encodes an extracellular portion of a human LAG-3 polypeptide, e.g., at least amino acids 29-260 of a human LAG-3 polypeptide, operably linked to non-human Lag-3 regulatory (e.g., promoter) and coding sequences (e.g., one or more non-human exons) so that a Lag-3 polypeptide having human and non-human portions is encoded by the resulting DNA construct. In some embodiments, Lag-3 sequences comprise a sequence naturally associated with a heterologous Lag-3 gene (i.e., a human LAG-3 gene). In some embodiments, Lag-3 sequences comprise a sequence that is not naturally associated with a heterologous Lag-3 gene (i.e., a human LAG-3 gene). In some embodiments, Lag-3 sequences comprise a sequence that is optimized for expression in a non-human animal. In some embodiments, heterologous Lag-3 sequences operably linked to non-human Lag-3 sequences each encode a portion of a Lag-3 polypeptide that appears in separate polypeptides in nature. If additional sequences are useful in optimizing expression of heterologous Lag-3 sequences, such sequences can be cloned using existing sequences as probes. Additional sequences necessary for maximizing expression of a heterologous Lag-3 gene or heterologous Lag-3-encoding sequence can be obtained from genomic sequences or other sources depending on the desired outcome.

DNA constructs can be prepared using methods known in the art. For example, a DNA construct can be prepared as part of a larger plasmid. Such preparation allows the cloning and selection of the correct constructions in an efficient manner as is known in the art. DNA fragments containing one or more nucleotide coding sequences as described herein can be located between convenient restriction sites on the plasmid so that they can be easily isolated from the remaining plasmid sequences for incorporation into the desired animal.

Various methods employed in preparation of plasmids and host organisms containing them are known in the art. For other suitable expression systems for both prokaryotic and eukaryotic cells, as well as general recombinant procedures, see Molecular Cloning: A Laboratory Manual, 2nd Ed., ed. by Sambrook, J. et al., Cold Spring Harbor Laboratory Press: 1989.

Production of Non Human Animals Having A Humanized Lymphocyte-Activation Gene 3

Non-human animals are provided that express humanized Lag-3 polypeptides on the surface of cells of the non-human animals resulting from a genetic modification of an endogenous locus (e.g., a Lag-3 locus) of the non-human animal that encodes a Lag-3 polypeptide. Suitable examples described herein include rodents, in particular, mice.

A humanized Lag-3 gene, in some embodiments, comprises genetic material from a heterologous species (e.g., humans), wherein the humanized Lag-3 gene encodes a Lag-3 polypeptide that comprises the encoded portion of the genetic material from the heterologous species. In some embodiments, a humanized Lag-3 gene as described herein comprises genomic DNA of a heterologous species that encodes an extracellular portion of a Lag-3 polypeptide that is expressed on the plasma membrane of a cell. Non-human animals, embryos, cells and targeting constructs for making non-human animals, non-human embryos, and cells containing said humanized Lag-3 gene are also provided.

In some embodiments, an endogenous Lag-3 gene is deleted. In some embodiments, an endogenous Lag-3 gene is altered, wherein a portion of the endogenous Lag-3 gene is replaced with a heterologous sequence (e.g., a human LAG-3 sequence, in whole or in part). In some embodiments, all or substantially all of an endogenous Lag-3 gene is replaced with a heterologous gene (e.g., a human LAG-3 gene). In some embodiments, a portion of a heterologous Lag-3 gene is inserted into an endogenous non-human Lag-3 gene at an endogenous Lag-3 locus. In some embodiments, the heterologous gene is a human gene. In some embodiments, the modification or humanization is made to one of the two copies of the endogenous Lag-3 gene, giving rise to a non-human animal that is heterozygous with respect to the humanized Lag-3 gene. In other embodiments, a non-human animal is provided that is homozygous for a humanized Lag-3 gene.

In various aspects, a non-human animal contains a human LAG-3 gene, in whole or in part, at an endogenous non-human Lag-3 locus. Thus, such non-human animals can be described as having a heterologous Lag-3 gene. The replaced, inserted, modified or altered Lag-3 gene at the endogenous Lag-3 locus or a polypeptide expressed from such gene can be detected using a variety of methods including, for example, PCR, Western blot, Southern blot, restriction fragment length polymorphism (RFLP), or a gain or loss of allele assay. In some embodiments, the non-human animal is heterozygous with respect to the humanized Lag-3 gene.

In various embodiments, a humanized Lag-3 gene as described herein includes exons 2 through 4 of a human LAG-3 gene.

In various embodiments, a humanized Lag-3 gene as described herein includes a Lag-3 gene that has a second, third and fourth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a second, third and fourth exon that appear in SEQ ID NO:5.

In various embodiments, a humanized Lag-3 gene as described herein includes a Lag-3 gene that has a second, third and fourth exon each having a sequence that is substantially identical or identical to a second, third and fourth exon that appear in SEQ ID NO:5.

In various embodiments, a humanized Lag-3 gene as described herein comprises a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to SEQ ID NO:9, SEQ ID NO:10 or SEQ ID NO:11.

In various embodiments, a humanized Lag-3 gene as described herein comprises a sequence that is substantially identical or identical to SEQ ID NO:9, SEQ ID NO:10 or SEQ ID NO:11.

In various embodiments, a humanized Lag-3 gene as described herein is or comprises SEQ ID NO:10.

In various embodiments, a humanized Lag-3 gene as described herein is or comprises SEQ ID NO:11.

In various embodiments, a humanized Lag-3 gene as described herein comprises exons 1, 5, 6, 7 and 8 of a non-human Lag-3 gene, for example, an endogenous Lag-3 gene of a non-human animal.

In various embodiments, a humanized Lag-3 gene as described herein comprises a first, fifth, sixth, seventh and eighth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a first, fifth, sixth, seventh and eighth exon that appear in SEQ ID NO:1 or SEQ ID NO:3.

In various embodiments, a humanized Lag-3 gene as described herein comprises a first, fifth, sixth, seventh and eighth exon each having a sequence that is substantially identical or identical to a first, fifth, sixth, seventh and eighth exon that appear in SEQ ID NO:1 or SEQ ID NO:3.

In various embodiments, a humanized Lag-3 gene as described herein comprises a 5' untranslated region and a 3' untranslated region of a non-human Lag-3 gene, for example, an endogenous Lag-3 gene of a non-human animal.

In various embodiments, a humanized Lag-3 gene as described herein comprises a 5' untranslated region and a 3' untranslated region each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a 5' untranslated region and a 3' untranslated region that appear in SEQ ID NO:1 or SEQ ID NO:3.

In various embodiments, a humanized Lag-3 gene as described herein comprises a 5' untranslated region and a 3' untranslated region each having a sequence that is substantially identical or identical to a 5' untranslated region and a 3' untranslated region that appear in SEQ ID NO:1 or SEQ ID NO:3.

In various embodiments, a humanized Lag-3 gene as described herein comprises a nucleotide coding sequence (e.g., a cDNA sequence) at least 50% (e.g., 50%, 55%, 60%, 65%, 70%, 75%, 80%, 85%, 90%, 91%, 92%, 93%, 94%, 95%, 96%, 97%, 98%, 99% or more) identical to a nucleotide coding sequence that appears in SEQ ID NO:7.

In various embodiments, a humanized Lag-3 gene as described herein comprises a nucleotide coding sequence (e.g., a cDNA sequence) that is substantially identical or identical to a nucleotide coding sequence that appears in SEQ ID NO:7.

In various embodiments, a humanized Lag-3 gene as described herein encodes a Lag-3 polypeptide having an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence that appears in SEQ ID NO:8.

In various embodiments, a humanized Lag-3 gene as described herein encodes a Lag-3 polypeptide having an amino acid sequence that is substantially identical or identical to an amino acid sequence that appears in SEQ ID NO:8.

In various embodiments, a humanized Lag-3 polypeptide produced by a non-human animal as described herein has an extracellular portion, which extracellular portion comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 29-260 of SEQ ID NO:6 or SEQ ID NO:8.

In various embodiments, a humanized Lag-3 polypeptide produced by a non-human animal as described herein has an extracellular portion substantially identical to an extracellular portion (e.g., an extracellular portion that contains the first two Ig-like domains) of a human LAG-3 polypeptide. In some embodiments, an extracellular portion of a human LAG-3 polypeptide is represented by amino residues 21-260, 23-260, or 29-260 of a human LAG-3 polypeptide, such as a human LAG-3 polypeptide as set forth in SEQ ID NO: 6.

In various embodiments, a humanized Lag-3 polypeptide produced by a non-human animal as described herein has an extracellular portion, which extracellular portion comprises an amino acid sequence that is substantially identical or identical to amino acid residues 29-260 of SEQ ID NO:6 or SEQ ID NO:8.

In various embodiments, a humanized Lag-3 polypeptide produced by a non-human animal as described herein has an extracellular portion, which extracellular portion comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 23-260 of SEQ ID NO:6 or SEQ ID NO:8.

In various embodiments, a humanized Lag-3 polypeptide produced by a non-human animal as described herein has an extracellular portion, which extracellular portion comprises an amino acid sequence that is substantially identical or identical to amino acid residues 23-260 of SEQ ID NO:6 or SEQ ID NO:8.

In various embodiments, a humanized Lag-3 polypeptide produced by a non-human animal as described herein has an extracellular portion, which extracellular portion comprises an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 21-260 of SEQ ID NO:6 or SEQ ID NO:8.

In various embodiments, a humanized Lag-3 polypeptide produced by a non-human animal as described herein has an extracellular portion, which extracellular portion comprises an amino acid sequence that is substantially identical or identical to amino acid residues 21-260 of SEQ ID NO:6 or SEQ ID NO:8.

In various embodiments, a humanized Lag-3 polypeptide produced by a non-human animal as described herein has a transmembrane portion and a cytoplasmic portion of a non-human Lag-3 polypeptide, for example, the transmembrane and cytoplasmic domains of an endogenous Lag-3 polypeptide of a non-human animal. In some embodiments, the transmembrane and cytoplasmic domain sequences of a non-human Lag-3 polypeptide are those illustrated in FIG. 8. In some embodiments, a humanized Lag-3 polypeptide produced by a non-human animal as described herein also has an extracellular portion containing the last two Ig-liked domains of a non-human Lag-3 polypeptide.

In various embodiments, a humanized Lag-3 polypeptide produced by a non-human animal as described herein has an amino acid sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of SEQ ID NO:8.

In various embodiments, a humanized Lag-3 polypeptide produced by a non-human animal as described herein has an amino acid sequence that is substantially identical or identical to an amino acid sequence of SEQ ID NO:8.

Compositions and methods for making non-human animals that express a humanized Lag-3 polypeptide, including specific polymorphic forms, allelic variants (e.g., single amino acid differences) or alternatively spliced isoforms, are provided, including compositions and methods for making non-human animals that express such polypeptides from a human promoter and a human regulatory sequence. In some embodiments, compositions and methods for making non-human animals that express such proteins from a non-human promoter and a non-human regulatory sequence are also provided. In some embodiments, compositions and methods for making non-human animals that express such proteins from an endogenous promoter and an endogenous regulatory sequence are also provided. In some certain embodiments, endogenous promoters and endogenous regulatory sequences are endogenous rodent promoters and endogenous rodent regulatory sequences. The methods include inserting the genetic material encoding a human LAG-3 polypeptide, in whole or in part, at a precise location in the genome of a non-human animal that corresponds to an endogenous Lag-3 gene thereby creating a humanized Lag-3 gene that expresses a Lag-3 protein that is human in whole or in part. In some embodiments, the methods include inserting genomic DNA corresponding to exons 2, 3 and 4 of a human LAG-3 gene into an endogenous Lag-3 gene of the non-human animal thereby creating a humanized gene that encodes a Lag-3 polypeptide that contains a human portion containing amino acids encoded by the inserted exons.

Where appropriate, the coding region of the genetic material or polynucleotide sequence(s) encoding a human (or humanized) Lag-3 polypeptide in whole or in part may be modified to include codons that are optimized for expression from cells in the non-human animal (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding a human (or humanized) Lag-3 polypeptide, in whole or in part, may include an altered sequence to optimize codon usage for a particular cell type (e.g., a rodent cell). For example, the codons of the genomic DNA corresponding to exons 2, 3 and 4 of a human LAG-3 gene to be inserted into an endogenous Lag-3 gene of a non-human animal (e.g., a rodent) may be optimized for expression in a cell of the non-human animal. Such a sequence may be described as a codon-optimized sequence.

Methods for generating transgenic non-human animals, including knockouts and knock-ins, are well known in the art (see, e.g., Gene Targeting: A Practical Approach, Joyner, ed., Oxford University Press, Inc. (2000)). For example, generation of transgenic rodents may optionally involve disruption of the genetic loci of one or more endogenous rodent genes (or gene segments) and introduction of one or more heterologous genes (or Lag-3 encoding sequences) into the rodent genome, in some embodiments, at the same location as an endogenous rodent gene (or gene segments).

In some embodiments, heterologous (or humanized) Lag-3 genes or heterologous Lag-3-encoding sequences as described herein are introduced randomly in the genome of a rodent. In such embodiments, rodents comprising, containing or otherwise harboring randomly introduced heterologous (or humanized Lag-3 genes or heterologous Lag-3-encoding sequences can be characterized as having a heterologous Lag-3 transgene or heterologous Lag-3 transgene construct. Typically, a transgene and/or transgene construct includes, among other things, a nucleic acid sequence (encoding e.g., a polypeptide of interest, in whole or in part) that is introduced into a non-human cell (e.g., a rodent embryonic stem cell) by the hand of man using methods described herein or otherwise known in the art. Further, a transgene may be partly or entirely heterologous, i.e., foreign, to a non-human animal or cell into which it is introduced. A transgene can further include one or more transcriptional regulatory sequences and any other nucleic acid, such as introns or promoters, which may be necessary for expression of a selected nucleic acid sequence. In some embodiments, heterologous (or humanized) Lag-3 genes or heterologous Lag-3-encoding sequences as described herein are introduced into an endogenous Lag-3 gene in the genome of a rodent; in some certain embodiments, an endogenous Lag-3 gene locus is altered, modified, or engineered to contain human Lag-3 sequences (or gene fragments) operably linked to one or more non-human Lag-3 sequences (or gene fragments).

A humanized Lag-3 gene approach employs a relatively minimal modification of the endogenous protein interactions and signaling and results in natural Lag-3-mediated signal transduction in the non-human animal, in various embodiments, because the genomic sequence of the Lag-3 sequences are modified in a single fragment and therefore retain normal functionality by including necessary regulatory sequences. Thus, in such embodiments, the Lag-3 gene modification does not affect other surrounding genes or other endogenous Lag-3-interacting genes (e.g., MHC class II molecules). Further, in various embodiments, the modification does not affect the assembly of a functional Lag-3 transmembrane polypeptide on the cell membrane and maintains normal effector functions via binding and subsequent signal transduction through the cytoplasmic portion of the polypeptide which is unaffected by the modification.

A schematic illustration (not to scale) of the genomic organization of an endogenous murine Lag-3 gene and a human LAG-3 gene is provided in FIG. 1. An exemplary method for humanizing an endogenous murine Lag-3 gene using a genomic fragment containing exons 2, 3 and 4 and a portion of intron 4 (e.g., about 68 bp) of a human LAG-3 gene is provided in FIG. 3. As illustrated, a 1,741 bp synthetic DNA fragment corresponding to exons 2, 3 and 4 and a portion of intron 4 of a human LAG-3 gene is inserted into the place of a 1,750 bp sequence of an endogenous murine Lag-3 gene locus by a targeting construct. The 1,741 bp synthetic DNA fragment may be cloned directly from human DNA or synthesized from a source sequence (e.g., GenBank accession no. NM_002286.5, SEQ ID NO:9). This genomic DNA includes the portion of the gene that encodes at least amino acid residues 29-260 (or 23-260 or 21-260) of a human LAG-3 polypeptide responsible for ligand binding.

Figure 3:
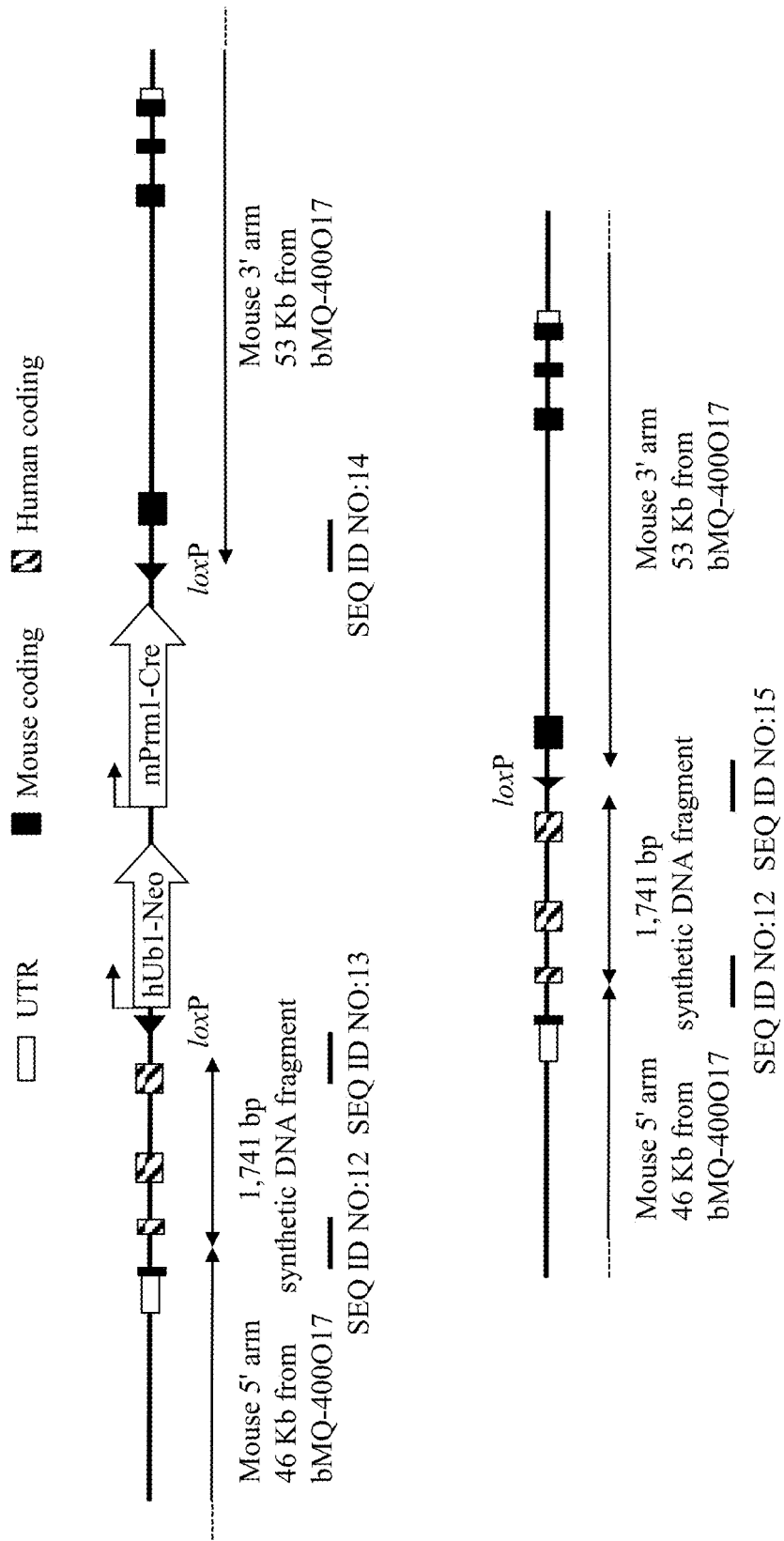
FIG. 3 shows a diagram, not to scale, of an exemplary method for humanization of a non-human Lymphocyte-activation gene 3 (Lag-3). Selected nucleotide junction locations are marked with a line below each junction and each indicated by SEQ ID NO.

A non-human animal (e.g., a mouse) having a humanized Lag-3 gene at the endogenous Lag-3 locus can be made by any method known in the art. For example, a targeting vector can be made that introduces a human LAG-3 gene in whole or in part with a selectable marker gene. FIG. 3 illustrates a targeting vector that contains an endogenous Lag-3 locus of a mouse genome comprising an insertion of a 1,741 bp synthetic DNA fragment that corresponds to exons 2-4 and the first 68 bp of intron 4 of a human LAG-3 gene. As illustrated, the targeting construct contains a 5' homology arm containing sequence upstream of exon 2 (i.e., exon 1, etc.) of an endogenous murine Lag-3 gene (~46 Kb), followed by the 1,741 bp synthetic DNA fragment, a drug selection cassette (e.g., a neomycin resistance gene flanked on both sides by loxP sequences; ~5 Kb), and a 3' homology arm containing the remaining sequence of an endogenous murine exons 5-8 of an endogenous murine Lag-3 gene (~53 Kb). The targeting construct contains a self-deleting drug selection cassette (e.g., a neomycin resistance gene flanked by loxP sequences; see U.S. Pat. Nos. 8,697,851, 8,518,392 and 8,354,389, all of which are incorporated herein by reference). Upon electroporation in embryonic stem cells, a modified endogenous Lag-3 gene is created that includes 1,741 bp of a human LAG-3 gene (i.e., exons 2-4 and the first 68 bp of intron 4) in the place of 1,750 bp of an endogenous wild type Lag-3 gene, which is contained in the targeting vector. A humanized Lag-3 gene is created resulting in a cell or non-human animal that expresses a humanized Lag-3 polypeptide that contains amino acids encoded by the 1,741 bp synthetic DNA fragment (i.e., exons 2-4 and the first 68 bp of intron 4 of a human LAG-3 gene). The drug selection cassette is removed in a development-dependent manner, i.e., progeny derived from mice whose germ line cells containing the humanized Lag-3 gene described above will shed the selectable marker from differentiated cells during development (see bottom of FIG. 3).

In some embodiments, a non-human animal having a humanized Lag-3 gene as described herein can be characterized as transgenic for the humanized Lag-3 gene or a transgenic Lag-3 non-human animal. Such descriptions are used interchangeably herein and refer to any non-naturally occurring non-human animal in which one or more of the cells of the non-human animal contain a heterologous Lag-3 nucleic acid sequence and/or Lag-3-encoding sequence, in whole or in part, as described herein. In some embodiments, a heterologous Lag-3 nucleic acid sequence and/or Lag-3-encoding sequence, in whole or in part, is introduced into a cell, directly or indirectly by introduction into a precursor cell, by way of deliberate genetic manipulation, such as by microinjection or by infection with a recombinant virus. In such embodiments, genetic manipulation does not include classic breeding techniques, but rather is directed to introduction of recombinant DNA molecule(s) that contain a heterologous Lag-3 nucleic acid sequence and/or Lag-3-encoding sequence, in whole or in part, as described herein. Such a molecule may be integrated within a chromosome, or it may be extrachromosomally replicating DNA. As described herein, transgenic non-human animals includes animals that are heterozygous or homozygous for a heterologous Lag-3 nucleic acid sequence and/or Lag-3-encoding sequence, in whole or in part, and/or animals that have single or multiple copies of a heterologous Lag-3 nucleic acid sequence and/or Lag-3-encoding sequence, in whole or in part, as described herein.

A transgenic founder non-human animal can be identified based upon the presence of a humanized Lag-3 gene in its genome and/or expression of Lag-3 polypeptides containing amino acids encoded by the inserted genetic material in tissues or cells of the non-human animal. A transgenic founder non-human animal can then be used to breed additional non-human animals carrying the humanized Lag-3 gene thereby creating a series of non-human animals each carrying one or more copies of a humanized Lag-3 gene. Moreover, transgenic non-human animals carrying a humanized Lag-3 gene can further be bred to other transgenic non-human animals carrying other transgenes (e.g., human immunoglobulin genes) as desired.

Transgenic non-human animals may also be produced to contain selected systems that allow for regulated or directed expression of the humanized Lag-3 gene (or humanized Lag-3 transgene). Exemplary systems include the Cre/loxP recombinase system of bacteriophage P1 (see, e.g., Lakso, M. et al., 1992, Proc. Natl. Acad. Sci. U.S.A. 89:6232-6236) and the FLP/Frt recombinase system of S. cerevisiae (O'Gorman, S. et al, 1991, Science 251:1351-1355). Such animals can be provided through the construction of "double" transgenic animals, e.g., by mating two transgenic animals, one containing a transgene comprising a selected modification (e.g., a humanized Lag-3 gene or transgene) and the other containing a transgene encoding a recombinase (e.g., a Cre recombinase).

The non-human animals as described herein may be prepared as described above, or using methods known in the art, to comprise additional human or humanized genes, oftentimes depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired. In some embodiments, non-human animals as described herein are prepared to further comprise one or more human or humanized genes selected from Programmed cell death protein 1 (PD-1), Programmed death-ligand 1 (PD-L1), and cytotoxic T-lymphocyte-associated protein 4 (CTLA-4). In some embodiments, non-human animals as described herein may be prepared by introducing a targeting vector, as described herein, into a cell from a modified strain. In some embodiments, non-human animals as described herein are prepared to further comprise a human or humanized Programmed cell death protein 1 (Pdcd1) gene. In some embodiments, non-human animals as described herein comprise a humanized Lag-3 gene, as described herein, and genetic material from a heterologous species (e.g., humans), wherein the genetic material encodes, in whole or in part, one or more heterologous proteins selected from Programmed cell death protein 1 (PD-1), Programmed death-ligand 1 (PD-L1), and cytotoxic T-lymphocyte-associated protein 4 (CTLA-4). In some certain embodiments, non-human animals as described herein comprise a humanized Lag-3 gene as described herein and genetic material from a heterologous species (e.g., humans), wherein the genetic material encodes, in whole or in part, a heterologous (e.g., human) PD-1 polypeptide. In some certain embodiments, non-human animals as described herein further comprise a Pdcd1 gene that comprises an endogenous portion and a human portion (e.g., exon 2 and exon 3, in whole or in part, of a human PDCD1 gene), wherein the human portion encodes substantially all of the extracellular domain of a human PD-1 polypeptide (e.g., amino acids corresponding to residues 27-169 or 26-169 of a human PD-1 polypeptide) and the endogenous portion encodes the intracellular domain of an endogenous PD-1 polypeptide; in some embodiments, the human portion and the endogenous portion are operably linked to an endogenous Pdcd1 promoter. In some certain embodiments, non-human animals as described herein further comprise a Pdcd1 gene that includes genetic material that encodes substantially all of the extracellular domain of a human PD-1 polypeptide (e.g., genetic material that encodes amino acids corresponding to residues 27-169 or 26-169 of a human PD-1 polypeptide; see, e.g., SEQ ID NO:23 of PCT/US15/36649, filed 19 Jun. 2015 and published as WO2015196051, and/or SEQ ID NO:23 of U.S. patent application Ser. No. 14/744,592, filed 19 Jun. 2015 and published as US 2015-0366174 A1; incorporated herein by reference). GenBank accession nos. NM_005018.2 and NP_005009.2, and UniProt ID Q15116 provide representative source sequences of a human PDCD1 gene and human PD-1 polypeptide from which a desired human portion may be obtained.

For example, as described herein, non-human animals comprising a humanized Lag-3 gene as described herein may further comprise (e.g., via cross-breeding or multiple gene targeting strategies) one or more modifications as described in PCT/US 15/36649, filed 19 Jun. 2015 and published as 102015196051, and U.S. patent application Ser. No. 14/744,592, filed 19 Jun. 2015 and published as US 2015-0366174 A1; these applications are incorporated herein by reference in their entirety. In certain embodiments, a rodent comprising a humanized Lag-3 gene as described herein is crossed to a rodent comprising a humanized Pdcd1 gene (e.g., exon 2 and a portion of exon 3 of a human PDCD1 gene operably linked to exons 1, a portion of exon 3, 4 and 5 of an endogenous rodent Pdcd1 gene so that the humanized Pdcd1 gene encodes a PD-1 polypeptide includes an extracellular portion from a human PD-1 polypeptide (e.g., corresponding to amino acids residues 27-169 or 26-169) and an intracellular portion from a rodent PD-1 polypeptide protein (see, e.g., SEQ ID NOs:5 and 6 of PCT/US15/36649, filed 19 Jun. 2015 and published as WO2015196051, and/or SEQ ID NOs:5 and 6 of U.S. patent application Ser. No. 14/744,592, filed 19 Jun. 2015 and published as US 2015-0366174 A1; incorporated herein by reference). In certain embodiments, a rodent comprising a humanized Lag-3 gene as described herein is crossed to a rodent comprising a humanized Pdcd1 gene, which humanized Pdcd1 gene includes genetic material that encodes extracellular domain of a human PD-1 polypeptide (e.g., genetic material that encodes amino acids corresponding to residues 27-169 or 26-169 of a human PD-1 polypeptide; see, e.g., SEQ ID NO:23 of PCT/US15/36649, filed 19 Jun. 2015 and published as WO2015196051, and/or SEQ ID NO:23 of U.S. patent application Ser. No. 14/744,592, filed 19 Jun. 2015 published as US 2015-0366174 A1; incorporated herein by reference).

In some embodiments, a humanized Pdcd1 gene comprises a non-human (e.g., rodent) Pdcd1 exon 1, a human PDCD1 exon 2, an exon 3 (which comprises a portion of exon 3 of a human PDCD1 gene and a portion of exon 3 of a non-human (e.g., rodent) Pdcd1 gene), and exons 4-5 of a non-human (e.g., rodent) Pdcd1 gene, and wherein in some embodiments, the portion of exon 3 of a human PDCD1 gene is the 5' portion of human exon 3 that encodes amino acids as part of the extracellular domain of a human PD-1 polypeptide, such as amino acids of a PD-1 stalk sequence, and the portion of exon 3 of a non-human Pdcd1 gene is the 3' portion of non-human exon 3 that encodes amino acids as part of the transmembrane domain of a non-human PD-1 polypeptide. In specific embodiments, a humanized Pdcd1 gene encodes a humanized PD-1 polypeptide that includes an extracellular domain substantially identical to the extracellular domain of a human PD-1 polypeptide, a transmembrane domain substantially identical to the transmembrane domain of a rodent PD-1 polypeptide, and the intracellular domain of a rodent PD-1 polypeptide.

Although embodiments employing a humanized Lag-3 gene in a mouse (i.e., a mouse with a Lag-3 gene that encodes a Lag-3 polypeptide that includes a human portion and a mouse portion) are extensively discussed herein, other non-human animals that comprise a humanized Lag-3 gene are also provided. In some embodiments, such non-human animals comprise a humanized Lag-3 gene operably linked to a rodent Lag-3 promoter. In some embodiments, such non-human animals comprise a humanized Lag-3 gene operably linked to an endogenous Lag-3 promoter; in some embodiments, an endogenous rodent Lag-3 promoter. In some embodiments, such non-human animals express a humanized Lag-3 polypeptide from an endogenous locus, wherein the humanized Lag-3 polypeptide comprises at least amino acid residues 29-260 (e.g., 29-260, 23-260 or 21-260) of a human LAG-3 polypeptide. Such non-human animals include any of those which can be genetically modified to express a Lag-3 polypeptide as disclosed herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Methods for modifying a non-human animal genome (e.g., a pig, cow, rodent, chicken, etc. genome) include, e.g., employing a zinc finger nuclease (ZFN), a transcription activator-like effector nuclease (TALEN), or a Cas protein (i.e., a CRISPR/Cas system) to modify a genome to include a humanized Lag-3 and/or humanized Pdcd1 gene.

Methods Employing Non-Human Animals Having Humanized Lag-3 Genes

The use of humanized mice for biomedical research has advanced understanding of various aspects of the function of human cells, in particular, human immune cells. Indeed, the use of various immunocompromised strains has provided valuable in vivo systems for the investigation of human immune cells. However, they are not without limitation. For example, the use of these models has highlighted distinct differences in mammalian biology, in particular, mammalian immunology. The use of immunocompromised mice for evaluating target immunomodulation is not ideal as aberrant immune function observed in such mice often complicates understanding of displayed phenotypes. This is especially true in the context of the immune response to tumors. Until recently, investigation of the immune responses to tumors (e.g., T cell responses) in mice was confounded by, among other things, mismatching of HLA due to different sources (i.e., donors) of engrafted human cells (Shultz, L. D. et al., 2010, Proc. Nat. Acad. Sci. U.S.A. 107(29):13022-7).

Tumor cells can escape immune recognition and effector response by altering co-stimulatory pathways in T cells. Co-stimulatory pathways mediate the balance among T cell activation, tolerance, and immune-mediated tissue damage by regulating the magnitude and duration of an immune response within the environment of antigenic stimulation. Lymphocyte-activation gene 3 (Lag-3) is a negative regulator of T cell activity and controls the size of the memory T cell pool (Workman, C. J. et al., 2004, J. Immunol. 172:5450-5). The functional role of Lag-3 on antigen-experienced $CD4^+$ and $CD8^+$ T cells has been reported, and upregulation of Lag-3 on these cells following T cell receptor (TCR) engagement leads to negative effects on T cell proliferation, activation, and proinflammatory cytokine production (Huard, B. et al., 1994, Eur. J. Immunol. 24(12):3216-21; Huard, B. et al., 1994, Immunogenetics 39(3):213-7; Macon-Lemaitre, L. and F. Triebel, 2005, Immunol. 115:170-8; Goldberg, M. V. and C. G. Drake, 2011, Curr. Top. Microbiol. Immunol. 344:269-78). Lag-3 blockade has been reported to enhance anti-tumor response in T cells (Grosso, J. F. et al., 2007, J. Clin. Invest. 117:3383-92). Other inhibitory receptors involved in negative regulation of T cell activity include programmed cell death protein 1 (PD-1) and cytotoxic T-lymphocyte-associated protein 4 (CTLA-4). Along with its ligands Programmed Death Ligand 1 (PD-L1, B7-H1 or CD274) and PD-L2 (B7-DC or CD273), PD-1 delivers a checkpoint signal critical for the establishment and maintenance of immune tolerance to environmental and self-antigens (Francisco, L. M. et al., 2010, Immunol. Rev. 236:219-42). PD-1, like Lag-3, has been reported to play a role in evading anti-tumor immunity by allowing tumor cells to escape immune surveillance by the host immune system (Zou, C. 2008, Nat. Rev. Immunol. 8:467-77).

The present invention is, among other things, based on the recognition that the expression of these inhibitory receptors is associated with compromised antigen-specific T cell function in the context of cancer. The present invention is also based on the recognition that the creation of an in vivo system that exploits immune checkpoints can be made using a humanized Lag-3 gene and/or a humanized Pdcd1 gene as described herein. Such an improved in vivo system allows for the development of anti-immune checkpoint therapeutics and/or therapeutic regimens that focus on stimulating anti-tumor immunity in cancer patients. Further, such an improved in vivo system also provides for the development of therapeutics and/or therapeutic regimens that focus on augmenting T cell activity in infectious and/or autoimmune diseases.

Non-human animals as described herein provide an improved in vivo system and source of biological materials (e.g., cells) expressing human (or humanized) Lag-3 that are useful for a variety of assays. In various embodiments, non-human animals as described herein are used to develop therapeutics that target Lag-3 and/or modulate Lag-3 signaling (e.g., disrupting interactions with Lag-3 binding partners, such as MHC class II molecules). In various embodiments, non-human animals as described herein are used to screen and develop candidate therapeutics (e.g., antibodies) that block interaction of human Lag-3 with human MHC class II molecules. In various embodiments, non-human animals as described herein are used to determine the binding profile of antagonists and/or agonists of a humanized Lag-3 on the surface of a cell of a non-human animal as described herein; in some embodiments, non-human animals as described herein are used to determine the epitope or epitopes of one or more candidate therapeutic antibodies that bind human Lag-3.

In various embodiments, non-human animals as described herein are used to determine the pharmacokinetic profiles of anti-Lag-3 antibodies. In various embodiments, one or more non-human animals as described herein and one or more control or reference non-human animals are each exposed to one or more candidate therapeutic anti-Lag-3 antibodies at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals as described herein are used to measure the therapeutic effect of blocking or modulating Lag-3 signaling and the effect on gene expression as a result of cellular changes. In various embodiments, a non-human animal as described herein or cells isolated therefrom are exposed to a candidate therapeutic that binds a humanized Lag-3 polypeptide (or a human portion of a Lag-3 polypeptide) on the surface of a cell of the non-human animal and, after a subsequent period of time, analyzed for effects on Lag-3-dependent processes, for example, adhesion, apoptosis, cytokine production, inflammation, proliferation, self-tolerance and viral infection (or responses).

Non-human animals as described herein express humanized Lag-3 polypeptide, thus cells, cell lines, and cell cultures can be generated to serve as a source of humanized Lag-3 for use in binding and functional assays, e.g., to assay for binding or function of a Lag-3 antagonist or agonist, particularly where the antagonist or agonist is specific for a human Lag-3 sequence or epitope or, alternatively, specific for a human Lag-3 sequence or epitope that associates with MHC class II molecules. In various embodiments, Lag-3 epitopes bound by candidate therapeutic antibodies can be determined using cells isolated from non-human animals as described herein. In various embodiments, a humanized Lag-3 polypeptide expressed by a non-human animal as described herein may comprise a variant amino acid sequence. In various embodiments, non-human animals as described herein express a humanized Lag-3 polypeptide variant. In various embodiments, the variant is polymorphic at an amino acid position associated with ligand binding. In various embodiments, non-human animals as described herein are used to determine the effect of ligand binding through interaction with a polymorphic variant of human Lag-3.

Cells from non-human animals as described herein can be isolated and used on an ad hoc basis, or can be maintained in culture for many generations. In various embodiments, cells from a non-human animal as described herein are immortalized (e.g., via use of a virus) and maintained in culture indefinitely (e.g., in serial cultures).

In various embodiments, cells and/or non-human animals as described herein are used in various immunization regimens to determine the Lag-3-mediated functions in the immune response to an antigen. In some embodiments, candidate therapeutics that bind, or block one or more functions of, human (or humanized) Lag-3 are characterized in a non-human animal as described herein. Suitable measurements include various cellular assays, proliferation assays, serum immunoglobulin analysis (e.g., antibody titer), cytotoxicity assays and immunoprecipitation assays (e.g., characterization of ligand-receptor interactions). In some embodiments, non-human animals as described herein are used to characterize the Lag-3-mediated functions regulating an immune response to an antigen. In some embodiments, the antigen is associated with an autoimmune disease, disorder or condition. In some embodiments, the antigen is associated with an inflammatory disease, disorder or condition. In some embodiments, the antigen is associated with cancer or a neoplasm (e.g., HPV, HCV, HIV, EBV, HHV-8, HTLV-1, MCV, etc.). In some embodiments, the antigen is a test antigen (e.g., ovalbumin or OVA). In some embodiments, the antigen is a target associated with a disease or condition suffered by one or more human patients in need of treatment.

In various embodiments, non-human animals as described herein are used in serum assays for determining titers of autoantibody production for testing the pharmaco-toxicological aspects of candidate therapeutics that target human Lag-3. In some embodiments, autoantibody production in non-human animals as described herein results from one or more autoimmune diseases, disorders or conditions induced in the non-human animal.

In various embodiments, non-human animals as described herein are used for challenge with one or more antigens to determine the therapeutic potential of compounds or biological agents to modulate Lag-3-dependent regulation of an immune response, including but not limited to the specific T cell-dependent responses to a given antigen.

In various embodiments, cells and/or non-human animals as described herein are used in a survival and/or proliferation assay (e.g., employing T and/or B cells) to screen and develop candidate therapeutics that modulate human Lag-3 signaling Activation or loss of Lag-3 plays an important role in the regulation of T cell responses, and regulation of self-tolerance by Lag-3 may result from the activation of specific epitopes of the extracellular domain of Lag-3, therefore, candidate Lag-3 modulators (e.g., antagonists or agonists) may be identified, characterized and developed using cells of non-human animals as described herein and/or a non-human animal as described herein. In some embodiments, cells and/or non-human animals as described herein are used in survival or death assay(s) to determine the effect on proliferation or apoptosis of a specific cell(s) (e.g., cancer cells) in the presence and absence of Lag-3.

In various embodiments, cells and/or non-human animals as described herein are used in xenotransplantation of heterologous (e.g., human) cells or tissue to determine the Lag-3-mediated functions in the physiological (e.g., immune) response to the transplanted human cells or tissue. In some embodiments, candidate therapeutics that bind, or block one or more functions of, human LAG-3 are characterized in a non-human animal as described herein. Suitable measurements include various cellular assays, proliferation assays, serum immunoglobulin analysis (e.g., antibody titer), cytotoxicity assays, and characterization of ligand-receptor interactions (immunoprecipitation assays). In some embodiments, non-human animals as described herein are used to characterize the Lag-3-mediated functions regulating an immune response to an antigen. In some embodiments, the antigen is associated with a neoplasm. In some embodiments, the antigen is associated with an autoimmune disease, disorder or condition. In some embodiments, the antigen is associated with an inflammatory disease, disorder or condition. In some embodiments, the antigen is associated with cancer or a neoplasm. In some embodiments, the antigen is a target associated with a disease or condition suffered by one or more human patients in need of treatment.

In various embodiments, non-human animals as described herein are used in transplantation or adoptive transfer experiments to determine the therapeutic potential of compounds or biological agents to modulate Lag-3-dependent regulation of new lymphocytes and their immune function. In various embodiments, non-human animals as described herein are transplanted with human T cells; in some embodiments, naïve T cells; in some embodiments, activated T cells; in some embodiments, regulatory T cells (Tregs); in some embodiments, memory T cells.

In various embodiments, cells of non-human animals as described herein are used in T cell assays to determine the therapeutic potential of compounds or biological agents to modulate Lag-3-dependent regulation of T cell-dependent response and function. Exemplary T cell assays include, but are not limited to, ELISpot, intracellular cytokine staining, major histocompatibility complex (MHC) restriction, viral suppression assays, cytotoxicity assays, proliferation assays and regulatory T cell suppression assays.

In various embodiments, cells of non-human animals as described herein are used in cell transmigration assays to screen and develop candidate therapeutics that modulate human Lag-3. Cell transmigration involves the migration of cells across the endothelium and transmigration assays permit the measurement of interactions with, and transmigration of, the endothelium by leukocytes or tumor cells.

In various embodiments, cells of non-human animals as described herein are used in tumor cell growth (or proliferation) assays to determine the therapeutic potential of compounds or biological agents to modulate Lag-3-dependent regulation, apoptosis, and/or inhibition of tumor cells.

In various embodiments, cells of non-human animals as described herein are used in cytokine production assays to determine the therapeutic potential of compounds or biological agents to modulate Lag-3-dependent regulation of cytokine release from T cells. In some embodiments, cells of non-human animals as described herein are used for detection (and/or measurement) of intracellular cytokine release resulting from interaction of humanized Lag-3 with a drug targeting human LAG-3 or a Lag-3 binding partner (e.g., MHC class II).

In various embodiments, an autoimmune disease, disorder or condition is induced in one or more non-human animals as described herein to provide an in vivo system for determining the therapeutic potential of compounds or biological agents to modulate Lag-3-dependent regulation of one or more functions of the autoimmune disease, disorder or condition. Autoimmune diseases, disorders or conditions may be induced in one or more non-human animals as described herein followed by administration of one or more compounds or biological agents as desired.

Non-human animals as described herein provide an in vivo system for the analysis and testing of a drug or vaccine. In various embodiments, a candidate drug or vaccine may be delivered to one or more non-human animals as described herein, followed by monitoring of the non-human animals to determine one or more of the immune response to the drug or vaccine, the safety profile of the drug or vaccine, or the effect on a disease or condition. In some embodiments, the vaccine targets a virus such as, for example, human immunodeficiency virus (HIV) or hepatitis virus (e.g., HCV). Exemplary methods used to determine the safety profile include measurements of toxicity, optimal dose concentration, efficacy of the drug or vaccine, and possible risk factors. Such drugs or vaccines may be improved and/or developed in such non-human animals.

Non-human animals as described herein provide an in vivo system for assessing the pharmacokinetic properties of a drug targeting human LAG-3. In various embodiments, a drug targeting human LAG-3 may be delivered or administered to one or more non-human animals as described herein, followed by monitoring of, or performing one or more assays on, the non-human animals (or cells isolated therefrom) to determine the effect of the drug on the non-human animal. Pharmacokinetic properties include, but are not limited to, how an animal processes the drug into various metabolites (or detection of the presence or absence of one or more drug metabolites, including, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug. In some embodiments, pharmacokinetic and pharmacodynamic properties of drugs (e.g., PD-1 modulators) are monitored in or through the use of non-human animals as described herein.

In some embodiments, performing an assay includes determining the effect on the phenotype and/or genotype of the non-human animal to which the drug is administered. In some embodiments, performing an assay includes determining lot-to-lot variability for a Lag-3 modulator (e.g., an antagonist or an agonist). In some embodiments, performing an assay includes determining the differences between the effects of a drug targeting Lag-3 administered to a non-human animal as described herein and a reference non-human animal. In various embodiments, reference non-human animals may have a modification as described herein, a modification that is different from one as described herein (e.g., one that has a disruption, deletion or otherwise non-functional Lag-3 gene and/or Pdcd1 gene, or humanization of a Pdcd1 gene) or no modification (i.e., a wild-type non-human animal).

Exemplary parameters that may be measured in non-human animals (or in and/or using cells isolated therefrom) for assessing the pharmacokinetic properties of a drug targeting human LAG-3 include, but are not limited to, agglutination, autophagy, cell division, cell death, complement-mediated hemolysis, DNA integrity, drug-specific antibody titer, drug metabolism, gene expression arrays, metabolic activity, mitochondrial activity, oxidative stress, phagocytosis, protein biosynthesis, protein degradation, protein secretion, stress response, target tissue drug concentration, non-target tissue drug concentration, transcriptional activity and the like. In various embodiments, non-human animals as described herein are used to determine a pharmaceutically effective dose of a Lag-3 modulator.

Non-human animals as described herein provide an improved in vivo system for the development and characterization of candidate therapeutics for use in cancer. In various embodiments, non-human animals as described herein may be implanted with a tumor, followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of mono-specific antibodies dosed sequentially or simultaneously. The tumor may be allowed sufficient time to be established in one or more locations within the non-human animal. Tumor cell proliferation, growth, survival, etc. may be measured both before and after administration with the candidate therapeutic(s). Cytoxicity of candidate therapeutics may also be measured in the non-human animal as desired.

Non-human animals as described herein may be used to develop one or more disease models to evaluate or assess candidate therapeutics and/or therapeutic regimens (e.g., monotherapy, combination therapy, dose range testing, etc.) to effectively treat diseases, disorders or conditions that affect humans. Various disease conditions may be established in non-human animals as described herein followed by administration of one or more candidate molecules (e.g., drugs targeting Lag-3) so that efficacy of the one or more candidate molecules in a disease condition can determined. In some embodiments, disease models include autoimmune, inflammatory and/or neoplastic diseases, disorders or conditions.

To give but one example, non-human animals as described herein provide an improved animal model for prophylactic and/or therapeutic treatment of a tumor or tumor cells. In various embodiments, non-human animals as described herein may be implanted with one or more tumor cells, followed by administration of one or more candidate therapeutics (e.g., antibodies). In some embodiments, administration of one or more candidate therapeutics is performed subsequent to (e.g., minutes or hours but typically on the same day as) implantation of one or more tumor cells and one or more candidate therapeutics are evaluated in non-human animals as described herein for efficacy in preventing establishment of a solid tumor and/or growth of tumor cells in said non-human animals. In some embodiments, administration of one or more candidate therapeutics is performed subsequent to (e.g., days after) implantation of one or more tumor cells and, in some certain embodiments, after a sufficient time such that one or more implanted tumor cells have reached a predetermined size (e.g., volume) in non-human animals as described herein; and one or more candidate therapeutics are evaluated for efficacy in treatment of one or more established tumors. Non-human animals may be placed into different treatment groups according to dose so that an optimal dose or dose range that correlates with effective treatment of an established tumor can be determined.

Non-human animals as described herein provide an in vivo system for the development and/or characterization of combination therapies including drugs targeting Lag-3 and PD-1 for use in cancer. In various embodiments, non-human animals as described herein may be implanted with one or more tumor cells, followed by administration of drugs (e.g., antibodies) targeting human LAG-3 and human PD-1. In some embodiments, administration of drugs targeting human Lag-3 and human PD-1 is performed subsequent to (e.g., minutes, hours or days after) implantation of one or more tumor cells and combination therapy is evaluated in non-human animals as described herein for efficacy in preventing establishment of a solid tumor and/or growth of tumor cells in said non-human animals. In some embodiments, administration of drugs targeting human LAG-3 and human PD-1 is performed after a sufficient time such that one or more implanted tumor cells have reached a predetermined size (e.g., volume) in non-human animals as described herein; and combination therapy is evaluated for efficacy in treatment of one or more established tumors. Non-human animals may be placed into different treatment groups (including monotherapy groups) so that an optimal treatment regimen that correlates with effective treatment of an established tumor can be determined.

Various disease conditions may be established in non-human animals as described herein followed by administration of one or more candidate molecules (e.g., drugs targeting Lag-3) so that efficacy of the one or more candidate molecules in a disease condition can determined. In some embodiments, disease models include autoimmune, inflammatory and/or neoplastic diseases, disorders or conditions.

Candidate molecules can be administered to non-human animal disease models using any method of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. When a combination therapy is evaluated in non-human animals as described herein, candidate molecules can be administered via the same administration route or via different administration routes. When a dosing regimen is evaluated in non-human animals as described herein, candidate molecules may be administered at bimonthly, monthly, triweekly, biweekly, weekly, daily, at variable intervals and/or in escalating concentrations to determine a dosing regimen that demonstrates a desired therapeutic or prophylactic effect in a non-human animal in which one or more disease models has been established.

Non-human animals as described herein provide an improved in vivo system for the development and characterization of candidate therapeutics for use in infectious diseases. In various embodiments, non-human animals as described herein may be infected by injection with a virus (e.g., MHV, HIV, HCV, EBV, etc.) or pathogen (e.g., bacteria), followed by administration of one or more candidate therapeutics. In some embodiments, candidate therapeutics may include a multi-specific antibody (e.g., a bi-specific antibody) or an antibody cocktail; in some embodiments, candidate therapeutics include combination therapy such as, for example, administration of mono-specific antibodies dosed sequentially or simultaneously; in some embodiments, candidate therapeutics may include a vaccine. The virus or pathogen may be allowed sufficient time to be established in one or more locations or cells within the non-human animal so that one or more symptoms associated with infection of the virus or pathogen develop in the non-human animal. T cell proliferation and growth may be measured both before and after administration with the candidate therapeutic(s). Further, survival, serum and/or intracellular cytokine analysis, liver and/or spleen histopathology may be measured in non-human animals infected with the virus or pathogen. In some embodiments, non-human animals as described herein are used to determine the extent of organ damage associated with viral infection. In some embodiments, non-human animals as described herein are used to determine the cytokine expression profile in various organs of non-human animals infected with a particular virus.

Non-human animals as described herein can be employed to assess the efficacy of a therapeutic drug targeting human cells. In various embodiments, a non-human animal as described herein is transplanted with human cells, and a drug candidate targeting such human cells is administered to such non-human animal. The therapeutic efficacy of the drug is then determined by monitoring the human cells in the non-human animal after the administration of the drug. Drugs that can be tested in the non-human animals include both small molecule compounds, i.e., compounds of molecular weights of less than 1500 kD, 1200 kD, 1000 kD, or 800 daltons, and large molecular compounds (such as proteins, e.g., antibodies), which have intended therapeutic effects for the treatment of human diseases and conditions by targeting (e.g., binding to and/or acting on) human cells.

In some embodiments, the drug is an anti-cancer drug, and the human cells are cancer cells, which can be cells of a primary cancer or cells of cell lines established from a primary cancer. In these embodiments, a non-human animal as described herein is transplanted with human cancer cells, and an anti-cancer drug is given to the non-human animal. The efficacy of the drug can be determined by assessing whether growth or metastasis of the human cancer cells in the non-human animal is inhibited as a result of the administration of the drug.

In specific embodiments, the anti-cancer drug is an antibody molecule, which binds an antigen on human cancer cells. In particular embodiments, the anti-cancer drug is a bi-specific antibody that binds to an antigen on human cancer cells, and to an antigen on other human cells, for example, cells of the human immune system (or "human immune cells") such as T and B cells.

Kits

The present invention further provides a pack or kit comprising one or more containers filled with at least one non-human animal, non-human cell, DNA fragment (or construct), and/or targeting vector as described herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both, or a contract that governs the transfer of materials and/or biological products (e.g., a non-human animal or non-human cell as described herein) between two or more entities.

Other features of the invention will become apparent in the course of the following descriptions of exemplary embodiments, which are given for illustration and are not intended to be limiting thereof.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Lymphocyte-Activation Gene 3

This example illustrates exemplary methods of humanizing an endogenous Lymphocyte-activation gene 3 (Lag-3) in a non-human mammal such as a rodent (e.g., a mouse). The methods described in this example can be employed to humanize an endogenous Lag-3 gene of a non-human animal using any human sequence, or combination of human sequences (or sequence fragments) as desired. In this example, a 1,741 bp synthetic DNA fragment containing exons 2, 3 and 4 of a human LAG3 gene that appears in GenBank accession NM_002286.5 (SEQ ID NO:9) is employed for humanizing an endogenous Lag-3 gene of a mouse. Alignment of mouse, human, and exemplary humanized protein generated herein, with humanized region underlined, is depicted in FIG. 2. FIG. 3 shows a targeting vector for humanization of the genetic material encoding amino acids 21-260 of a rodent Lag-3 polypeptide that was constructed using VELOCIGENE® technology (see, e.g., U.S. Pat. No. 6,586,251 and Valenzuela et al., 2003, Nature Biotech. 21(6):652-659; herein incorporated by reference).

Briefly, mouse bacterial artificial chromosome (BAC) clone bMQ-400O17 (Invitrogen) was modified to delete the sequence containing exons 2-4 (1,750 bp) of an endogenous Lag-3 gene and insert exons 2, 3 and 4 of a human LAG-3 gene using a 1,741 bp synthetic DNA fragment, which encodes amino acids 21-260 of a human LAG-3 polypeptide. Endogenous DNA containing exons 1, 5, 6, 7 and 8 as well as the 5' and 3' untranslated regions (UTRs) were retained. Sequence analysis of the 1,741 bp synthetic DNA fragment (i.e., corresponding to exons 2-4 of a human LAG3 gene) confirmed all human LAG-3 exons and splicing signals. Sequence analysis revealed that the sequence matched the reference genome and LAG-3 transcript NM_002286.5.

The 1,741 bp synthetic DNA fragment was synthesized by Genescript Inc. (Piscataway, N.J.) and cloned into an ampicillin-resistant plasmid vector. Unique restriction enzyme recognition sites were employed to ligate a ~4,996 bp self-deleting neomycin cassette flanked by recombinase recognition sites (loxP-hUbl-em7-Neo-pA-mPrm1-Crei-loxP; see U.S. Pat. Nos. 8,697,851, 8,518,392 and 8,354,389, all of which are incorporated herein by reference). Subsequent selection employed neomycin. The targeting vector was linearized prior to homologous recombination with mouse BAC clone bMQ-400O17. By design, the junction between the human LAG-3 1,741 bp fragment and the mouse downstream 509 bp included a portion of intron 4 of a human LAG-3 gene (FIG. 3). The resulting targeting vector contained, from 5' to 3', a 5' homology arm containing ~46 kb of mouse genomic DNA from BAC clone bMQ-400O17, 1,741 bp synthetic DNA fragment (corresponding to exons 2-4 and a portion of intron 4 of a human LAG-3 gene), a self-deleting neomycin cassette flanked by loxP sites, and ~53 kb of mouse genomic DNA from BAC clone bMQ-400O17.

The modified bMQ-400O17 BAC clone described above was used to electroporate mouse embryonic stem (ES) cells to create modified ES cells comprising an endogenous Lag-3 gene that is humanized from exon 2 through exon 4 including a portion of intron 4 (i.e., deletion of 1,750 bp of an endogenous Lag-3 gene and insertion of 1,741 bp of human LAG-3 sequence). Positively targeted ES cells containing a humanized Lag-3 gene were identified by an assay (Valenzuela et al., supra) that detected the presence of the human LAG-3 sequences (e.g., exons 2-4) and confirmed the loss and/or retention of mouse Lag-3 sequences (e.g., exons 2-4 and/or exons 1, 4, 5, 6, 7 and 8). Table 1 sets forth the primers and probes that were used to confirm humanization of an endogenous Lag-3 gene as described above (FIG. 4).

The nucleotide sequence across the upstream insertion point included the following, which indicates endogenous mouse sequence (contained within the parentheses below) contiguous with human LAG-3 genomic sequence at the insertion point:

(SEQ ID NO: 12)
(CATGATGTTT CTTTCTTAGG AAAGCCAGGG CATTTCTCTA

TTCTCCAATC TCTTGGCTCA ATGCCCTTGG CCTCTCTTTT

GTTCCACTAG) TGAAGCCTCT CCAGCCAGGG GCTGAGGTC

CCGGTGGTG TGGGCCCAG GAGGGGGCTC CTGCCCAGCT CCC (FIG. 9A).

The nucleotide sequence across the 5' end of the self-deleting neomycin cassette included the following, which indicates human LAG-3 genomic sequence contiguous with cassette sequence (contained within the parentheses below with a SalI-XhoI compatible end italicized and a loxP sequence in bold font) downstream of the insertion point:

(SEQ ID NO: 13)
TTCACATTTG ACCACAACTC CTTCCTGCCC CCCTTGTCAC

CTCCCCTAAC (*GTCGAG* ATAACTTCG TATAATGTAT GCTATACGAA

GTTAT ATGCATGGCC TCCGCGCCGG GTTTTGGCGC CTCCCGCGGG

CGCCCCCCTC CTCACGGCGA GCGCTGCCAC GTCAGACGAA

GGGCGCAGCG AGCGTCCTGA) (FIG. 9B).

The nucleotide sequence across the downstream insertion point at the 3' end of the self-deleting neomycin cassette included the following, which indicates cassette sequence (contained within the parentheses below with a loxP site in bold, an I-CeuI recognition site underlined and an NheI recognition site italicized) contiguous with mouse Lag-3 genomic sequence:

(SEQ ID NO: 14)
(TTTCACTGCAT TCTAGTTGTG GTTTGTCCAA ACTCATCAAT

GTATCTTATC ATGTCTGGA ATAACTTCGT ATAATGTATG

CTATACGAAG TTAT *GCTAG*TAACT ATAACGGTCC TAAGGTAGCG A

*GCTAGC*) GACCCCCAAA ACTTTCTCAG CTGCGTGTGG

TCTCACTCCA CATCACTTTG TTTCAGTGTC CAAACCATTT

TCTCTCTGGG CATCTTTTAG (FIG. 9C).

The nucleotide sequence across the upstream insertion point after deletion of the neomycin cassette (77 bp remaining in intron 4) included the following, which indicates mouse and human genomic sequence juxtaposed with remaining cassette sequence loxP sequence (contained within the parentheses below with a SalI-XhoI compatible end italicized, a loxP site in bold, an I-CeuI restriction site underlined and an NheI restriction site italicized):

```
                                        (SEQ ID NO: 15)
ACGTCTCCAT CATGTATAAC CTCACTGTTC TGGGTAACT

CCCCCACTCT GCTTCACATT TGACCACAAC TCCTTCCTGC

CCCCCTTGTC ACCTCCCCT AAC (GTCGAG ATAACTTCGTA

TAATGTATGC TATACGAAGT TAT GCTAGTA ACTATAACGG

TCCTAAGGTA GCGA GCTAGC) GACCCCCAAA ACTTTCTCAG

CTGCGTGTGG TCTCACTCCA CATCACTTTG TTTCAGTGTC

CAAACCATTT TCTCTCTGG GCATCTTTTA GCTGCTGTCTC (FIG. 9D).
```

Figure 4:
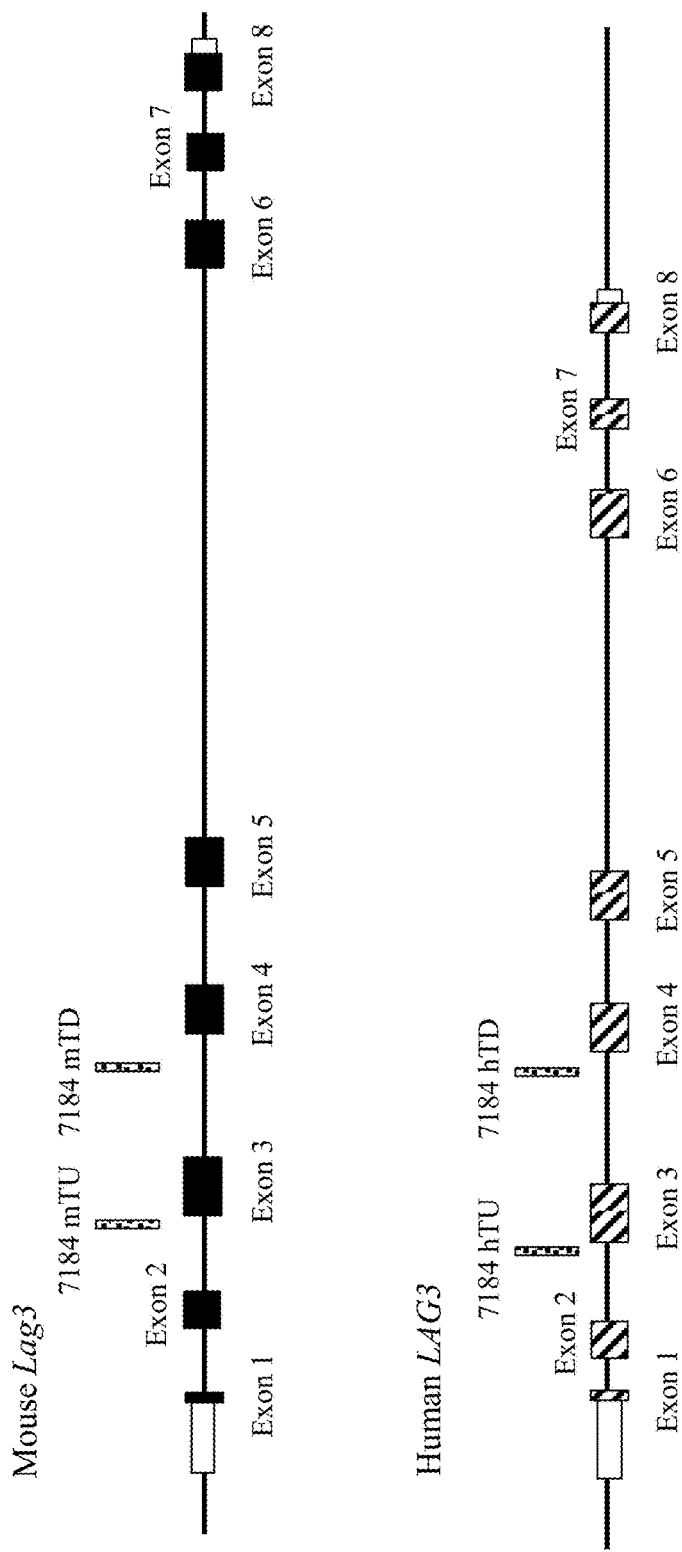
FIG. 4 shows a diagram, not to scale, of the genomic organization of a mouse and human Lymphocyte-activation gene 3 (Lag-3) indicating the approximate locations of probes employed in an assay described in Example 1.

Positive ES cell clones were then used to implant female mice using the VELOCIMOUSE® method (see, e.g., U.S. Pat. No. 7,294,754 and Poueymirou et al., 2007, Nature Biotech. 25(1):91-99) to generate a litter of pups containing an insertion of human LAG-3 exons 2-4 and part of human LAG-3 intron 4 into an endogenous Lag-3 gene of a mouse. Mice bearing the humanization of exons 2-4 (i.e., the 1,741 bp synthetic DNA fragment) of an endogenous Lag-3 gene were again confirmed and identified by genotyping of DNA isolated from tail snips using an assay as previously described (Valenzuela et al., supra) that detected the presence of the human LAG-3 gene sequences (FIG. 4). Pups are genotyped and cohorts of animals heterozygous for the humanized Lag-3 gene construct are selected for characterization.

LAG-3 in T cells stimulated with anti-CD3/anti-CD28 antibodies. Further, expression of PD-1 and LAG-3 was examined on T cells of humanized Lag-3 mice that further contained a humanized Pdcd1 (PD-1) gene (double humanized Lag3xPD1 mice).

First, double humanized Lag3xPD1 mouse embryonic stem (ES) cells were generated using the Lag-3 targeting vector described above (see Example 1) in humanized Pdcd1 mouse ES cells (for humanized PD-1 mice and embryonic stems cells see U.S. patent application Ser. No. 14/744,592, filed 19 Jun. 2015 and published as US 2015-0366174 A1 (including particularly Example 1 therein), and International Patent Application No. PCT/US15036649, filed 19 Jun. 2015 and published as WO2015196051; both of which are incorporated herein by reference). Double humanized mouse ES cells were created by electroporation of the Lag-3 targeting vector as described in Example 1 into C57BL/6N mouse embryonic stem cells that contained a humanized Pdcd1 gene that encoded a PD-1 polypeptide having a human portion and a mouse portion, which human portion included the extracellular domain of a human PD-1 polypeptide. Double humanized ES cell clones were then used to implant female mice using the VELOCIMOUSE® method (see, e.g., U.S. Pat. No. 7,294,754 and Poueymirou et al., 2007, Nature Biotech. 25(1):91-99) to generate a litter of pups containing both humanized genes (i.e., Lag-3 and Pdcd1). The mouse colony was expanded by interbreeding.

Briefly, spleens were harvested and processed from wild type, humanized Lag-3 mice made according to Example 1, humanized PD-1 mice, and double humanized Lag3xPD1 mice (described above) into single cell suspensions by mechanical dissociation. Cells were washed in media (RPMI supplemented with 10% FBS), re-suspended at 1×10⁶/mL and 200 μL (200,000 cells) were plated in 96-well plates. Cells in selected wells were stimulated with anti-CD3 and anti-CD28 antibodies (both at 1 μg/mL) for 72 hours. Cells were stained for FACS according to manufacturer's speci-

TABLE 1

| Name | Primer/ Probe | Sequence (5'-3') | |
|---|---|---|---|
| 7184 mTU | Forward | GAGGCTGCTGACGGTCAAG | (SEQ ID NO: 16) |
| | Probe | TTAGGCAGGTTAACTTTATCCTCAAAGCA | (SEQ ID NO: 17) |
| | Reverse | GCCACGAAGAAGATGCACTCAAG | (SEQ ID NO: 18) |
| 7184 mTD | Forward | GTCCCGGGTCTCTTGGAGAT | (SEQ ID NO: 19) |
| | Probe | CCACCCATAAACATCCCCAGGTTTCA | (SEQ ID NO: 20) |
| | Reverse | CCGCTCATTCCAAGTCAGTTC | (SEQ ID NO: 21) |
| 7184 hTU | Forward | CGGTTGGTGGTCAAGAGAAC | (SEQ ID NO: 22) |
| | Probe | CGGGCTTTCTCATCCTCAACGGG | (SEQ ID NO: 23) |
| | Reverse | GGCGGGAAAGAGAATGGAGTTG | (SEQ ID NO: 24) |
| 7184 hTD | Forward | AGCCCTGCTGTGTTGGGAAA | (SEQ ID NO: 25) |
| | Probe | TGTTTCCAGTGGGCTGATGAAGTC | (SEQ ID NO: 26) |
| | Reverse | TGGCAGTCACTGTGCAAG | (SEQ ID NO: 27) |

Example 2. Expression of Humanized Lag-3 on Activated T Cells

This Example demonstrates that non-human animals (e.g., rodents) modified to contain a humanized Lag-3 gene according to Example 1 express a humanized Lag-3 polypeptide on the surface of activated lymphocytes. In particular, activated T cells from wild type mice and mice homozygous for humanized Lag-3 (as described above) were stained with anti-Lag-3 antibodies to determine the expression of fications with antibodies recognizing CD4 and CD8, BV421 (Brilliant Violet 421™-conjugated antibody to human PD-1 (clone EH12.2H7, Biolegend), BV421-conjugated antibody to mouse PD-1 (clone J43, BD Biosciences), allophycocyanin-conjugated antibody to human LAG-3 (clone 3DS223H, eBioscience), allophycocyanin-conjugated antibody to mouse Lag-3 (clone C9B7W, Biolegend) or corresponding isotype controls. Stained cells were run on LSRII flow cytometer and data was analyzed using Flowjo software.

CD4+ T cells were gated (CD19−CD4+) for expression of human and mouse Lag-3. Representative results are shown in FIG. 5.

Figure 5:
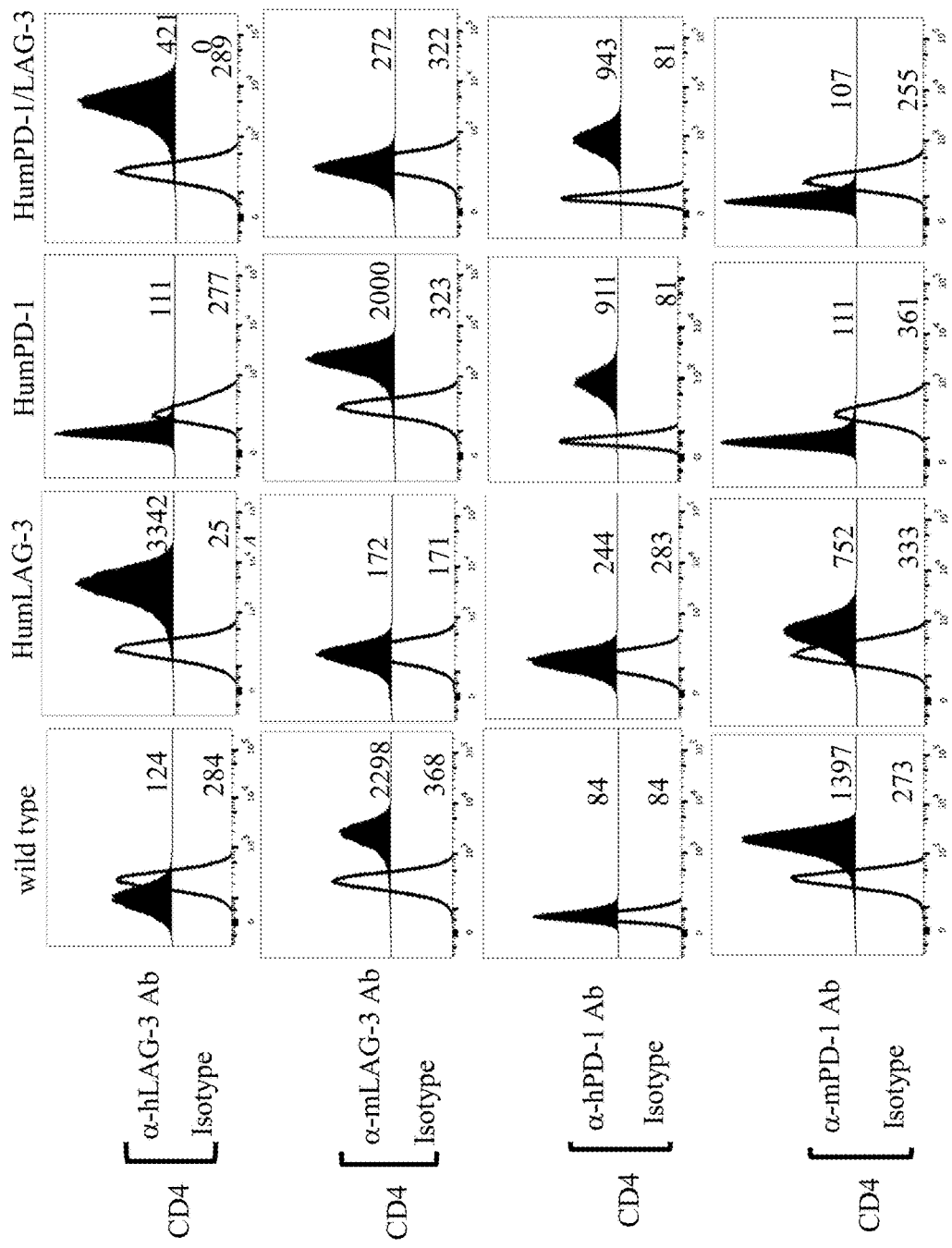
FIG. 5 shows representative histograms of activated splenocytes from wild type C57BL/6 (wild type), homozygous humanized Lag-3 (HumLAG-3), homozygous humanized PD-1 (HumPD-1), and homozygous double humanized Lag-3xPD-1 (HumPD-1xLAG-3) mice stained with antibodies to human LAG-3, human PD-1, mouse Lag-3, and mouse PD-1 or stained with respective isotype control antibody. Positive staining is indicated by filled curves, while staining with isotype control antibodies is indicated by unfilled curves. All staining profiles represent cells within CD4$^+$ gating. Medium florescent intensity (MFI) with antibody staining on CD4$^+$ T cells is indicated for each histogram (top row: human LAG-3 expression; 2nd row: mouse Lag-3 expression; 3rd row: human PD-1 expression; bottom row: mouse PD-1 expression). Genotype of mice is indicated at the top of each column. For humanized PD-1 mice see U.S. patent application Ser. No. 14/744,592, filed 19 Jun. 2015, and International Patent Application No. PCT/US15/036649, filed 19 Jun. 2015; both of which are incorporated herein by reference.

As shown in FIG. 5, activated CD4+ T cells from wild type mouse (FIG. 5, left column) show robust expression of mouse PD-1 (bottom left) and mouse Lag-3 (2nd from top left), but a complete lack of human PD-1 and human LAG-3 expression. This demonstrated that anti-human PD-1 and anti-human LAG-3 antibodies do not cross-react with mouse PD-1 and mouse Lag-3 proteins, respectively. Activated CD4+ T cells from single humanized Lag-3 mice detectably express humanized Lag-3 and mouse PD-1, but not mouse Lag-3 and human PD-1 (FIG. 5, second column from left). Correspondingly, activated CD4+ T cells from single humanized Pdcd1 mice express humanized PD-1 and mouse Lag-3, but lack any expression of mouse PD-1 and human LAG-3 (FIG. 5, third column from left). Double humanized Lag3xPD1 mice demonstrated expression of human but not mouse PD-1 and Lag-3 proteins, which confirmed that full-length mouse PD-1 and Lag-3 polypeptides are not produced in these mice.

Taken together, this Example demonstrates that mice bearing a humanized Lag-3 gene as described in Example 1 express a Lag-3 polypeptide that comprises a human portion and an endogenous mouse portion, which human portion is detectably expressed via recognition by an antibody that recognizes human LAG-3 polypeptide. This Example also demonstrates that double humanized Lag3xPD1 mice expressing both humanized PD-1 and humanized Lag-3 polypeptides provide an in vivo system for testing the efficacy of anti-Lag-3 and/or anti-PD1 antibodies.

Example 3. In Vivo Efficacy of LAG3 and PD1 Modulators

This Example demonstrates that non-human animals (e.g., rodents) modified to contain a humanized Lag-3 gene according to Example 1 can be used in an in vivo assay to screen both Lag-3 and PD-1 modulators (e.g., anti-Lag-3 and anti-PD-1 antibodies) and determine various characteristics such as, for example, inhibition of tumor growth and/or killing of tumor cells. In this Example, anti-Lag-3 and anti-PD-1 antibodies are screened in mice homozygous for humanization of an endogenous Lag-3 gene as described in Example 1 and homozygous for humanization of an endogenous Pdcd1 gene to determine the efficacy of mono- and combination therapy using anti-Lag-3 and anti-PD1 antibodies.

MC38, a mouse adenocarcinoma cell line, originated from a C57BL/6 mouse strain, was obtained from the National Health Institute depository. The MC38.Ova cell line was engineered by stable lenti-viral transduction to express transmembrane chicken ovalbumin antigen (Ova) to increase tumor immunogenicity. Cell lines were tested for human and rodent pathogens before being implanted into mice. Cells were suspended in 100 μl serum-free RPMI medium and implanted subcutaneously into the mouse flank.

Briefly, in vivo efficacy of anti-Lag-3 and anti-PD-1 antibodies alone and in combination was examined using MC38.Ova tumors implanted in double humanized Lag3xPD1 mice. Mice were implanted subcutaneously with MC38.Ova cells on day 0 and randomized into four treatment groups (n=7-12 for each treatment group). Mice were administered a control antibody (n=7, 25 mg/kg), anti-Lag-3 (n=12, 25 mg/kg), anti-PD-1 (n=12, 10 mg/kg), or anti-Lag-3 and anti-PD-1 antibody combination (n=12, 25 mg/kg and 10 mg/kg, respectively) via intraperitoneal injection on days 3, 7, 10, 14 and 17. Tumor volumes were monitored by caliper measurement twice per week for the duration of the experiment (32 days) and tumor free animals were monitored for the absence of tumor recurrence for up to 80 days. Representative results are shown in FIG. 6.

Figure 6:
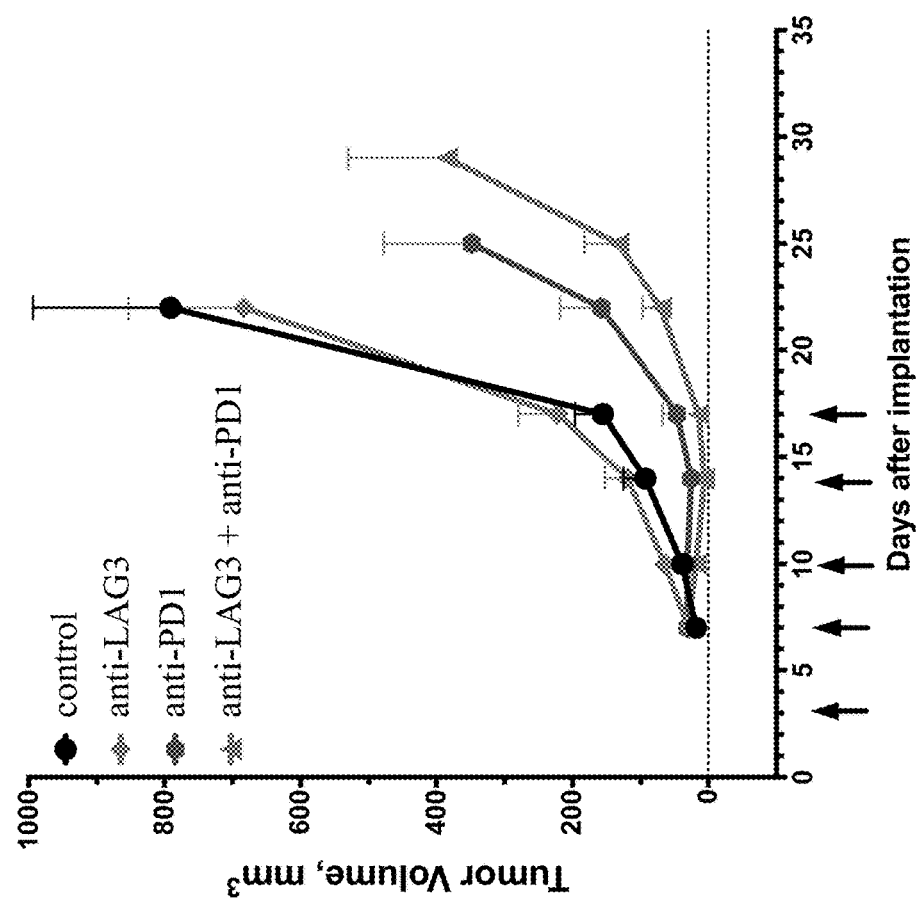
FIG. 6 shows representative average tumor volume (mm$^3$±SEM) over 35 days in various treatment groups of double humanized Lag-3/PD-1 mice (control, circle: human isotype control antibody not specific for mouse or human LAG-3 or mouse or human PD-1; anti-LAG3, diamond: anti-human LAG-3 antibody; anti-PD1, hexagon: anti-human PD-1 antibody;). Arrows indicate the days of antibody treatment.

As shown in FIG. 6, anti-PD-1 monotherapy resulted in tumor growth inhibition, with tumor regression in 2 out of 12 (17%) animals whereas anti-Lag-3 monotherapy was not significantly efficacious in this experiment. Tumor regression was observed in 1 out of 12 mice treated with anti-Lag-3 antibody. There were no tumor-free mice on day 32 for the control group. By contrast, combination therapy with anti-Lag-3 and anti-PD-1 demonstrated robust inhibition of MC38.Ova tumor growth, resulting in 5 out of 12 (42%) tumor-free mice by the end of experiment (FIG. 6). None of the tumor-free mice showed tumor recurrence for 80 days post-implantation, which indicated long-lasting effects of combination immunotherapy.

In a separate experiment, double humanized Lag3xPD1 mice were inoculated with MC38.Ova tumor cells subcutaneously on day 0. On day 10 mice with an average tumor volume of 100 mm³ were selected and randomized into four treatment groups. Mice were administered anti-Lag-3 antibody (n=9, 25 mg/kg), anti-PD-1 antibody (n=10, 10 mg/kg), anti-lag-3 antibody and anti-PD-1 antibody combination (N=11, 25 mg/kg and 10 mg/kg, respectively) or a control antibody (n=7, 25 mg/kg) by IP injection on days 10, 14, 17, 22. Tumor volumes were monitored for 28 days post tumor implantation.

Figure 7:
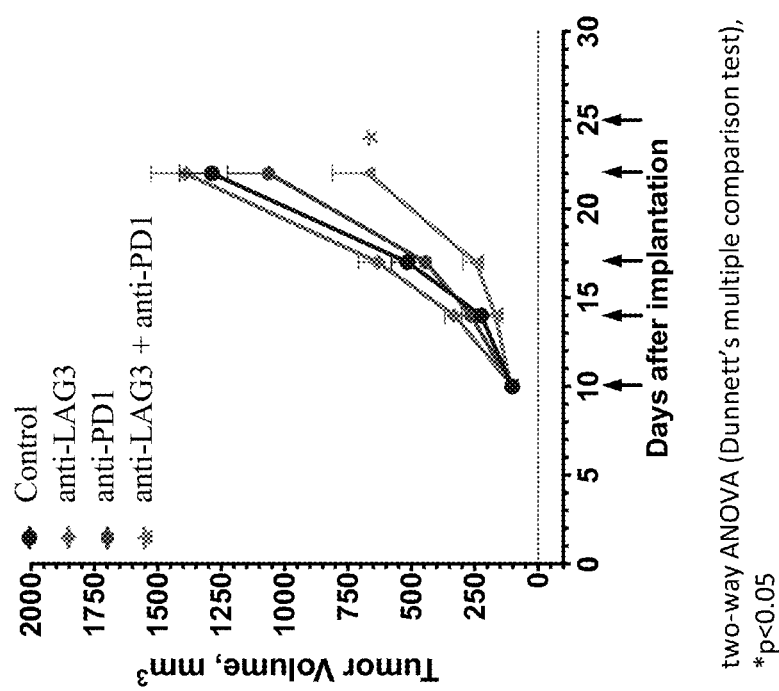
FIG. 7 shows average tumor volumes (mm$^3$±SEM) in various treatment groups of double humanized Lag-3/PD-1 mice at multiple time points post tumor implantation in an experiment to assess efficacy of anti-LAG3 antibody alone and in combination with anti-human PD-1 antibody against established MC38 tumors (control, circle: human isotype control antibody not specific for mouse or human LAG-3 or mouse or human PD-1; anti-LAG3, diamond: anti-human LAG-3 antibody; anti-PD1, hexagon: anti-human PD-1 antibody; anti-LAG3+anti-PD-1, triangle: combination of anti-human LAG-3 antibody and anti-human PD-1 antibody). Treatment days are indicated by arrows.

As shown in FIG. 7, treatment of MC38.ova tumor-bearing humanized mice (established tumors) with a combination of anti-hPD-1 and anti-hLAG-3 antibodies triggered activation of intratumoral and peripheral T cells. Combination of anti-hPD-1 and anti-hLAG-3 antibodies demonstrated robust inhibition of MC38.Ova tumor growth. Combination therapy in these mice also resulted in significant increase in animal survival, as well as duration of survival (data not shown).

Taken together, this Example demonstrates that non-human animals described herein can be used to assess the in vivo efficacy of drugs (e.g., one or more antibodies) targeting Lag-3 and/or PD-1, and such animals are useful in discriminating the therapeutic and prophylactic effect of anti-Lag-3 monotherapy and/or combination therapy using anti-PD-1 antibodies. Moreover, non-human animals described herein can be used to assess the extent to which drugs targeting Lag-3 or PD-1 can inhibit tumor growth and/or mediate killing of tumor cells.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein. The publications, websites and other reference materials referenced herein to describe the background of the invention and to provide additional detail regarding its practice are hereby incorporated by reference.

What is claimed is:

1. A mouse whose genome comprises a humanized Lymphocyte activation gene 3 (Lag-3) gene at an endogenous Lag-3 locus,
   wherein a humanized Lag-3 polypeptide is expressed from the humanized Lag-3 gene on the surface of activated T-lymphocytes in the mouse,
   wherein the humanized Lag-3 polypeptide comprises (i) the first two N-terminal immunoglobulin-like domains of a human LAG-3 polypeptide and (ii) the transmembrane and intracellular domains of an endogenous mouse Lag-3 polypeptide, and
   wherein the humanized Lag-3 gene is operably linked to the endogenous mouse Lag-3 promoter at the endogenous Lag-3 locus.

2. The mouse of claim 1, wherein the humanized Lag-3 polypeptide comprises amino acids 29-260 of the human LAG-3 polypeptide, wherein the human LAG-3 polypeptide comprises the amino acid sequence as set forth in SEQ ID No. 6.

3. The mouse of claim 1, wherein the humanized Lag-3 gene comprises endogenous mouse Lag-3 exons 1, 5, 6, 7 and 8.

4. The mouse of claim 1, wherein the humanized Lag-3 gene comprises exons 2-4 of a human LAG-3 gene.

5. A humanized Lag-3 polypeptide produced by the mouse of claim 1.

6. An isolated cell or tissue of the mouse of claim 1, wherein the genome of the isolated cell or tissue comprises the humanized Lag-3 gene at the endogenous Lag-3 locus.

7. A method of making a mouse comprising
modifying a mouse genome so that the modified genome comprises a humanized Lag-3 gene at an endogenous Lag-3 locus, thereby making the mouse,
wherein a humanized Lag-3 polypeptide is expressed from the humanized Lag-3 gene on the surface of activated T-lymphocytes in the mouse, and
wherein the humanized Lag-3 polypeptide comprises (i) the first two N-terminal immunoglobulin-like domains of a human LAG-3 polypeptide and (ii) the transmembrane and intracellular domains of an endogenous mouse Lag-3 polypeptide, and
wherein the humanized Lag-3 gene is operably linked to the endogenous mouse Lag-3 promoter at the endogenous Lag-3 locus.

8. The method of claim 7, comprising
(a) integrating a genomic fragment into an endogenous Lag-3 gene in a mouse ES cell, the genomic fragment comprising a nucleotide sequence that encodes the first two N-terminal immunoglobulin-like domains of the human LAG-3 polypeptide, thereby obtaining a genetically modified mouse embryonic stem cell; and,
(c) creating a mouse using the genetically modified mouse ES cell of (a).

9. The method of claim 7, wherein the humanized Lag-3 gene comprises exons 2-4 of a human LAG-3 gene.

10. The method of claim 7, wherein the humanized Lag-3 gene encodes at least amino acids 29-260 of the human LAG-3 polypeptide, wherein the human LAG-3 polypeptide comprises the amino acid sequence as set forth in SEQ ID No. 6.

* * * * *